US009795330B2

(12) United States Patent
Pascal et al.

(10) Patent No.: US 9,795,330 B2
(45) Date of Patent: Oct. 24, 2017

(54) DEVICE, SYSTEM AND METHOD FOR IN-VIVO DETECTION OF BLEEDING IN THE GASTROINTESTINAL TRACT

(71) Applicant: GIVEN IMAGING LTD., Yoqneam (IL)

(72) Inventors: Amit Pascal, Haifa (IL); Zvika Gilad, Haifa (IL); Elisha Rabinovitz, Haifa (IL); Yaniv Birnboim, Shaarey-Tikva (IL)

(73) Assignee: GIVEN IMAGING LTD., Yoqneam (IL)

( * ) Notice: Subject to any disclaimer, the term of this patent is extended or adjusted under 35 U.S.C. 154(b) by 38 days.

(21) Appl. No.: 14/304,690

(22) Filed: Jun. 13, 2014

(65) Prior Publication Data
US 2014/0296666 A1    Oct. 2, 2014

Related U.S. Application Data

(63) Continuation-in-part of application No. PCT/IL2012/050526, filed on Dec. 13, 2012, and a
(Continued)

(51) Int. Cl.
*A61B 5/1455* (2006.01)
*A61B 5/1459* (2006.01)
(Continued)

(52) U.S. Cl.
CPC ............ *A61B 5/1459* (2013.01); *A61B 1/041* (2013.01); *A61B 1/063* (2013.01); *A61B 5/0084* (2013.01); *A61B 5/073* (2013.01); *A61B 1/0684* (2013.01)

(58) Field of Classification Search
None
See application file for complete search history.

(56) References Cited

U.S. PATENT DOCUMENTS 4,567,148 A    1/1986  Schwartz
6,689,056 B1    2/2004  Kilcoyne et al.
(Continued)

FOREIGN PATENT DOCUMENTS

EP    2 127 592 A1    12/2009
JP    2011502555 A    1/2011
(Continued)

OTHER PUBLICATIONS

International Search Report for International Application No. PCT/IL2012/050526, dated May 10, 2013.
(Continued)

*Primary Examiner* — Eric Winakur
*Assistant Examiner* — Marjan Fardanesh
(74) *Attorney, Agent, or Firm* — Pearl Cohen Zedek Latzer Baratz LLP

(57) ABSTRACT

In-vivo devices, systems and methods for the detection of blood within in-vivo bodily fluids. The methods include irradiating in-vivo fluids passing through a gap in a housing of an in-vivo device introduced to the GI tract of a subject with a plurality of illumination sources positioned on a first side of a gap; detecting with at least one light detector positioned on the opposite side of the gap and facing the illumination sources, light irradiated by the illumination sources; transmitting a plurality of values representing the light detected over time; converting these values to blood concentration values over time, and comparing the blood concentration values to a predetermined threshold value. Based on the comparison, the method includes determining the type of bleeding profile, such that if a plurality of blood concentration values measured consecutively is above the threshold value, the bleeding profile indicates bleeding.

20 Claims, 48 Drawing Sheets

Related U.S. Application Data continuation-in-part of application No. PCT/IL2013/051073, filed on Dec. 26, 2013.

(60) Provisional application No. 61/576,091, filed on Dec. 15, 2011, provisional application No. 61/745,878, filed on Dec. 26, 2012.

(51) Int. Cl.
*A61B 5/00* (2006.01)
*A61B 5/07* (2006.01)
*A61B 1/04* (2006.01)
*A61B 1/06* (2006.01)

(56) References Cited

U.S. PATENT DOCUMENTS

| | | |
|---|---|---|
| 7,596,403 B2 | 9/2009 | Horn |
| 2003/0214579 A1 | 11/2003 | Iddan |
| 2004/0193029 A1 | 9/2004 | Glukhovsky |
| 2005/0148842 A1 | 7/2005 | Wang et al. |
| 2006/0036131 A1 | 2/2006 | Glukhovsky et al. |
| 2008/0033569 A1 | 2/2008 | Ferren et al. |
| 2008/0064923 A1 | 3/2008 | Rabinovitz et al. |
| 2008/0208077 A1 | 8/2008 | Iddan et al. |
| 2008/0234548 A1 | 9/2008 | Amit |
| 2009/0124874 A1 | 5/2009 | Gono et al. |
| 2010/0010312 A1 | 1/2010 | Gilad et al. |
| 2011/0306855 A1 | 12/2011 | Rabinovitz et al. |
| 2012/0136209 A1 | 5/2012 | Kostenich et al. |

FOREIGN PATENT DOCUMENTS

| | | |
|---|---|---|
| JP | 2011036371 A | 2/2011 |
| WO | WO 2009/061009 | 5/2009 |
| WO | WO 2010/086859 | 8/2010 |
| WO | WO 2010/086859 A1 | 8/2010 |
| WO | WO 2011/016002 | 2/2011 |

OTHER PUBLICATIONS

International Search Report for International Application No. PCT/IL2013/051073, dated Jun. 13, 2014.

Search report for European Patent Application No. 12858388.7, dated May 10, 2016.

Office Action for Japanese Patent Application No. 2014-546732, dated Sep. 20, 2016.

Office Action for Chinese Patent Application No. 201280063706.1, dated Oct. 19, 2016.

Office Action for Chinese Patent Application No. 201280063706.1, dated Apr. 5, 2016.

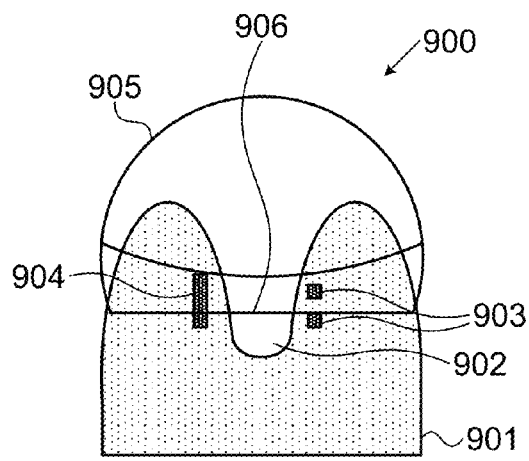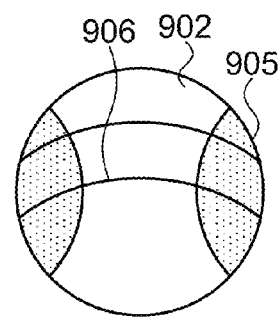
FIG. 13A    FIG. 13B
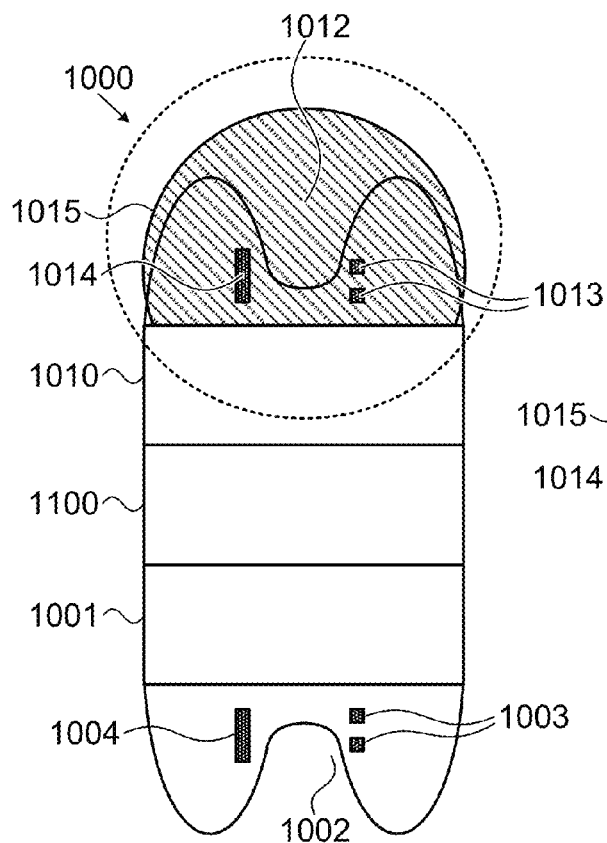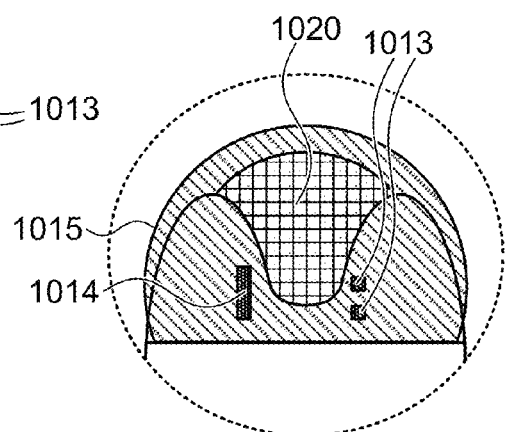
FIG. 14A    FIG. 14B

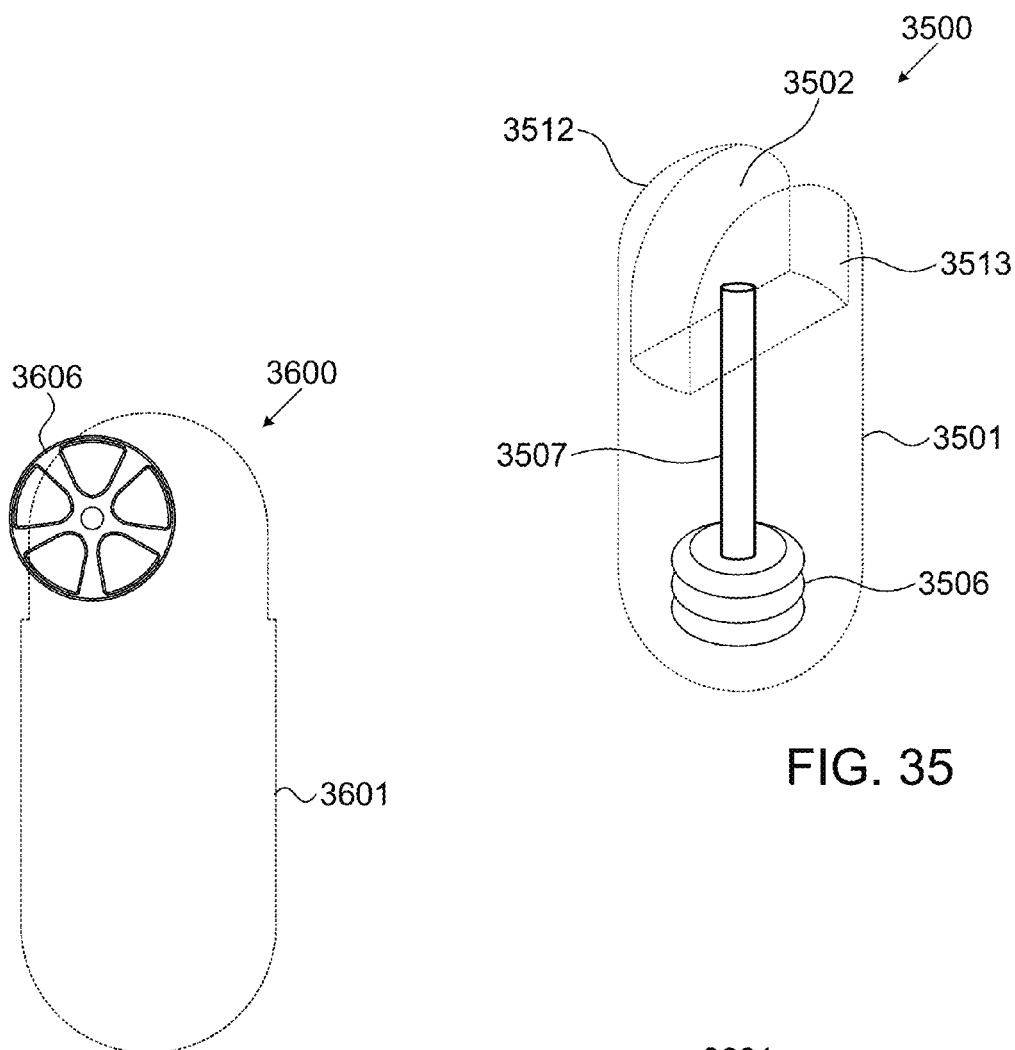
FIG. 35
FIG. 36A
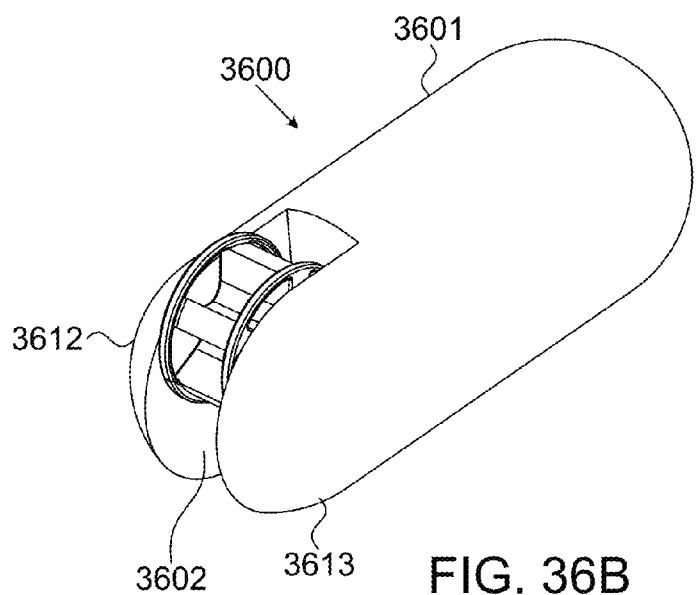
FIG. 36B

PRIOR-ART

FIG. 45A     FIG. 45B

DEVICE, SYSTEM AND METHOD FOR IN-VIVO DETECTION OF BLEEDING IN THE GASTROINTESTINAL TRACT

CROSS REFERENCE TO RELATED APPLICATIONS

This application is a continuation-in-part of PCT International Patent Application No. PCT/IL2012/050526, filed Dec. 13, 2012, which claimed priority from U.S. Provisional Patent Application No. 61/576,091, filed Dec. 15, 2011, and is also a continuation-in-part of PCT International Patent Application No. PCT/IL2013/051073, filed Dec. 26, 2013, which claimed priority from U.S. Provisional Patent Application No. 61/745,878, filed Dec. 26, 2012, all of which are hereby incorporated herein by reference.

FIELD OF THE INVENTION

This application relates to the field of in-vivo devices, systems, and methods of in-vivo detection. In particular, the present invention relates to devices, systems and methods for detection of blood in the gastrointestinal (GI) tract fluids.

BACKGROUND OF THE INVENTION

In-vivo bleeding may occur due to different diseases and in various locations along the gastrointestinal (GI) tract. This may indicate different pathologies present at those locations. For example, bleeding in the esophagus may be due to esophagitis or due to ruptures in varices. An ulcer in the stomach, small bowel or colon caused by inflammatory disease may be the source of bleeding. And, in the lower digestive tract, polyp or colorectal cancer may cause occult or overt bleeding. Therefore, early detection of bleeding and its anatomical location along the GI tract may be crucial for better treatment of many patients.

There are some known devices and methods, for detection of a bleeding source in the GI tract. For example, an endoscope or an imaging capsule endoscope may be used to search for and detect the source of an acute bleeding event in the GI tract. Such devices, however, may not be designed to efficiently detect the presence of small quantities of blood in the GI fluids. Other devices and methods may involve FOBT/FIT kits for detection of occult blood in the feces. However, while FOBT/FIT kits may detect bleeding that occurs in the colon, detection of bleeding in the small bowel or upper GI tract using FOBT kits is not efficient. Also, FOBT kits are not very patient friendly; patients are generally reluctant to perform such an examination.

PCT International Patent Application Publication No. WO 2010/086859, assigned to the common assignee of the present invention and incorporated herein by reference in its entirety, describes an in-vivo diagnostic device and method for detection of the presence of blood in GI fluids inside the GI tract. The in-vivo diagnostic device for detection of blood in the GI tract described therein comprises a special housing comprising a gap through which the in-vivo bodily fluids may flow. Illumination sources, such as LEDs, may reside on one side of the gap and may irradiate the bodily fluids passing through the gap. Each illumination source may irradiate the in-vivo fluids at a different narrow band illumination. At least one light detector may be positioned at the opposite side of the gap facing the illumination sources in order to detect light that passes through the in-vivo fluids. The device additionally comprises a transmitter for transmitting detected signals to an external receiver, which is a part of a system for the in-vivo detection of bleeding. The system also includes a processing unit for comparing the detected signals to a predetermined threshold, thereby determining the presence of blood in the GI tract.

However, the device described in the aforementioned PCT Application does not solve the problem of tissue entering the open gap. The tissue of portions of the GI tract, particularly—the small bowel, is collapsible, soft and covered with villi, and it snugly hugs the housing of the device as it progresses through the organ. The peristaltic motion of the organ pushes the tissue against the walls of the device and into the open gap. When tissue enters the gap, the tissue may block the passage of light from the illumination sources from reaching the light detector and may thus disrupt the operation of the device, for example, by leading to false readings of blood. Another deficiency is that the disclosed device does not address the problem of bubbles and content or non-fluid particles freely entering the gap, which may also disrupt the operation of the device, for example, by causing noise in the detected signals.

Furthermore, there are several other deficiencies in the aforementioned device disclosed in WO 2010/086859, for example a limited number of LEDs (preferably four) that does not allow differentiating between blood and other materials found in the bodily fluid of the GI tract, such as chlorophyll having the same absorption band between 600 nm and 700 nm as blood.

It has recently been found that there is also a problem of a relatively wide irradiation angle of LEDs located on the sensing head. In this case, light from such LEDs might strike objects (especially tissue) and change the reading in the photodiode.

It would be also beneficial to add temporal information to the system in order to identify active bleeding that occurred in the near past and to present a time line of the bleeding event. In other words, memory capability in the in-vivo diagnostic device and system are highly desirable.

There is, therefore, a need for improved devices, systems and methods for in-vivo detection of blood within in-vivo bodily fluids.

SUMMARY OF THE INVENTION

Embodiments of the present invention provide in-vivo devices, systems and methods for in-vivo detection of blood, specifically, detection of blood in the GI tract.

An in-vivo device according to an embodiment of the invention, for the detection of blood within in-vivo bodily fluids, may include an elongated housing, and a passage passing through the entire elongated housing, through which in-vivo bodily fluids enter and exit the device. The in-vivo device may further include an illumination source for illuminating the in-vivo bodily fluids. The illumination source may be located within the housing, behind a first side of the passage. The device may include a light detector for detecting light from the illumination source that passes through the in-vivo bodily fluids. The detector may be located within the housing, behind a second side of the passage, opposite the first side of the passage, such that the detector may be located opposite and facing the illumination source. Light emanating from the illumination source may pass through the in-vivo fluids and may reach the light detector, which may determine presence of blood based on the detected light signals.

According to some embodiments of the invention, the in-vivo device may be a swallowable device. In some embodiments, the housing may comprise rounded edges.

According to some embodiments, the device may comprise at least four illumination sources, each illuminating at a different narrow wavelength. In other embodiments, the device may comprise six illumination sources for illuminating at six different narrow wavelengths. The detector may be a photodiode.

According to some embodiments, the in-vivo device may comprise an internal power source. The device may further comprise a transmitter for transmitting the light detected by the detector.

In some embodiments, the illumination sources and the detector may be located at an equal distance from both ends/openings of the elongated housing, in order to prevent entrance of tissue into the sensing area. That is, the in-vivo device is designed such that the sensing area (in which the detector and illumination sources are located) is at an equal distance from both ends or openings of the device, such that, even if GI tissue does enter through either of the device's ends, or even through both ends, the tissue will not be able to reach the sensing area, and thus interference to the sensing area is avoided.

Following many experiments, it was concluded that the optimal diameter of the passage through which in-vivo fluids may flow and be detected for presence of blood or blood residues, may be between 3 to 5 mm. In certain embodiments, the diameter of the passage is no larger than 5 mm, since more than 5 mm would be a long optical path for light to pass and still maintain a significant intensity to enable detection and processing, and is no smaller than 3 mm since this would be a diameter too small to enable sufficient fluid flow. Experiments also showed that, for a passage with a diameter of between 3 to 5 mm, tissue might enter the passage for approximately 5 to 6 mm. Therefore, the sensing area should be located at a distance of at least 5 mm away from each end of the device.

In the stomach the fluids are relatively clear, such that it is relatively easy to detect presence of blood or blood related particles. However, in the small bowel, the fluids become cloudier and less clear, as the device passes along the small bowel towards the colon, and in the colon there are also solids flowing within the in-vivo fluids. Therefore, besides noise that may be caused by entrance of tissue into the sensing area, noise may also occur due to bubbles and feces or other particles unrelated to blood or blood residues that may enter the sensing area.

The present invention provides two types of devices; one device may be designed to detect presence of blood within the stomach and the small bowel. Such a device may further comprise an imager; therefore, this device may detect various types of pathologies through images taken by the imager, as well as detect presence of blood by using the blood sensing area. Such a device needs to detect presence of blood without the interference of tissue nor the interference of particles and bubbles flowing within the in-vivo fluids. Therefore, a device designed to detect presence of blood in the stomach and small bowel typically requires some kind of blockage or filtration of fluids prior to entrance of the fluids into the sensing area, in order to achieve a cleaner signal with less noise. Such a device may comprise an imager located at one end, and a blood sensing head located at another end the device.

Another device may be designed to detect presence of blood along the entire GI tract, from the esophagus, through the stomach and small bowel, and until the end of the colon. Since such a device is required to detect the presence of blood in the colon as well as in the stomach and small bowel, and since the colon contains solids flowing within the colon fluids, which solids may contain blood or blood residues, it is necessary to enable such solids to enter the sensing area and be sensed for presence of blood. Therefore, this type of device should be less strict about blockage and filtration of fluids before entering the sensing area, so as not to block entrance of solids into the sensing area. Such a device may include a passage passing along the longitudinal axis of the device's housing without any additional blocking or filtrating means located at the at least two openings of the device, in order to enable free passage for all kinds of particles through the sensing area. However, it is clear that, since no filtration of blockage is implemented as part of this device, a more sophisticated algorithm for analyzing the readings of the light detector, which may, for example, separate noise from true blood readings, is necessary.

In some embodiments, the passage passing through the in-vivo device may comprise a constricted section, i.e., a section with a diameter smaller than the diameter of the openings of the passage, thus creating Venturi effect. According to some embodiments, the device may further comprise a peristaltic pump located along the passage, at the section with decreased diameter of the passage. In some embodiments, the peristaltic pump may comprise a cylinder rotating around an eccentric axis of rotation, and a flexible film that is pushed by, and released from, the cylinder, periodically. The passage may be closed when the film is pushed by the cylinder, thus pushing fluids out of the in-vivo device, and the passage may be opened when the film is released from the cylinder, thus enabling entry of new fluids into the passage.

In some embodiments, the passage may be coated with a hydrophobic coating. The hydrophobic coating may be Parylene.

In some embodiments, the in-vivo device may include several measuring points or several sensing areas in order to decrease the effect of particles flowing through the passage. In some scenarios, particles flowing through the passage of the in-vivo device may interfere with detection of blood, since these particles may pass between the illumination sources and the light detector, thus interfering with passage of light from the illumination sources, through the fluids within the passage and towards the light detector. Therefore, if more than one sensing area is present within the in-vivo device, even if one of the sensing areas might be blocked by a flowing particle or particles, the other sensing areas may operate without any interference. In some embodiments, each of the sensing areas may include illumination sources located on one side of the passage, while a light detector is located on the opposite side of the passage. In other embodiments, a diffuser may be used as part of the illumination sources, such that light from the plurality of illumination sources may be diffused on a large area along the passage and be collected by a light detector or photodiode of a large area such to collect all the diffused light. In yet other embodiments, light channels may transfer light from the illumination sources to several points along the passage, and light channels may collect the light that passed through the fluids within the passage towards one light detector.

In some embodiments, the two ends of the passage may be covered with a membrane or filter with specific cut off and porosity that will not allow large particles and bubbles to penetrate the passage of the in-vivo device but still allow blood or blood residues to transfer through and into the passage. Although a membrane or filter may cause the blood or blood residues detection to take longer, since a membrane or filter cause fluid flow to be slower; lack of interfering particles passing through the sensing area may lead to a more quiet signal (less noise caused by particles) that may be measured by the sensing area, and thus the in-vivo device may allow detection with higher sensitivity.

A system according to an embodiment of the invention, for detection of blood within in-vivo bodily fluids, may include an in-vivo device comprising an elongated housing, a passage passing through the entire elongated housing, i.e., through the longitudinal axis of the device's housing, into which in-vivo bodily fluids enter and exit the device by way of the passage. In some embodiments, the passage may comprise a constricted section, i.e., a section with a diameter smaller than the diameter of the openings of the passage, thus creating Venturi effect. The device further includes an illumination source for illuminating the in-vivo bodily fluids. The illumination source may be located within the housing, behind a first side of the passage. The device further includes a detector for detecting light from the illumination source that passes through the in-vivo bodily fluids. The detector may be located within the housing, behind a second side of the passage, opposite the first side of the passage, such that the detector is located opposite and facing the illumination source. The illumination source and the detector may be located at an equal distance from both ends of the passage so as to avoid entrance of tissue into the sensing area defined by the illumination source and the detector. A transmitter for transmitting the light detected by the detector may also be included in the in-vivo device. The system may further include a receiver for receiving the transmitted light detected, a processor for processing the received light detected and determining presence of blood within the in-vivo fluids, and a display unit for displaying the processed light detected and the determination of presence of blood within the in-vivo bodily fluids.

An in-vivo device according to another embodiment of the invention may include a housing having a gap, which remains in contact with bodily fluids and through which the fluids pass when the device is in-vivo, and a sensing head. The sensing head may comprise illumination sources positioned on a first side of the gap, irradiating in-vivo bodily fluids that pass through the gap, and a light detector positioned on a second side of the gap opposite to the first side and facing the illumination sources, for detecting light from the illumination sources that passes through the in-vivo bodily fluids. The device may further comprise a driving mechanism comprising a motor, and a piston attached to the motor that is capable of being pushed and pulled by the motor. The piston passes in and out of the gap in order to suck in-vivo bodily fluids into the sensing head, and to eject the fluids out of the sensing head in a periodical manner. The device may further comprise a transmitter for transmitting the light detected by said detector. In some embodiments, the device may further comprise an internal power source.

An in-vivo device according to yet another embodiment of the invention may include a housing having a gap, which remains in contact with bodily fluids and through which the fluids pass when the device is in-vivo, and a sensing head. The sensing head may comprise illumination sources positioned on a first side of the gap, irradiating in-vivo bodily fluids that pass through the gap, and a light detector positioned on a second side of the gap opposite to the first side and facing the illumination sources, for detecting light from the illumination sources that passes through the in-vivo bodily fluids. The device may further comprise a flexible cover surrounding at least a portion of the housing. The cover may be able to hold fluids within it. The device may further comprise a piston bellows connected to the flexible cover, which the fluids may enter or exit from, and a piston attached to the piston bellows. The piston may pass in and out of the gap in order to suck in-vivo bodily fluids into the sensing head, and to eject the fluids out of the sensing head in a periodical manner. The device may further comprise a transmitter for transmitting the light detected by the detector.

According to some embodiments, the device may further comprise a pressure sensor. In some embodiments, the device may further comprise an internal power source. In some embodiments, the device may comprise an imager. In some embodiments, the device may further comprise two pH electrodes, such that each of the two electrodes may be located on a different side of the gap.

A method according to an embodiment of the invention may include the step of inserting an in-vivo device, according to any of the embodiments above, into the body lumen of a patient. The method may further include the steps of illuminating with illumination sources of different narrow band wavelengths, the in-vivo bodily fluids that pass through the gap or passage passing through the device, and detecting light from the illumination sources that passes through the in-vivo bodily fluids. The method may further include the steps of processing the detected light, and determining presence of blood within the in-vivo fluids. In some embodiments, the method may further include the step of displaying the processed light detections, and the determination of presence of blood within the in-vivo bodily fluids.

In a further embodiment, an in-vivo device may include a housing having a gap, which remains in contact with bodily fluids and through which the fluids pass when the device is in-vivo, and a sensing head. The sensing head may comprise illumination sources positioned on a first side of the gap, irradiating in-vivo bodily fluids that pass through the gap, and a light detector positioned on a second side of the gap opposite to the first side and facing the illumination sources, for detecting light from the illumination sources that passes through the in-vivo bodily fluids. The in-vivo device may comprise at least six illumination sources, e.g., LEDs, which may be positioned on one side of the gap, irradiating at different narrow band wavelengths, while at least one light detector photodiode may be positioned on the opposite side of the gap. The light detector photodiode is typically positioned such that it is facing the illuminating LEDs, while the gap is situated between the LEDs and the light detector photodiode. As the fluids pass through the gap, light irradiated by the LEDs passes through the bodily fluids and onto the light detector photodiode. Some of the light may be absorbed by the fluids, some may be scattered by insoluble particles, some may be reflected, and some may be transmitted to the light detector photodiode, which may then transmit signals, created in response to the detected light, to an external receiver.

A processor, external to the device, may process the signal sent by the light detector and create an absorption or transmittance spectra of the bodily fluids. By comparing the signals to a reference transmittance spectrum of other materials typically present in the GI tract, such as bile and chlorophyll, and to a reference transmittance spectrum of blood, it may be determined whether bile, blood, chlorophyll or all are present in the bodily fluids, and in what concentration, such that a conclusion may be made regarding presence of in-vivo pathologies.

In some embodiments, instead of comparing transmittance or absorbance spectra, a comparison between discrete signals detected by the light detector photodiode and a predetermined threshold may be made.

In yet a further embodiment, the sensing head of the in-vivo diagnostic device may include a specific blocker surrounding the illumination sources on one side of the gap thus reducing external reflection.

The internal components of the in-vivo diagnostic device may reside on a stepped printed circuit board (PCB). The PCB may optionally include one or more components, e.g., conductive rings. Other designs, components, elements, and structures may be used in addition to and/or in place of the rings, steps, etc. The PCB may further include contact points to connect additional components.

In yet a further embodiment, the PCB may include a sensor for sensing the current location of the device and an antenna typically associated with a transmitter for transmitting data from the device to an external system, which may determine the location of the device in a segment resolution. For example, the system may determine the location of the device along the GI tract segments, e.g., determine whether the device is in the esophagus, the stomach, the small bowel or the colon, based on the presence and/or concentration of bile. Other methods may be used to determine the location of the device in the different organs along the GI tract.

In some embodiments, other localization methods may be used for determining where the in-vivo device is located in-vivo along the GI tract. For example, the in-vivo device may include a pH detector which may be built into the sensing head and which may continuously detect pH levels of the body fluids inside the GI tract. This pH detector may comprise two electrodes and an electrical circuit, and may transmit the detected pH to a receiver that is external to the patient's body. Since, in different areas of the GI tract, there are different pH levels, the detected pH level may indicate the location of various pathological lesions in the GI tract. Thus, in a particular embodiment, the in-vivo diagnostic device may detect both the absorption or transmittance spectra and the pH level.

In another embodiment, the in-vivo diagnostic device may contain an imager in order to acquire in-vivo images of the pathological lesions where the bleeding may occur. The in-vivo device may also contain a power source, such as batteries.

In some embodiments, the in-vivo diagnostic device may additionally include therapeutic means. In this case, it would be desirable to have full control over the movement of such in-vivo diagnostic device including steering and maneuvering this device to a desired location and orientation of the device in the GI tract. This fully maneuverable in-vivo device may detect and immediately treat the bleeding lesions during its passage through the GI tract. The in-vivo diagnostic device may include a permanent magnet assembly for interacting with external magnetic fields for generating forces for steering the device. In addition, this in-vivo diagnostic device may include a multilayered imaging and sensing printed circuit board for sensing the current location and orientation of the in-vivo device, and for transmitting corresponding location and orientation data to an external system that generates the external magnetic fields.

In yet a further embodiment, a system of the invention may include the in-vivo diagnostic device, an external receiver/recorder able to receive data (e.g., absorbance or transmittance values) transmitted by the in-vivo device, and a computing platform or workstation able to store, process, display, or analyze the received data.

Some embodiments of the invention may include a method of in-vivo diagnostics. The method for detecting blood in-vivo may include the following steps:

a. swallowing the in-vivo diagnostic device of the present invention;
b. in-vivo repeatedly irradiating of the bodily fluids at different wavelengths as the device moves along the GI tract;
c. detecting over time the absorbance or transmittance signals or measuring absorbance or transmittance spectra of the in-vivo bodily fluids that pass through the sensing head of the device;
d. processing the absorbance or transmittance signals or spectra over time; and
e. displaying the processed absorbance or transmittance signals or transmittance spectra as a function of time.

The method may additionally include comparing the processed absorbance or transmittance signals or transmittance spectra with a predetermined threshold. The method may further include comparing the absorbance or transmittance spectra of the in-vivo bodily fluids to a predetermined absorbance or transmittance spectra of bile and chlorophyll and determining the presence and concentration of bile and chlorophyll in the bodily fluids.

The method may further include the step of determining concentration of blood in the bodily fluids over time, following the step of processing the detected absorbance or transmittance signals or spectra over time. In some embodiments, the method may include the step of displaying the processed absorbance or transmittance signals or spectra over time, following the step of processing the detected absorbance or transmittance signals or spectra over time. In some embodiments, displaying the processed absorbance or transmittance signals or spectra over time may include displaying concentration of blood over time. In other embodiments, the step of displaying may include displaying concentration of blood, alongside displaying a video of in-vivo images stream over time.

The method may further optionally include acquiring an in-vivo image or other data of the GI tract (other than absorbance or transmittance signals or spectra), such as pH, transmitting the acquired in vivo-image or other data, analyzing the in-vivo image or other data, and/or other suitable operations.

In some embodiments, in order to be able to display data related to bleeding profiles or bleeding events over time, the in-vivo diagnostic device or the external receiver should include a memory. The data collected over time by the sensing head (and, in some embodiments, the imaging data) may be stored in the memory unit located in the external receiver or in the in-vivo device. The stored data may then be processed and analyzed by, for example, a computing platform, which may be operatively associated with the receiver or the device. The processed data (e.g., blood concentration over time) may then be displayed to the physician so the physician could make a quick and precise diagnosis on patient condition.

In other embodiments, the external receiver may comprise a memory unit, a processing unit and a display, such that there is no need to transfer the collected data to an additional computing platform. In these embodiments the entire system may comprise the in-vivo diagnostic device and the external receiver alone, which may make it easier on a patient to undergo the majority, if not the entirety, of the procedure of blood detection in a home setting, instead of in a hospital setting.

Various embodiments of the invention may allow various benefits, and may be used in conjunction with various applications. The details of one or more embodiments are set forth in the accompanying figures and the description below.

Other features, objects and advantages of the described techniques will be apparent from the description and drawings and from the claims.

BRIEF DESCRIPTION OF THE DRAWINGS

The present invention will be understood and appreciated more fully from the following detailed description taken in conjunction with the appended drawings in which:

FIGS. 13A-B are schematic illustrations of a side-view cross-section and an upper-view of a section of an in-vivo device, in accordance with an embodiment of the invention, respectively;

FIGS. 14A-B are schematic illustrations of a side-view cross-section, and an enlargement of a section of an in-vivo device, in accordance with an embodiment of the invention;

FIGS. 15A-16B, are schematic illustrations of a side-view and a side-view cross-section, respectively, of an in-vivo device in accordance with an embodiment of the invention;

FIGS. 16A-16C, are schematic illustrations of a side-view, a side-view cross section and an enlargement of a section of a side view cross-section, respectively, of an in-vivo device in accordance with an embodiment of the invention;

FIG. 35 is a schematic illustration of a side view of an in-vivo device, in accordance with an embodiment of the invention;

FIGS. 36A-36B are schematic illustrations of side views of an in-vivo device, in accordance with an embodiment of the invention;

FIG. 45A is a perspective view of the printed circuit board assembly (face side), in accordance with embodiments of the present invention;

FIG. 45B is a perspective view of the printed circuit board assembly (back side), in accordance with embodiments of the present invention;

Figure 1A:
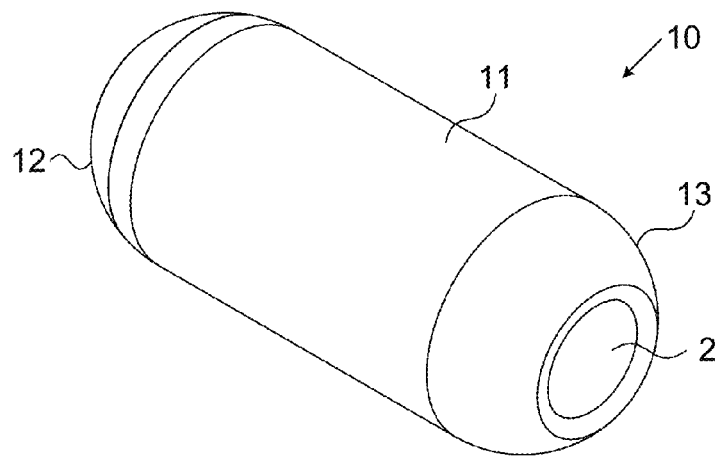
FIGS. 1A-1C are schematic illustrations of a side-view, a front-view and a front-view cross-section, respectively, of an in-vivo device for detection of blood within in-vivo fluids, in accordance with an embodiment of the invention.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to not obscure the present invention.

Figure 1B:
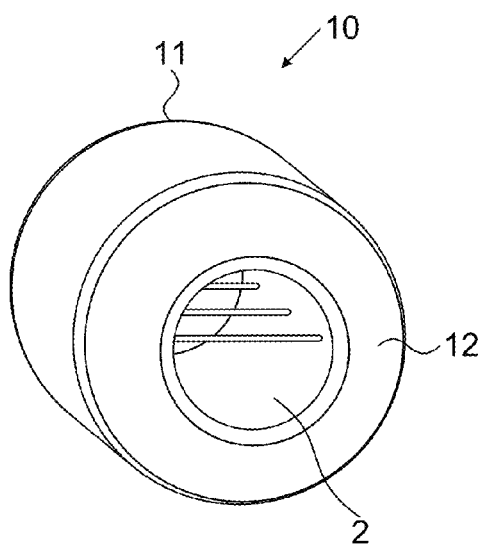
Figure 1C:
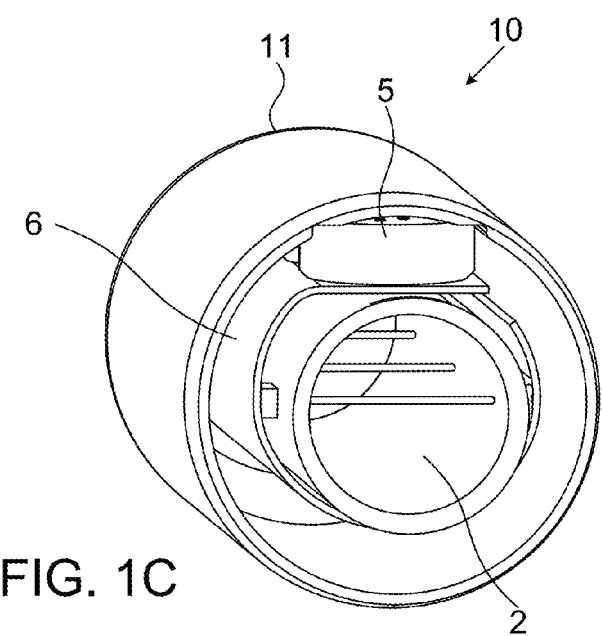

Reference is now made to FIGS. 1A-1C, which are schematic illustrations of a side-view, a front-view and a front-view cross-section, respectively, of an in-vivo device for detection of blood within in-vivo fluids, in accordance with an embodiment of the invention. As illustrated in FIG. 1A, device 10 may be an autonomous swallowable in-vivo device. Device 10 may comprise housing 11, which may have an elongated shape. Housing 11 may comprise a passage 2, which may pass through the longitudinal axis of housing 11. Passage 2 may begin at an opening at one end of housing 11, i.e., end 12, and may end at an opening at the opposite end of housing 11, i.e., end 13. Passage 2 passing through the longitudinal axis of housing 11 may create a tube-shaped device 10.

Figure 4:
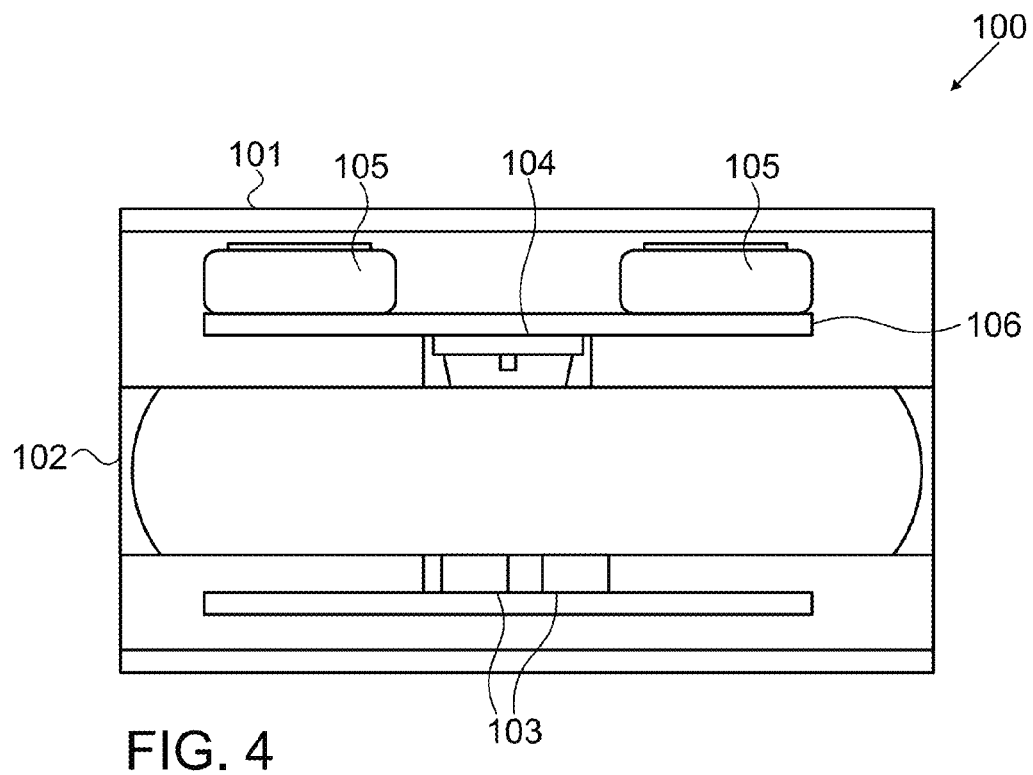
FIG. 4 is a schematic illustration of a top-view cross-section of an in-vivo device, in accordance with one embodiment of the invention.

FIG. 1B illustrates passage 2 having a constant diameter passing through the longitudinal axis of housing 11, from a first end/opening of housing 11 till the second opposite end/opening of housing 11, thus enabling fluid flow through passage 2. As illustrated in FIG. 4, passage 2 may comprise illumination sources (such as illumination sources 103, FIG. 4) and a light detector (such as detector 104, FIG. 4). The illumination sources may be a plurality of illumination sources, each illuminating the fluids passing within passage 2 at a different narrow wavelength. The light detector may detect the light signals after the light passed through the in-vivo fluids, which following processing may indicate presence of blood or blood residues.

In some embodiments, the illumination sources may be located behind one side of passage 2, while the light detector may be located behind the opposite side of passage 2, such that light emanating from the illumination sources may pass through the in-vivo fluids flowing within passage 2, and may then reach the light detector. Following many experiments, it was concluded that the optimal diameter of passage 2 through which in-vivo fluids may flow and be detected for presence of blood or blood residues, is between 3 to 5 mm. In one embodiment, the diameter of passage 2 is no larger than 5 mm, since more than 5 mm would be a long optical path for light to pass and while maintaining a significant intensity to enable detection and processing, and is no smaller than 3 mm since that would be a diameter too small to enable sufficient fluid flow. Experiments also showed that, for passage 2 with a diameter of between 3 to 5 mm, tissue might enter into passage 2 as far as 5 to 6 mm. Therefore, the sensing area, which is defined by the location of the illumination sources and the light detector, should be located at a distance of at least 5 mm away from each end of the device. Typically, the sensing area should be located at an equal distance of at least 5 mm from both ends of housing 11. In other embodiments, the distance of the sensing area from the ends of housing 11 need not be equal, though the distance between the sensing area and each of the ends should be larger than 5 mm.

FIG. 1C illustrates a cross-section of housing 11. Housing 11 may encapsulate PCB 6, onto which the electrical components, e.g., the illumination sources and the light detector may be disposed. PCB 6 may be wrapped around passage 2. Device 10 may comprise an internal power source, e.g., one or more batteries 5 may also be disposed onto PCB 6. Device 10 may further comprise a transmitter (not shown) and an antenna (not shown) for transmitting the signals collected by the light detector to an external processing device. Typically, the wall of passage 2, through which in-vivo fluids flow, may be transparent, so that light emanating from the illumination sources may pass through the wall of passage 2 and illuminate the flowing fluids, and so that light that passed through the flowing fluids may further pass through the transparent wall of passage 2, and be detected by the light detector.

In some embodiments, passage 2 may be coated with a hydrophobic coating. The hydrophobic coating may be Parylene. In some embodiments, device 10 may comprise a peristaltic pump located along passage 2 (as described in detail with respect to motor 314 and rotating cylinder 315, in FIG. 7A).

Figure 1D:
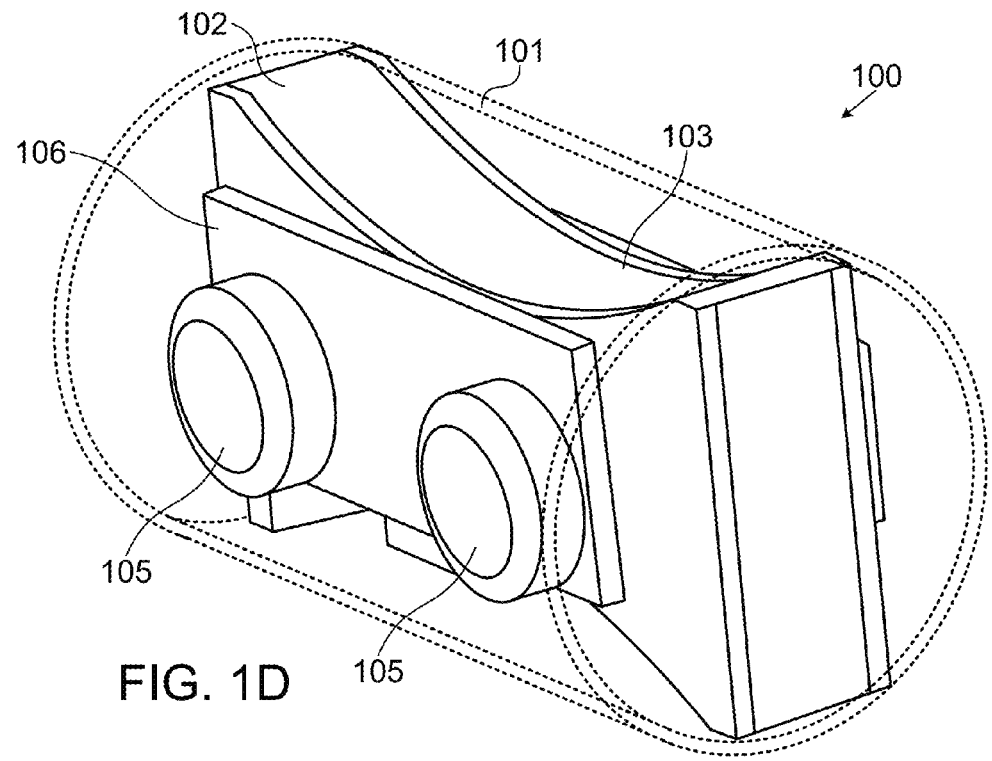
FIG. 1D is a schematic illustration of a perspective view of an in-vivo device for detection of blood within in-vivo fluids, in accordance with an embodiment of the invention.

Reference is now made to FIG. 1D, which is a schematic illustration of a perspective view of an in-vivo device in accordance with an embodiment of the invention. In-vivo device 100 may be an autonomous swallowable device. Device 100 may comprise housing 101, which may have an elongated shape. Housing 101 may comprise a passage 102, which may pass through the entire housing 101, from one end of housing 101 to the opposite end of housing 101, thereby creating a tube-shaped device. In-vivo bodily fluids may enter and exit device 100 through passage 102.

Device 100 may further comprise illumination sources 103, which may be more than one illumination source, e.g., between four to six illumination sources. In other embodiments, a different number of illumination sources may be part of device 100. Illumination sources 103 may each have a different narrow band wavelength. Illumination sources 103 may be positioned within housing 101, beside one side of passage 102 but facing towards passage 102. Typically, illumination sources 103 may be located behind a transparent plastic wall, which may form one side of passage 102 and separates illumination sources 103 from passage 102.

Device 100 may further comprise a light detector 104, e.g., a photodiode. Detector 104 may be located within housing 101, beside the second side of passage 102 but facing towards passage 102, opposite the first side of passage 102, such that detector 104 is located opposite and facing illumination sources 103. Typically, detector 104 may be located behind a transparent wall, which may form the second side of passage 102 and separates detector 104 from passage 102. Illumination sources 103 may illuminate in-vivo bodily fluids flowing through passage 102, and detector 104 may detect light from the illumination sources 103 that passes through the in-vivo bodily fluids.

The area where illumination sources 103 and detector 104 are located within housing 101 may be referred to as the optical area. The optical area is the area within the device where spectral analysis of light passing through the in-vivo bodily fluids is done, and, since this is accomplished by illumination sources 103 and detector 104, these components define the optical area. The operation of components in the optical area is done similarly to the operation of device 10 in FIG. 1 of PCT International Patent Application Publication No. WO 2010/086859, assigned to the common assignee of the present invention and incorporated herein by reference in its entirety.

Device 100 may comprise PCB 106, on which all electrical components of device 100 may be disposed, e.g., illumination sources 103 and detector 104. Additional electrical components may be disposed onto PCB 106, e.g., a transmitter (not shown). PCB 106 may typically be a rigid-flex PCB. Device 100 may further comprise an internal power source 105, e.g., batteries. Such batteries may be silver-oxide batteries, though any other type of batteries that may be used in-vivo may also be used to operate device 100.

According to some embodiments, device 100 may be a swallowable device. In order for device 100 to be comfortably inserted in-vivo, e.g., into the GI tract, by swallowing it, device 100 may comprise rounded edges, so it would easily slide through the mouth into the GI tract, and would easily pass along the GI tract without causing any harm to the walls of the lumen.

In some embodiments, the length of device 100 may be between 25 to 26 mm. The optical area may have a length of 13-14 mm, leaving 6 mm from each side of the optical area between the optical area and the edges of housing 101. These 6 mm should suffice to prevent tissue from entering the optical area of device 100, and thus prevent interruption or disruption to the optical area's readings. Even if tissue enters one or two of the openings of passage 102, those 6 mm from both sides of the optical area should suffice to keep the tissue away from the optical area. In some embodiments, the diameter of device 100 may be around 11 mm. These dimensions conform to dimensions of apparatuses that may be easily administered through a patient's mouth, either by self-swallowing or by insertion with a delivery device with the assistance of medical care personnel. In other embodiments, device 100 may have other dimensions.

In some embodiments, instead or in addition to the detection of blood, device 100 may be used to detect ammonia in order to indicate presence of *H. pylori*. Other biosensors may also be incorporated into device 100.

Figure 2:
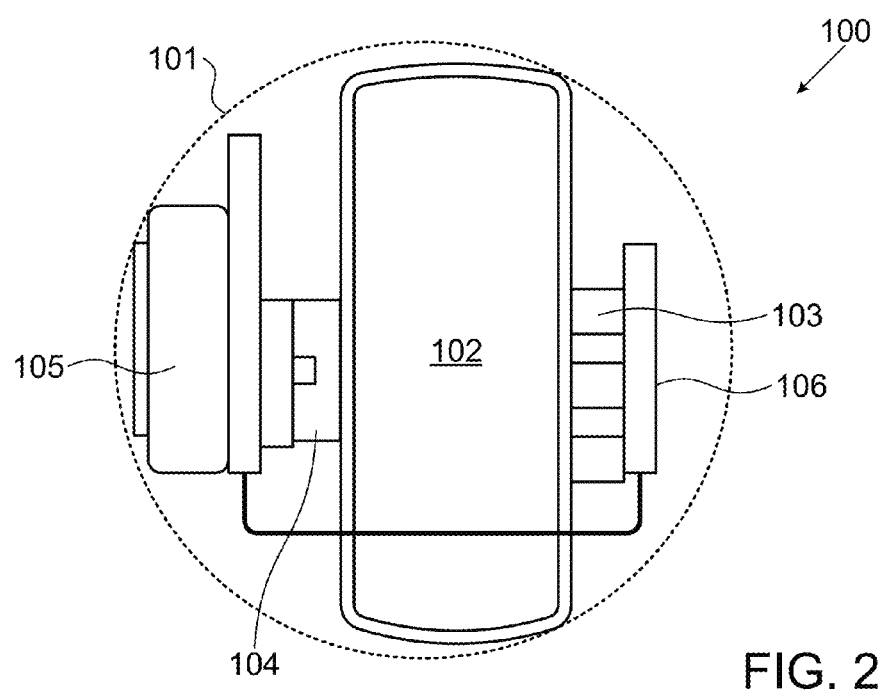
FIG. 2 is a schematic illustration of a front cross-section of an in-vivo device, in accordance with an embodiment of the invention.

Reference is now made to FIG. 2, which is a schematic illustration of a front cross-section of an in-vivo device, in accordance with an embodiment of the invention. FIG. 2 clearly shows the walls of passage 102 behind which illumination sources 103 and detector 104 are located. Illumination sources 103 are located opposite and facing detector 104, although behind the walls of passage 102. Passage 102 need not be located along the longitudinal axis of symmetry of device 100, since some space is needed for various electrical components, such as batteries 105.

Figure 3:
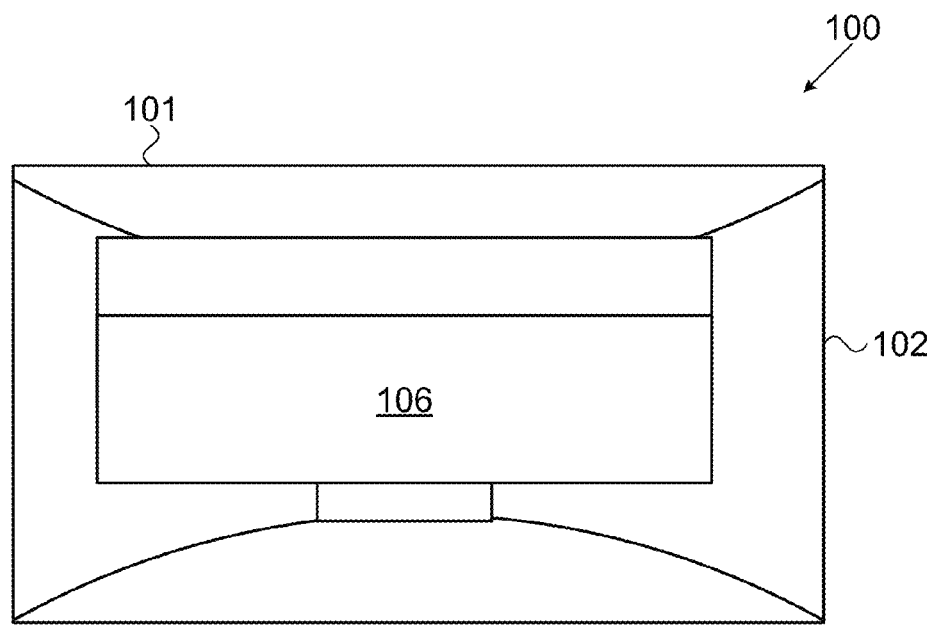
FIG. 3 is a schematic illustration of a side-view cross-section of an in-vivo device, in accordance with one embodiment of the present invention.

Reference is now made to FIG. 3, which is a schematic illustration of a side-view cross-section of an in-vivo device, in accordance with an embodiment of the present invention. Passage 102 is shown to pass along the entire length of housing 101. In some embodiments, passage 102 is symmetrical along the longitudinal axis as well as along the lateral axis. When passage 102 is symmetrical, even if some of the fluids flowing through passage 102 adhere to the walls of passage 102, due to high surface tension, there is still enough space for other fluids to pass through passage 102.

However, in other embodiments, passage 102 need not be symmetrical, as will be shown and explained with regard to FIG. 5 below.

Reference is now made to FIG. 4, which is a schematic illustration of a top-view cross-section of an in-vivo device, in accordance with an embodiment of the invention. FIG. 4 further illustrates that passage 102 is not necessarily located along the longitudinal axis of symmetry of device 100, but may be biased from the middle of device 100. In certain embodiments, passage 102 may not be located along the longitudinal axis of symmetry of device 100, such as when additional volume is needed in device 100 in order to enable insertion into device 100 of electrical components whose volume or size is larger than the volume that remains in device 100 alongside passage 102 when passage 102 passes along the longitudinal axis of symmetry of device 100. For example, some batteries 105 may have a relatively large volume or size that requires more space than what remains alongside passage 102 when passage 102 is aligned symmetrically along the longitudinal axis of symmetry of device 100; whereas such batteries 105 may not fit in device 100 when passage 102 is aligned symmetrically along the longitudinal axis of symmetry of device 100, such batteries 105 may be able to fit in device 100 if passage 102 is aligned asymmetrically along the longitudinal axis of symmetry of device 100.

Figure 5:
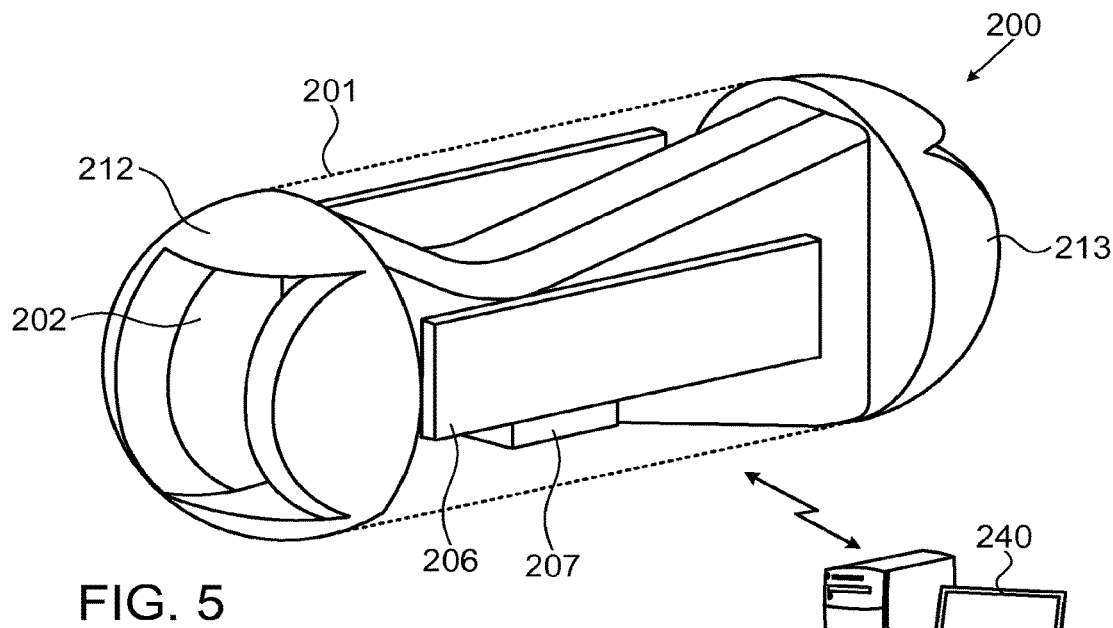
FIG. 5 is schematic illustration of a system including a side-view of an in-vivo device, in accordance with an embodiment of the invention.

Reference is now made to FIG. 5, which is a schematic illustration of a system including a side-view of an in-vivo device, in accordance with an embodiment of the invention. In-vivo device 200 may be a swallowable device, and may thus have a shape that enables ease of swallowing, e.g., cylindrical with rounded edges or ellipsoidal. Device 200 may comprise housing 201, which may have an elongated shape. Housing 201 may comprise passage 202, which may pass longitudinally through the entire housing 201 from one end of housing 201 to the opposite end of housing 201, thereby creating a tube-shaped device. Device 200 may be similar to device 100, since device 200 may also comprise an optical area located along the passage. The optical area, as in device 100, may comprise illumination sources (e.g., having different narrow band wavelengths) and a detector located one facing the other. However, device 200 may comprise a non-symmetrical passage 202. Passage 202 may be aligned symmetrically along the longitudinal axis of device 200, although it may also be aligned asymmetrically along the lateral axis of device 200.

According to the second embodiment of the invention, passage 202 may be shaped such to create 'Venturi effect'. Passage 202 may comprise one opening at each end of passage 202, although each of the two openings may be of a different diameter. A first opening 212 of passage 202 may be of a first diameter, then that diameter dramatically decreases as proceeding along passage 202 towards the second opening 213 of passage 202, until a certain point along passage 202, at which point the diameter of passage 202 may gradually increase as proceeding towards the second opening 213 of passage 202, although the diameter of passage 202 does not increase until reaching the same diameter as that of first opening 212, in order to maintain the asymmetry between openings 212 and 213, thus creating 'Venturi effect'. Venturi effect is created when fluids, which pass through the area of passage 202 that has a small diameter, are forced to pass through that area very quickly. This creates a decrease in pressure in that section of passage 202 of small or decreased diameter, which causes a semi-vacuum that may be used to suck more fluids into and through passage 202. That is, the special shape of passage 202 causes more bodily fluids to enter and pass through passage 202. Once fluids pass through passage 202, they may pass through the optical area within it, and be examined for presence of blood.

Device 200 may further comprise a PCB, which is typically rigid-flex. For example, the PCB of device 200 comprises rigid portion 206 and flex portion 207. All electrical components may be disposed onto the PCB, e.g., illumination sources, a detector, internal power source, and a transmitter (not shown).

FIG. 5 further illustrates a system according to a second embodiment of the invention. The readings collected by the detector, which is located within housing 201, are typically transmitted from device 200 to a receiver 220. Receiver 220 is typically located externally to device 200. Receiver 220 may comprise a memory unit, where the readings performed by the detector located within the optical area, may be saved. The system may further comprise a storage unit and a processor 230 for processing the readings or data collected by the detector, in order to determine presence of blood within the in-vivo bodily fluids. The system may also comprise a display unit 240 for displaying the raw and/or processed data for the ease of the physician, in order to assist the physician in providing his medical opinion on the status of the examined patient. Display unit 240 may further display the determination of presence of blood within the in-vivo bodily fluids, which determination was made by processor 230.

Figure 6:
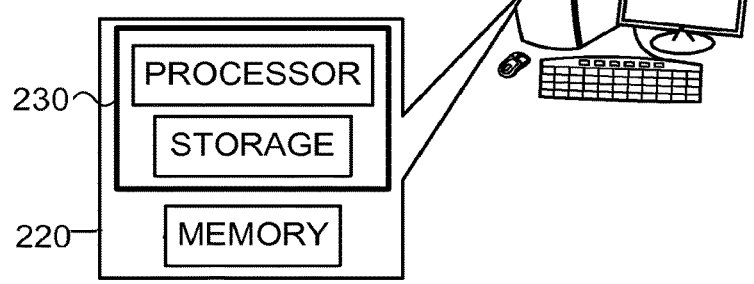
FIG. 6 is a schematic illustration of a side-view cross-section of an in-vivo device, in accordance with an embodiment of the invention.
Figure 6:
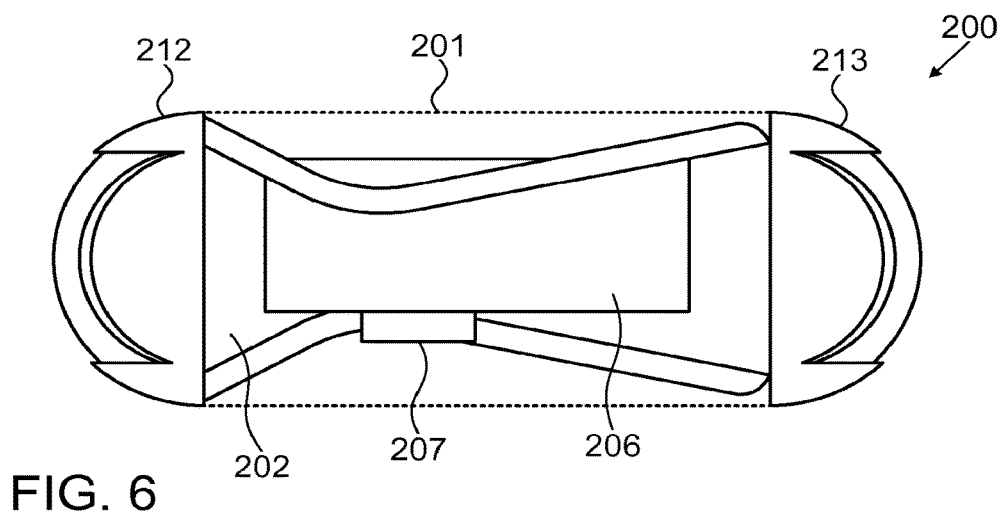

Reference is now made to FIG. 6, which is a schematic illustration of a side-view cross-section of an in-vivo device, in accordance with an embodiment of the invention. FIG. 6 clearly illustrates the asymmetry along passages 202 as well as between opening 212 and opening 213 of passage 202, which creates the 'Venturi effect' that causes fluids to be constantly sucked into passage 202 and pass through it.

Figure 7A:
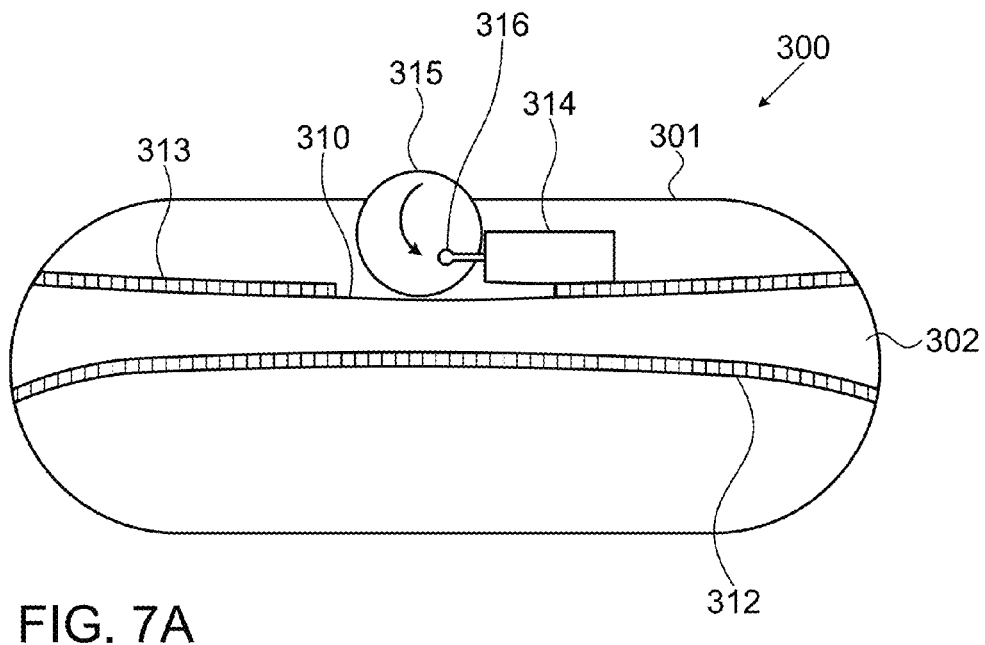
FIGS. 7A-7B are schematic illustrations of side-view cross-sections of an in-vivo device during two modes of operation, in accordance with an embodiment of the invention.
Figure 7B:
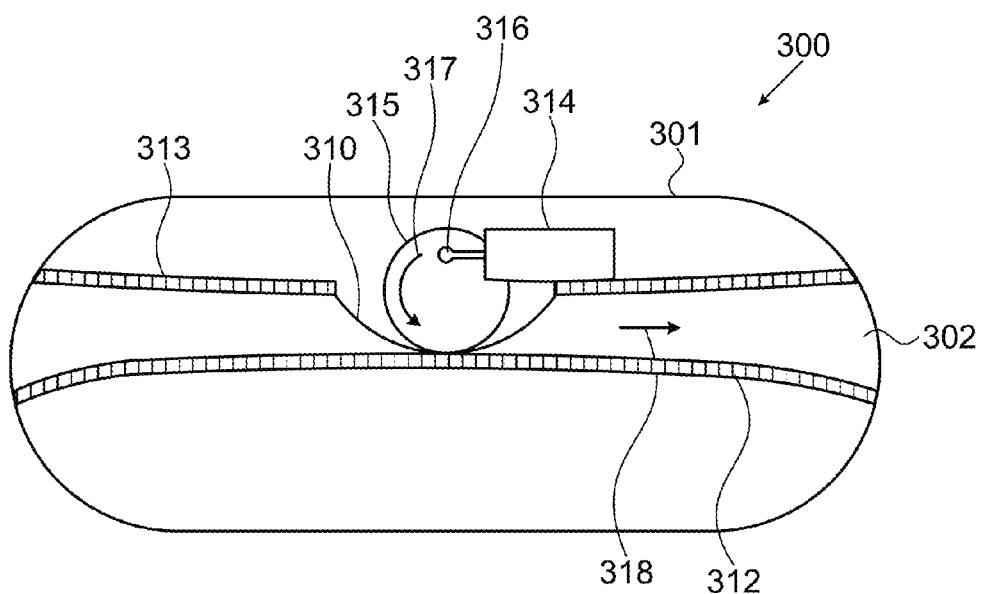

Reference is now made to FIGS. 7A-B, which are schematic illustrations of side-view cross-sections of an in-vivo device during two modes of operation, in accordance with an embodiment of the invention. In-vivo device 300 may be a swallowable device, and thus may have a shape that is easy to swallow, e.g., a sphere, a cylinder with rounded edges, or a capsule, though other shapes may be used instead. Device 300 may comprise housing 301, which may be elongated. Housing 301 may comprise passage 302, which may pass longitudinally through the entire housing 301. Housing 301 may comprise an optical area (not shown) located along passage 302, at a distance from either end of housing 301. Passage 302 may be similar to passage 202 shown in FIG. 2, i.e., passage 302 may be shaped to create 'Venturi effect'.

According to some embodiments, passage 302 may comprise two walls forming the shape of passage 302 along device 300. Passage 302 may comprise wall 312, which is made of a solid material, typically plastic, e.g., polycarbonate. Passage 302 may further comprise wall 313 located opposite wall 312. Wall 313 may be made of a solid material, but a section 310 of solid wall 313 may be a film made of a flexible material, for example, silicone, latex, rubber or any other flexible material. In some embodiments, flexible film 310 may be located in the area or section of passage 302, where passage 302 has the smallest (or most decreased) diameter or width, before the diameter of passage 302 increases again.

Device 300 may further comprise a motor 314, which may be connected to a cylinder 315 (shown in cross-sectional view), both of which are located inside housing 301. Cylinder 315 may be positioned between film 310 and the inside of housing 301, and may be in constant contact with film 310. Motor 314 causes cylinder 315 to rotate eccentrically around axis 316. As shown in FIG. 7A, before cylinder 315 begins to rotate around axis 316, it touches film 310 but does not apply any pressure onto it, since the part of cylinder 315 that is in initial contact with film 310 is the edge of cylinder 315 that is closest to axis 316, thus has the smallest thickness. However, once cylinder 315 starts to rotate, it begins to apply pressure onto film 310 thus pushing it towards wall 312. As illustrated in FIG. 7B, once cylinder 315 rotates around eccentric axis 316 (e.g., in the direction shown by arrow 317), the part of cylinder 315 that its edge is farthest from axis 316, i.e., the part of cylinder 315 with the largest thickness, pushes film 310 towards wall 312 until passage 302 is substantially closed. Since cylinder 315 continues to rotate around axis 316, the section of cylinder 315 of the smallest thickness would again be in contact with film 310, thus less pressure may be applied onto film 310 and passage 302 may be opened again for passage of fluids through it.

When cylinder 315 is positioned as shown in FIG. 7A, fluids may freely enter passage 302. However, when cylinder 315 is positioned as shown in FIG. 7B, then fluids that were within passage 302 are forcibly pushed outside of passage 302, e.g., in the direction shown by arrow 318. This forcible push of fluids outside of passage 302 by motor 314 and cylinder 315 may cause semi-suction of fluids into passage 302 once the cylinder rotates to its location as shown in FIG. 7A; where passage 302 is reopened for entrance of new fluids into passage 302. Motor 314 and rotating cylinder 315 act as a peristaltic pump that mimics peristaltic motion of the GI tract in order to enable better passage of fluids through passage 302.

Figure 8A:
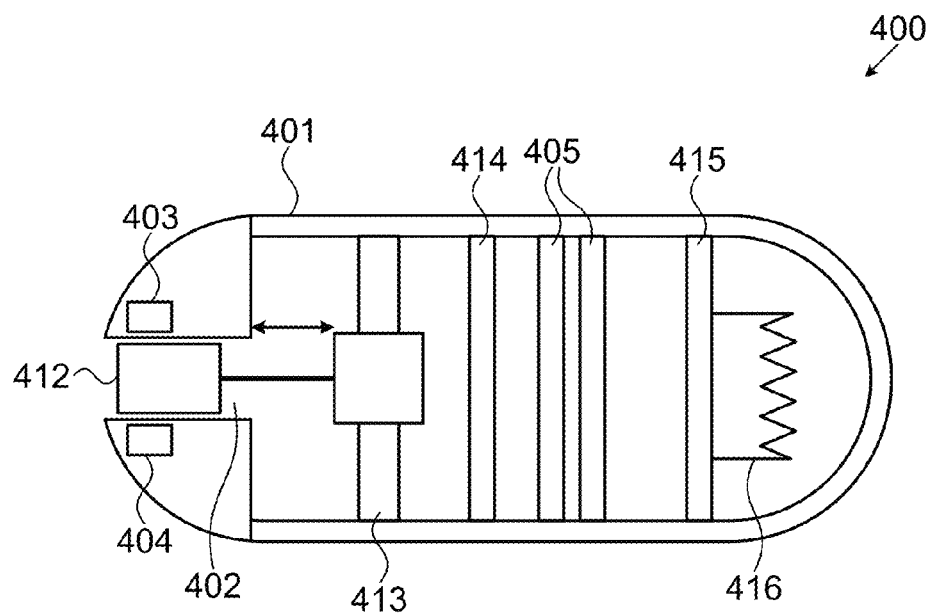
FIGS. 8A-C are schematic illustrations of side-view cross-sections of an in-vivo device, in accordance with an embodiment of the invention, before, during and after operation, respectively.
Figure 8B:
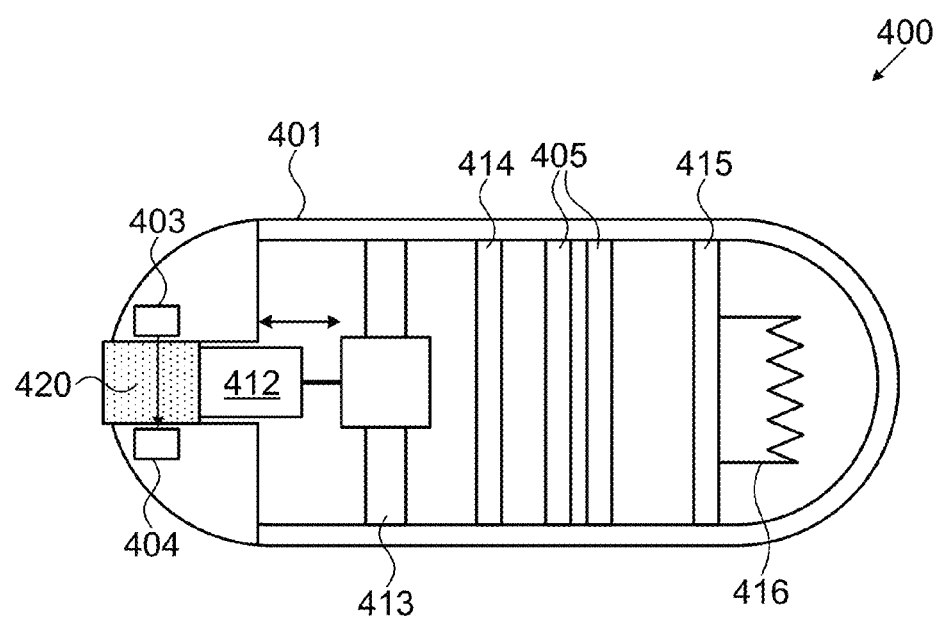
Figure 8C:
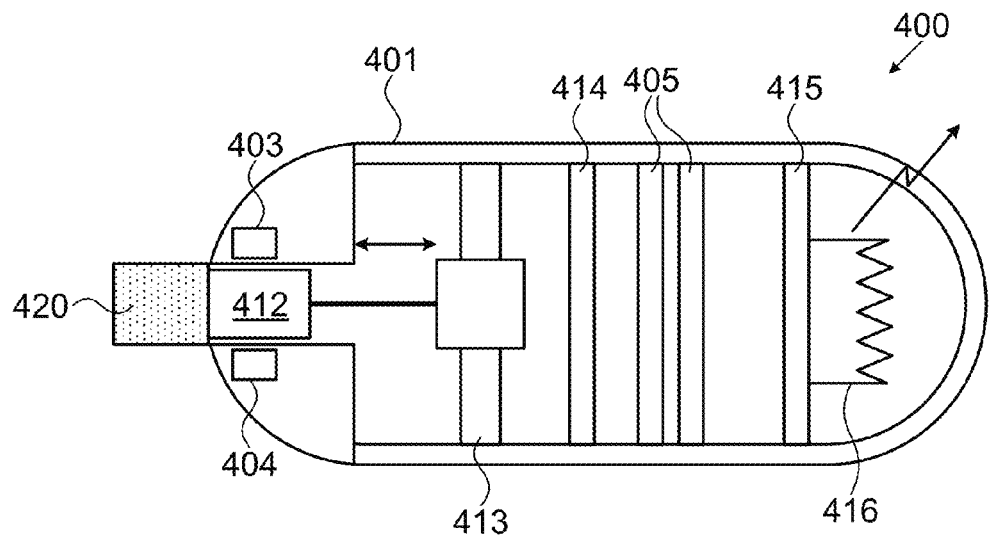

Reference is now made to FIGS. 8A-C, which are schematic illustrations of side-view cross-sections of an in-vivo device in accordance with an embodiment of the invention, before, during and after operation, respectively. In-vivo device 400 may be an autonomous swallowable device. Device 400 may comprise housing 401, which may typically be elongated in order to provide enough space for carrying various electrical components. Device 400 may comprise a gap 402 similar to the one disclosed in device 10 in FIG. 1 of PCT International Patent Application Publication No. WO 2010/086859. Gap 402 may enable entrance of bodily fluids in and out of it. On one side of gap 402 may be illumination sources 403 for irradiating in-vivo bodily fluids that pass through gap 402. On the opposite side of gap 402, and facing illumination sources 403, may be detector 404, for detecting light from illumination sources 403 that passes through the in-vivo bodily fluids. Gap 402, along with illumination sources 403 and detector 404 define the sensing head of device 400.

Device 400 may further comprise a driving mechanism 413, which may comprise an electrical motor. Driving mechanism 413 may be attached to piston 412. In some embodiments, piston 412 may be pushed and pulled by motor 413. When piston 412 is pulled and pushed by motor 413, piston 412 passes in and out of gap 402, respectively, in order to suck in-vivo bodily fluids into the sensing head, and to eject the fluids out of the sensing head, respectively, in a periodic manner. This way, new fluids continuously enter the sensing head in order to be examined for the presence of blood. Fluids that were already examined by the sensing head are released or ejected from the sensing head when motor 413 pushes piston 412 all the way through gap 402 until piston 412 substantially reaches the end of gap 402, which is substantially tangential to the end of housing 401.

Device 400 may further comprise transmitter 415 and antenna 416 for transmitting the data collected by detector 404. Device 400 may further comprise internal power source 405, e.g., batteries, and a processing unit 414. In other embodiments, processing unit 414 may be located in a different device externally to device 400.

FIG. 8A illustrates the location of piston 412 before motor 413 pulls it into device 400 through gap 402. FIG. 8B illustrates piston 412 during its way into housing 401, and while piston 402 is pulled inside housing 401, fluids (e.g., fluids 420) are sucked into gap 402 in order to be examined. FIG. 8C illustrates piston 412 after it has been pushed by motor 413 through gap 402 in order to push the fluids (e.g., fluids 420) that were examined by the sensing head, out of gap 402. Thus, gap 402 is now ready to suck new fluids into it in order to examine those new fluids for presence of blood.

Even if tissue is sucked into gap 402 instead of fluids, when piston 412 is pulled into the inside of housing 401, since motor 413 also pushes piston 412 towards the end of housing 401 (as shown in FIG. 8C), piston 412 may push the tissue out of device 400, and thus prepare device 400 to suck fluids into gap 402.

Figure 8D:
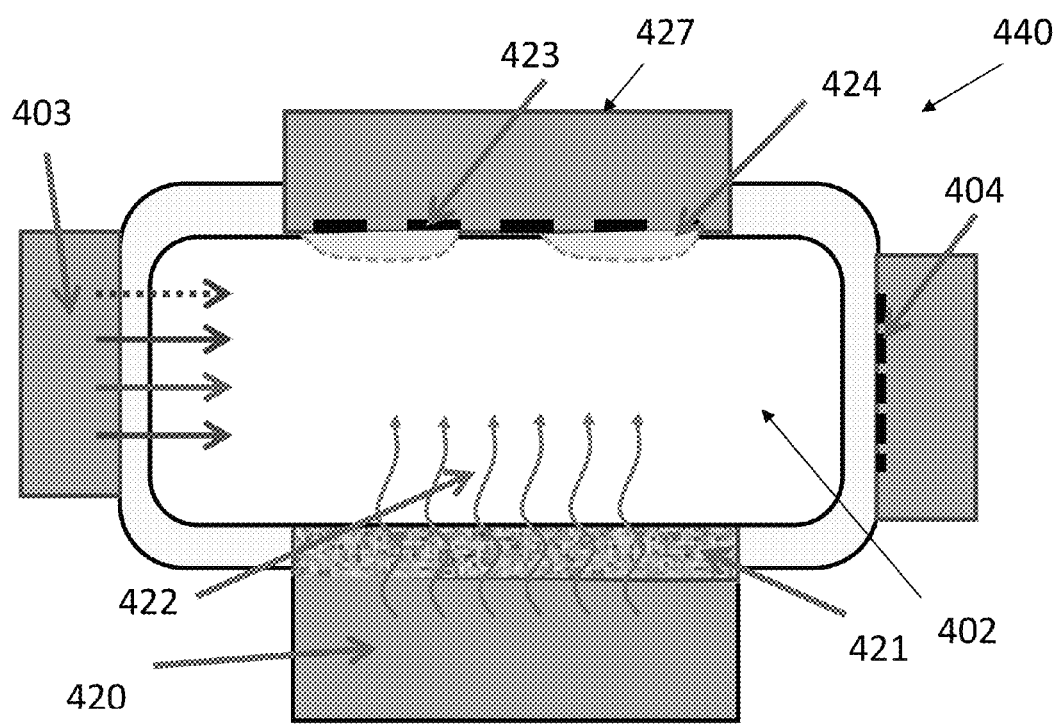
FIG. 8D is a schematic illustration of an upper-view cross section of a sensing head, in accordance with an embodiment of the invention.

Reference is now made to FIG. 8D, which illustrates an upper-view cross-section of a sensing head or sensing mechanism 440 that may be incorporated in a device similar to device 400 (FIGS. 8A-8C), in accordance with an embodiment of the invention. According to some embodiments, in addition to an electro-optical sensing setup, which comprises a plurality of illumination sources 403 (each irradiating light at a different narrow wavelength) and a light detector 404, sensing head 440 may further comprise an electro-chemical sensing setup, which may comprise reagents that are to be mixed and react with agents flowing within the in-vivo bodily fluids, and electrodes 423 that are to detect presence of such agents following reaction with the reagents that are added to the fluids. The agents that may be sought for may be either biomarkers for various pathologies, or may be particles related to blood. The reagents may either bind to such biomarkers/agents or they may cause the biomarkers/agents to undergo a reaction which may change one or more of their optical, electrical or chemical properties.

As will be described in detail with respect to FIGS. 8E-8G, the in-vivo device, e.g., device 400 may comprise a piston 412, which is moveable by a driving mechanism, e.g., motor 413. The movement of piston 412 forward and backward along gap 402 may cause in-vivo fluids to exit from gap 402, and may then cause new in-vivo fluids to enter into gap 402, respectively. While the fluids are being optically detected for presence of blood by detector 404 detecting light that is irradiated from illumination sources 403 and which passes through the in-vivo fluids, additional sensing may take place. In some embodiments, a container 419 may comprise reagents 422 that are to react with biomarkers/agents flowing within in-vivo bodily fluids may be located on an axis perpendicular to the axis along which illumination source 403 and light detector 404 are located. A porous wall 421 may be located between container 419 and gap 402, such that reagents 422 may move from container 419 into gap 402 by, for example, means of diffusion. Once reagents 422 enter gap 402 while in-vivo fluids are also present within gap 402, a reaction may occur between reagents 422 and biomarkers or other agents that may be flowing within the in-vivo bodily fluids. The reaction may be a change in an optical property of the biomarker/agent or of the reagent, for example, a change in color. In such case, sensing unit 427 that may be located across container 419 (along the same axis that container 419 is located, which is typically perpendicular to the axis along which illumination sources 403 and light detector 404 are located) may comprise an optical sensing unit that may detect a change in color. In other embodiments, the reaction may cause a different change, for example, a change in conductivity of the fluids due to a reaction that creates presence of electrolytes. In order to detect a change in conductivity, sensing unit 427 may, for example, comprise electrodes 423 on a chip. Current may be measured between two close electrodes, thus determining change in conductivity of the fluids. In some embodiment, in order to increase specificity, selective membrane 424 may cover electrodes 423, such to limit entry to specific particles and to detect electrical properties of those particles alone. In some embodiments, selective membrane 424 may be located over any other type of sensing unit that is to detect presence of biomarkers or other agents. For example, selective membrane 424 may cover a sensing unit that is to detect an optical change, though other sensing units may be incorporated as part of sensing mechanism 440.

Figure 8E:
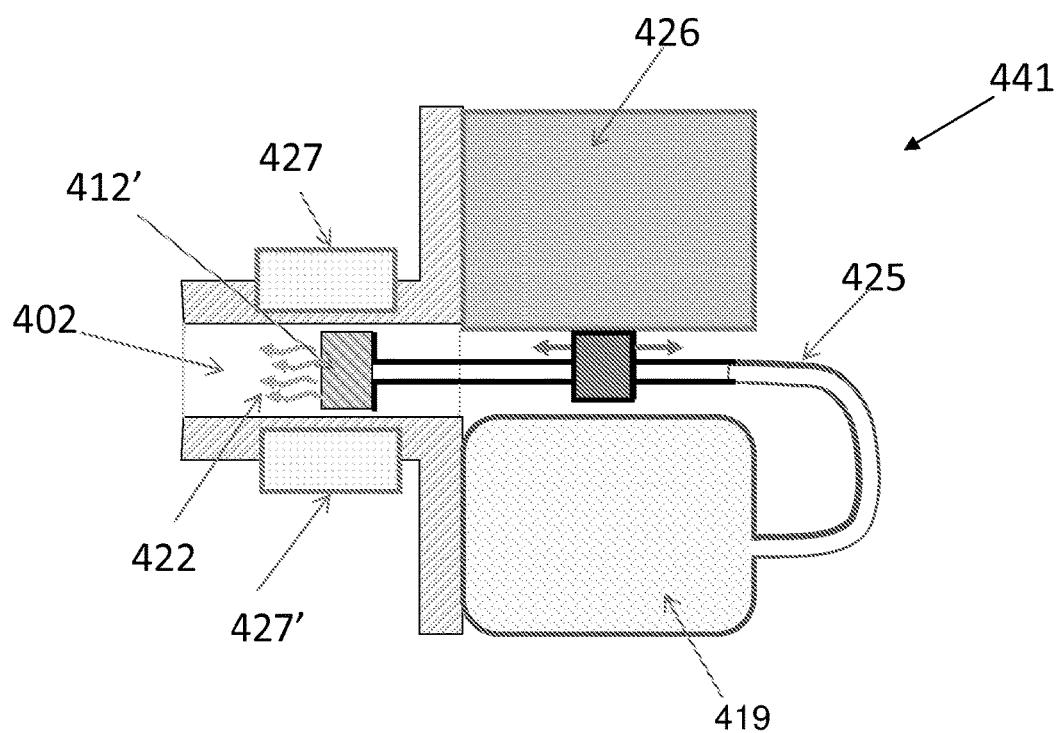
FIG. 8E is a schematic illustration of a side-view cross-section of a sensing mechanism, in accordance with an embodiment of the invention.

Reference is now made to FIG. 8E, which schematically illustrates a side-view cross-section of a sensing mechanism in accordance with an embodiment of the invention. Sensing mechanism 441 may be incorporated in an in-vivo device similar to device 400 (FIGS. 8A-8C). Mechanism 441 may comprise a driving mechanism 426, e.g., a motor, which may be connected to piston 412' and may move it forward and backward along gap 402, thus pushing fluids out of gap 402 and sucking new fluids into gap 402, respectively. Mechanism 440 may further comprise a container 419 of reagents, which may contain one or more types of reagents that are intended to react with one or more types of biomarkers or other particles that may be flowing within the in-vivo bodily fluids and may indicate on presence of pathologies or presence of blood. Mechanism 441 may further comprise tube 425 through which reagents 422 may pass from container 419 towards piston 412'. In some embodiments, piston 412' may be porous piston, i.e., piston 412' may comprise pores or holes through which reagents 422 may be oozing out into gap 402. Reagents 422 may then mix and react with the in-vivo fluids that are also within gap 402.

Once driving mechanism 426 pushed piston 412' forward, towards the proximal end of gap 402, in-vivo fluids are pushed outside of gap 402. However, when driving mechanism 426 pulls piston 412' backwards, towards the distal end of gap 402, new fluids are sucked into gap 402. While piston 412' is pulled towards the distal end of gap 402, thus causing new in-vivo fluids to be sucked into gap 402, reagents 422 may be oozing from the pores in piston 412', and may thus be mixed with the in-vivo fluids now entering gap 402. Since, during the entry of new in-vivo fluids into gap 402, reagents 422 simultaneously enter gap 402 (through the pores in piston 412'), the reagents are forced to mix with the in-vivo fluids, and may thus react with biomarkers or other particles if present within the in-vivo fluids that have entered into gap 402.

Sensing mechanism 441 may further comprise sensing units 427 and/or 427' that may sense a change in properties of the fluids following a reaction between reagents 422 and the biomarkers/agents present within the in-vivo fluids. In some embodiments, each of sensing units 427 and 427' may be designed to detect a different change in a different property of the fluids, biomarkers, agents or reagents. In other embodiments, sensing units 427 and 427' may be designed to detect the same change, thus increasing the signal to noise ratio that may be detected following the change, since both sensing units 427 and 427' may detect the same change from different angles of gap 402. In yet further embodiments, sensing units 427 and 427' may each be designed to detect a different change caused by a different reaction between different types of biomarkers, agents or reagents. In some embodiments there may be only one sensing unit 427, through in other embodiments there may be more than one sensing unit. Sensing units 427 and 427' may be located on an axis that is perpendicular to the axis along which illumination sources 403 and light detector 404 are located, thus enabling both electro-optical sensing of the in-vivo fluids present within gap 402, as well as electro-chemical sensing of the fluids. In other embodiments, device 400 may comprise sensing units 427 and 427' only, without illumination sources 403 and light detector 404, thus only sensing electro-chemical properties without electro-optical sensing.

Figure 8F:
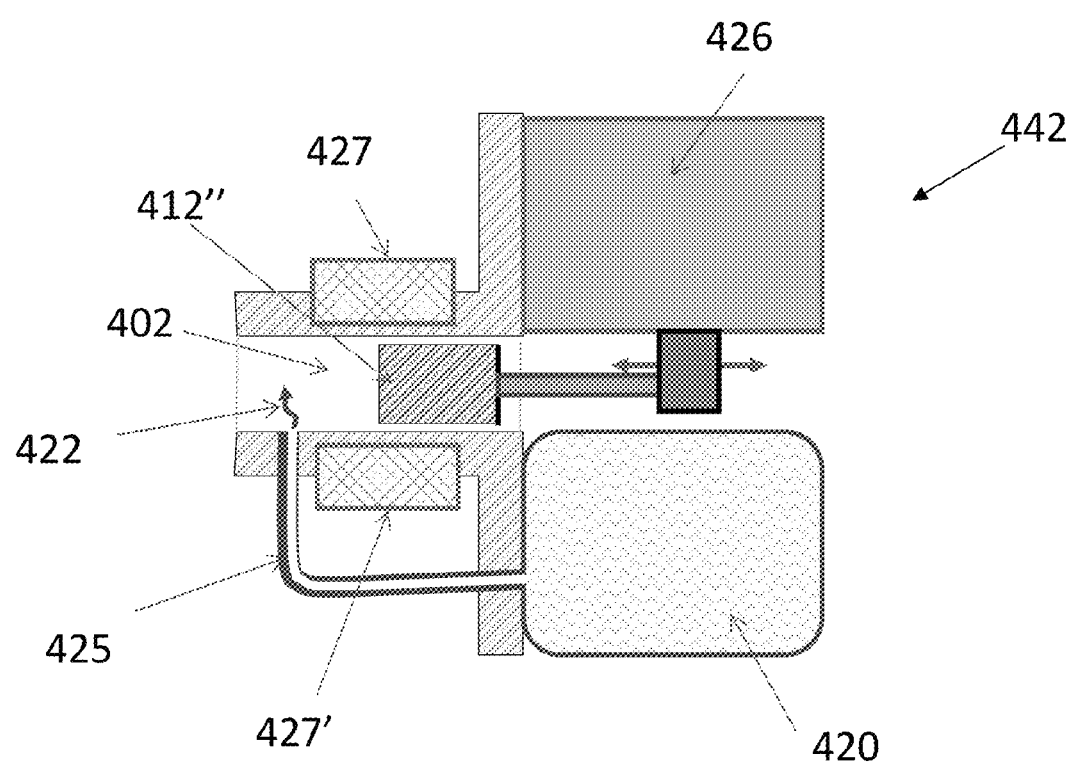
FIG. 8F is a schematic illustration of a side-view cross-section of a sensing mechanism, in accordance with an embodiment of the invention.

Reference is now made to FIG. 8F, which schematically illustrates a side-view cross-section of a sensing mechanism in accordance with an embodiment of the invention. Sensing mechanism 442 may be incorporated in an in-vivo device similar to device 400 (FIGS. 8A-8C). Sensing mechanism 442 may comprise a driving mechanism 426, e.g., a motor, which may be connected to piston 412" and may move it forward and backward along gap 402, thus pushing fluids out of gap 402 and sucking new fluids into gap 402, respectively. Mechanism 442 may further comprise a container 420, which may contain one or more types of reagents 422 that are intended to react with one or more types of biomarkers or other particles that may be flowing within the in-vivo bodily fluids and may indicate on presence of pathologies or presence of blood. Mechanism 442 may further comprise tube 425 through which reagents 422 may pass from container 420 towards gap 402. The movement of piston 412" forward and backward along gap 402 may cause in-vivo fluids to exit and enter gap 402, respectively, while also causing reagents 422 to be oozing out of tube 425 and to mix with the new in-vivo fluids that are sucked into gap 402 (when piston 412" is pulled backward, towards the distal end of gap 402).

Sensing mechanism 442 may further comprise sensing units 427 and/or 427' that may sense a change in properties of the fluids following a reaction between the reagents and the biomarkers/agents present within the in-vivo fluids. In some embodiments, each of sensing units 427 and 427' may be designed to detect a different change in a different property of the fluids, biomarkers, agents or reagents. In other embodiments, sensing units 427 and 427' may be designed to detect the same change, thus increasing the signal to noise ratio that may be detected following the change, since both sensing units 427 and 427' may detect the same change from different angles of gap 402. In yet further embodiments, sensing units 427 and 427' may each be designed to detect a different change caused by a different reaction between different types of biomarkers, agents or reagents. In some embodiments there may be only one sensing unit 427, through in other embodiments there may be more than one sensing unit. Sensing units 427 and 427' may be located on an axis that is perpendicular to the axis along which illumination sources 403 and light detector 404 are located, thus enabling both electro-optical sensing of the in-vivo fluids present within gap 402, as well as electro-chemical sensing. In other embodiments, device 400 may comprise sensing units 427 and 427' only without illumination sources 403 and light detector 404, thus only enabling electro-chemical sensing without electro-optical sensing.

Figure 8G:
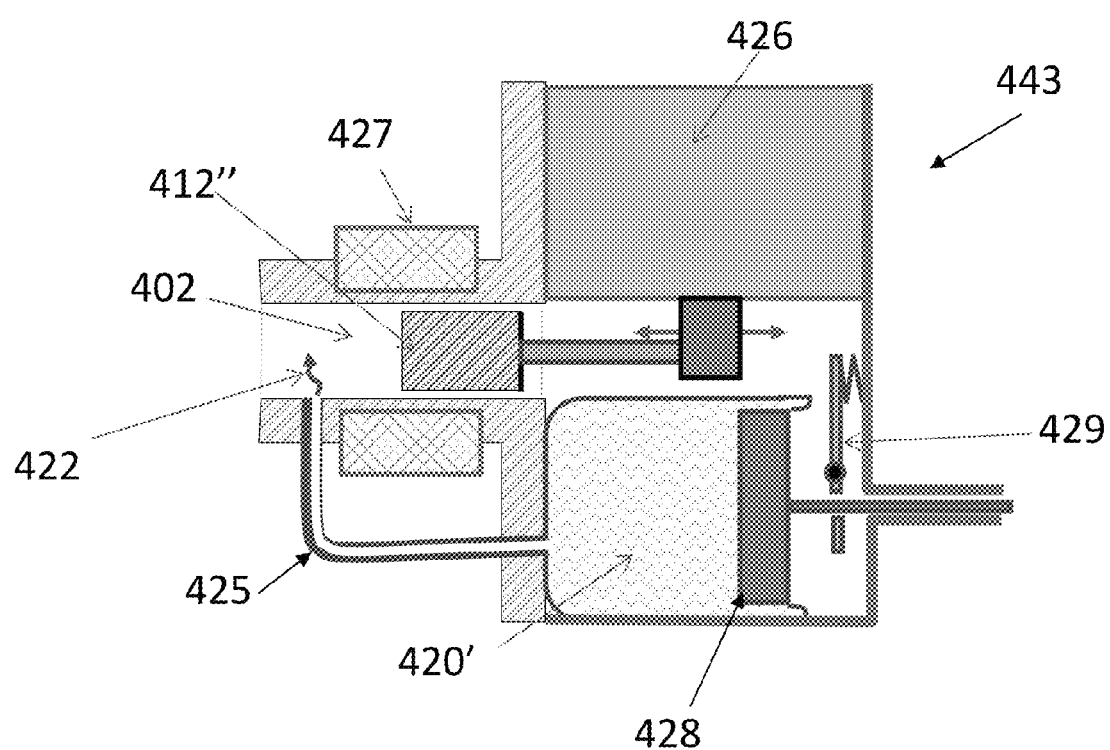
FIG. 8G is a schematic illustration of a side-view cross-section of a sensing mechanism, in accordance with an embodiment of the invention.

Reference is now made to FIG. 8G, which schematically illustrates a side-view cross-section of a sensing mechanism in accordance with an embodiment of the invention. Sensing mechanism 443 may be incorporated in an in-vivo device similar to device 400 (FIGS. 8A-8C). Sensing mechanism 443 may comprise a driving mechanism 426, e.g., a motor, which may be connected to piston 412" and may move it forwards and backwards along gap 402, thus pushing fluids out of gap 402 and sucking new fluids into gap 402, respectively. Sensing mechanism 443 may further comprise a container of reagents 420, which may contain one or more types of reagents that are intended to react with one or more types of biomarkers or other particles that may be flowing within the in-vivo bodily fluids and may indicate on presence of pathologies or presence of blood.

Sensing mechanism 443 may further comprise tube 425 through which the reagents 422 may pass from container 420 towards gap 402. The movement of piston 412" forward and backward along gap 402 may cause in-vivo fluids to exit and enter gap 402, respectively, while also causing reagents 422 to exit out of tube 425 and to mix with the new in-vivo fluids that are sucked into gap 402 (when piston 412" is pulled backward towards the distal end of gap 402). In some embodiments, container 420 may be made of a flexible material such that it may be pushed and squeezed by piston 428, which may actively cause reagents 422 to be pushed out of container 420 through tube 425 and into gap 402. According to some embodiments, piston 428 may be pushed forward, towards container 420 when piston 412" is pulled backward along gap 402, towards the distal end of gap 402. In some embodiments, sensing mechanism 443 may comprise a clamp 429 that may hold piston 428 in constant position not enabling piston 428 to move. Once driving mechanism 426 pulls piston 412" backward, towards the distal end of gap 402, (thus causing new in-vivo fluids to enter gap 402), piston 412" pushes clamp 429, which then releases piston 428 from the grasp of clamp 429. Once piston 428 is released from clamp 429, piston 428 may be pushed against flexible container 420, thus causing reagents 422 to be pushed through tube 425 and into gap 402. That is, in one pulling operation of driving mechanism 426, new in-vivo fluids are forced to enter into gap 402 (new fluids are sucked into gap 402 since piston 412" is pulled backward by driving mechanism 426, towards the distal end of gap 402), and reagents 422 may be actively pushed from container 420, through tube 425 and into gap 402, thus being mixed with the in-vivo fluids to create a reaction between reagents 422 and biomarkers or other sought for substances that may be present within the in-vivo fluids. Following the pulling motion, when driving mechanism 426 pushes piston 412" forward, towards the proximal end of gap 402, piston 412" no longer pushes clamp 429, thus enabling clamp 429 to return to its grasping or holding position of piston 428. When piston 428 no longer pushes against container 420, reagents 422 stop being pushed out of container 420 towards gap 402. Once the pulling motion ends, driving mechanism 426 may again push piston 412" forward, towards the proximal end of gap 402, and so on; the pulling and pushing motion of piston 412" by driving mechanism 426 may continue repeatedly.

Examples of various mechanisms of the entry of reagents 422 into gap 402, and the mixing of reagents 422 with in-vivo fluids inside of gap 402 are discussed in FIGS. 8D-8G above. Sensing mechanism 440 may enable entrance of reagents 422 into gap 402 through porous wall 421, mechanism 441 may enable entrance of reagents 422 into gap 402 through porous piston 412', mechanism 442 may enable direct entrance of reagents 422 into gap 402 through tube 425, and mechanism 443 may enable active entry of reagents 422 into gap 402 by forcedly pushing reagents 422 into gap 402. However, it is clear that these mechanisms are examples, and other mechanisms may also be used to facilitate entry of reagents into the sensing area in gap 402, and their mixing with in-vivo fluids present within gap 402.

Figure 9:
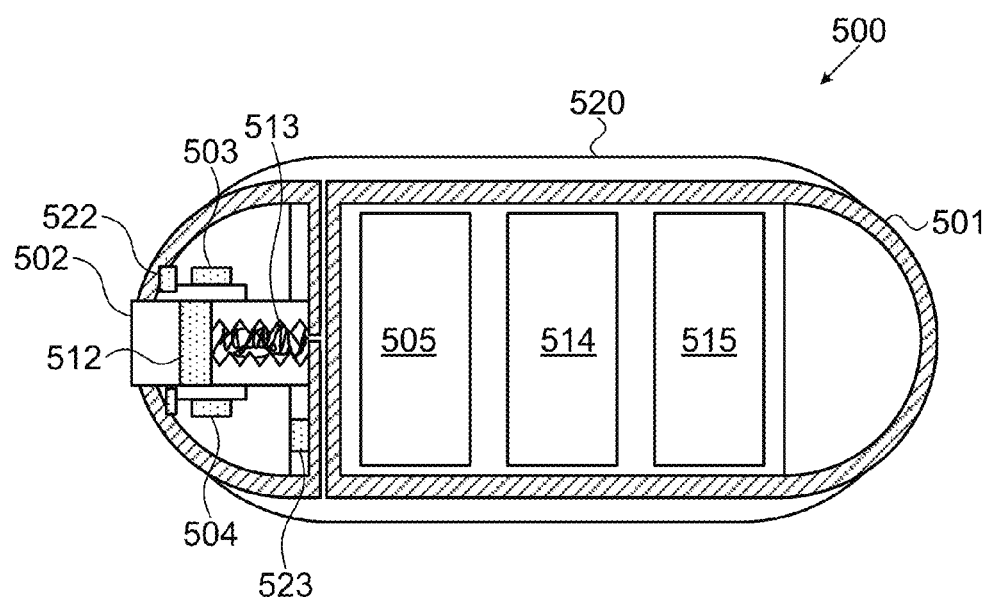
FIG. 9 is a schematic illustration of a side-view cross-section of an in-vivo device, in accordance with an embodiment of the invention.

Reference is now made to FIG. 9, which is a schematic illustration of a side-view cross-section of an in-vivo device in accordance with an embodiment of the invention. In-vivo device 500 may be a swallowable autonomous device. Device 500 may comprise housing or shell 501, which may be elongated in order to provide enough space for carrying various electrical components. Housing 501 may comprise a gap 502 that may enable entrance and exit of bodily fluids in and out of gap 502. On one side of gap 502 there may be illumination sources 503 for illuminating bodily fluids that enter gap 502 with different narrow band wavelengths. On the opposite side of gap 502, facing illumination sources 503, there may be detector 504. Detector 504 may detect light from illumination sources 503 after the light passed through the bodily fluids. Gap 502, along with illumination sources 503 and detector 504, defines the sensing head of device 500.

Device 500 may further comprise a flexible cover 520 surrounding at least a portion of the external surface of housing 501. Flexible cover 520 may be able to hold fluids within it. Flexible cover 520 may change its shape once pressure is applied onto it, either from the inside of the cover or from the outside. Flexible cover 520 may be connected to a piston bellows 513 such as to allow flow of fluids from flexible cover 520 to piston bellows 513, and vice versa. According to some embodiments, piston bellows 513 may have attached piston 512. Piston 512 may pass in and out of gap 502 in order to suck in-vivo bodily fluids into the sensing head, as well as to eject the fluids out of the sensing head, in a periodic manner.

Since device 500 may be swallowed in order to pass through the GI tract, and thus examine the GI tract for presence of blood, peristaltic force may be applied onto device 500. In its initial state, flexible cover 520 may be filled with fluids, e.g., water or air. Once a peristaltic wave passes through the GI tract in the same area as the location of device 500, pressure may be applied onto flexible cover 520. The pressure applied onto flexible cover 520 may cause the fluids that are inside flexible cover 520 to be pushed out of flexible cover 520 and into piston bellows 513, since piston bellows 513 is in fluid contact with flexible cover 520. The fluids that are pushed into piston bellows 513 fill it, thus causing piston bellows 513 to expand into gap 502 towards the end of housing 501 that is closest to gap 502. Once piston bellows 513 expands into gap 502, piston bellows 513 pushes piston 512, which is attached to it, further into gap 502 and towards the end of housing 501, until piston 512 substantially reaches the end of gap 502, which is substantially tangential to the end of housing 501. When piston 512 is pushed until it substantially reaches the end of gap 502, gap 502 is blocked for passage of fluids into it. Once the peristaltic wave continues and passes the location of device 500, flexible cover 520 is no longer pressurized, and fluids flow back from piston bellows 513 into flexible cover 520. Thus, piston bellows 513 and the piston 512 attached to it are pulled back into housing 501, thus reopening gap 502 for free flow of fluids into it. This mechanism, which comprises flexible cover 520, piston bellows 513 and piston 512, uses the natural peristaltic waves in order to suck and eject fluids in and out of gap 502.

Device 500 may further comprise a transmitter 515 for transmitting the light detected by detector 504 to a receiver located externally to device 500. Device 500 may further comprise an internal power source 505, e.g., batteries such as silver-oxide batteries. Device 500 may also comprise processor 514 for processing the data collected by detector 504 and determining presence of blood within the GI tract. In other embodiments, processor 514 may not be encapsulated within housing 501 but rather may be outside device 500, e.g., as part of a separate external receiver located outside of device 500.

In some embodiments, device 500 may comprise an imager (not shown). The imager may be located within housing 501, at the end of housing 501, opposite the blood sensing head. The imager may acquire images of the lumen through which device 500 passes. The images may then be used in order to identify the location of device 500 along the lumen, e.g., along the GI tract. A processor, e.g., processor 514, may correlate the images with the data detected by detector 504, thus an indication of the in-vivo location of detected bleeding may be obtained. The images may be correlated with the data detected by detector 504 according to time of acquisition of the images and time of acquisition of the data detected by detector 504. For example, processor 514 may match between images and signals detected by detector 504, which were both acquired at substantially the same time.

In some embodiments, device 500 may comprise two pH electrodes. Each pH electrode may be located on a different side of gap 502, in order to collect pH data of the fluids flowing into gap 502, in addition to examining the fluids for presence of blood.

In some embodiments, device 500 may further comprise pressure sensor 523. Pressure sensor 523 may measure pressure of the fluid that flows between flexible cover 520 and piston bellows 513. The pressure of the fluid may indicate the amount of pressure of the contracting (and relaxing) lumen through which device 500 passes. Thus, pressure sensor 523 may provide information on in-vivo pressure along the GI tract.

Figure 10:
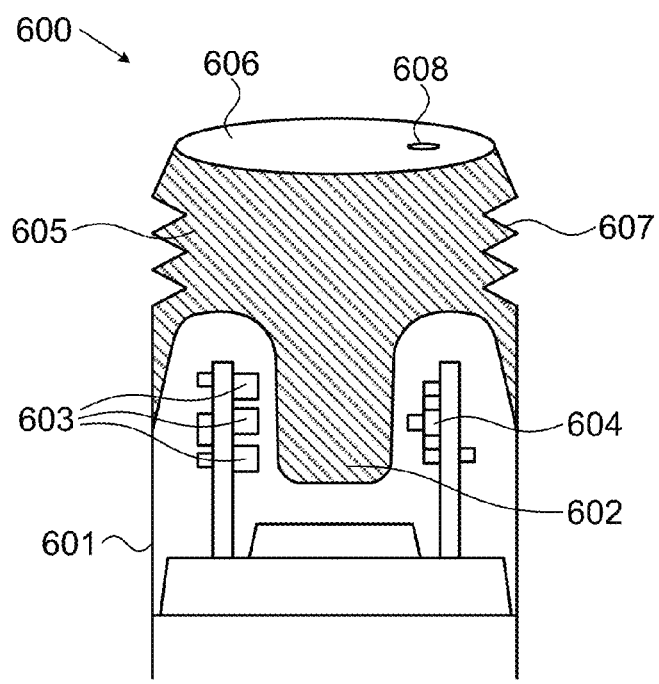
FIG. 10 is a schematic illustration of a side-view cross-section of an in-vivo device, in accordance with an embodiment of the invention.

Reference is now made to FIG. 10, which is a schematic illustration of a side-view cross-section of an in-vivo device in accordance with an embodiment of the invention. In-vivo device 600 may be a swallowable autonomous device. Device 600 may comprise housing 601, which encapsulates the components of device 600. Housing 601 may comprise gap 602, typically located at one of the ends of housing 601. Gap 602 may allow the flow of bodily fluids in and out thereof. On one side of gap 602 may be illumination sources 603, which may illuminate the bodily fluids that enter gap 602. On the opposite side of gap 602, and facing illumination sources 603, may be detector 604 for detecting light from illumination sources 603 that passed through the in-vivo bodily fluids. According to some embodiments, device 600 may comprise a membrane/filter 605, which may cover gap 602. The parameters of membrane 605 may be designed by choice, e.g., the size of pores of membrane 605 may be similar to the size of blood cells. Thus, only blood cells or blood cells residues and particles of the same size or smaller that are present within in-vivo fluids may enter gap 602. However, tissue and larger particles that may fill gap 602 and thus interfere with examination of presence of blood in the fluids located within gap 602, may be blocked by membrane 605 from entering into gap 602. Other parameters of membrane 605 may also be pre-designed, for example, porosity density (e.g., high porosity density of 80% in order to allow high fluid flow per unit area), filtration constant (e.g., to achieve high flow rate at a low pressure), thickness, hydrophilic or hydrophobic polymers, hydrophilic or hydrophobic coating, low-protein binding materials, etc. Since tissue, large particles and air bubbles are blocked from entering gap 602; the signals that may be detected by detector 604 may be substantially noise-free, such that higher sensitivity and detection accuracy may be achieved by device 600.

According to some embodiments, membrane 605 may comprise a flexible spring-like element 607, which is relaxed in its initial state. In some embodiments, the mechanical properties such as spring constant of flexible element 607 may be adjusted to fit the forces range or pressure range present in an active GI tract. Flexible element 607 may be soft enough to allow peristalsis to act on it and cause it to flex, while being strong enough to expand to relaxed state once peristalsis relaxes. The flexed and relaxed motions cause efficient fluid transit across membrane 605. Flexible element 607 may be positioned on top of gap 602, and may either be a separate element from membrane 605 although attached to membrane 605, or it may be inseparable from membrane 605, such that membrane 605 is manufactured to have a flexible shape around gap 602. Flexible element 607 may be exposed to the in-vivo environment, as illustrated in FIG. 10. However, according to other embodiments, flexible element 607 may be located within and attached to membrane 605, such that flexible element 607 has no direct contact with the in-vivo environment through which device 600 passes.

At the top end of flexible element 607, there may be a cover 606. Cover 606 may be attached to flexible element 607 such that cover 606, flexible element 607 and membrane 605 create a closed space within gap 602 and somewhat above it.

In some embodiments, gap 602 may initially be filled with air, prior to device 600 being administered in-vivo. Device 600 may then be administered in-vivo, e.g., into the GI tract, by swallowing device 600. Once device 600 is inside the GI tract, when a peristaltic wave passes the location at which device 600 is located, the peristaltic wave applies pressure onto device 600 and thus pressure is applied onto cover 606 as well. When cover 606 is pressed by the peristaltic wave, flexible element 607 is forced to flex, thus shrinking or decreasing the initial volume or space defined by cover 606, flexible element 607 and membrane 605. After the peristaltic wave passes device 600, and thus device 600 is no longer under pressure, the flexible element 607 returns to its relaxed state, similar to a spring's behavior. The natural peristaltic pressure causes flexible element 607 to act as a pump and attain efficient flow of fluids across the membrane; when flexible element 607 is relaxed to its extended position, fluids and particles of choice (according to predefined parameters of membrane 605) may enter gap 602 and be examined by detector 604. However, when element 607 is flexed, fluids exit gap 602 through membrane 605, clearing the way for new fluids to enter and thus be examined by detector 604.

In some embodiments, cover 606 may comprise a small opening 608 through which fluids may be filled into the space created by cover 606, flexible element 607 and membrane 605 with fluids. The fluids that may be used to fill gap 602 and the rest of the space may be saline, although other fluids may also be used, as long as the selected fluid is biocompatible with in-vivo fluids. The fluid may be administered into device 600 by, for example, a syringe with a needle at the end. The needle may be pushed through opening 608, the fluid may be inserted into the space, and the needle may then be removed from device 600. Opening 608 may be made of silicone, such that, after filling gap 602 and the rest of the space with the fluid, the fluid would not be able to exit through opening 608, since silicone has the ability to close itself following insertion of a needle of a small gauge. In other embodiments, opening 608 may be made of materials other than silicone.

Once the space created by membrane 605, cover 606 and flexible element 607 is filled with fluid, device 600 may be administered in-vivo. Filling the space with fluid prior to administering device 600 may ensure better immediate flow of in-vivo bodily fluids into gap 602 and the rest of the space. The process of external fluids entering a space filled with air may take longer (if at all) than external fluids replacing fluids already within the space. In such embodiments, peristaltic pressure may cause flexible element 607 to flex, thus shrinking the space and applying pressure onto the fluids within the space, and causing some of the fluids to flow out through membrane 605. When the peristaltic pressure stops, flexible membrane 607 may relax again, which causes the space to grow back to its initial dimensions, which may thus cause in-vivo fluids to flow into gap 602 and replace the fluids initially filling gap 602. Once again, the natural peristaltic pressure is used as a natural pump in order to continuously fill gap 602 with new in-vivo bodily fluids, and thus enabling examination of those fluids by detector 604.

In some embodiments, cover 606 may either be rigid or flexible. Furthermore, cover 606 may be substantially sealed to the passage of particles and fluids, although in other embodiments, cover 606 may comprise pores through which fluids and/or particles in a size of choice may pass through. In some embodiments, cover 606 may be made of the same material of which membrane 605 is made.

Figure 10A:
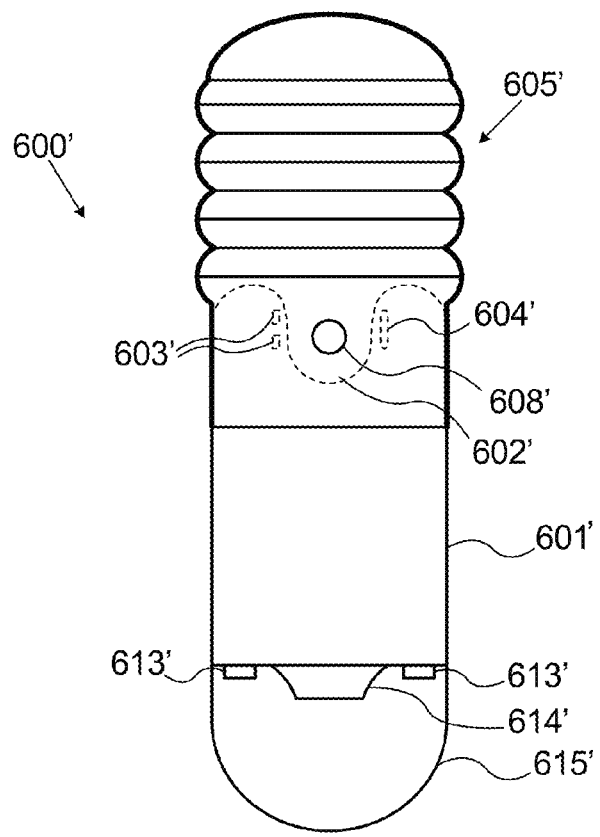
FIG. 10A is a schematic illustration of a side-view cross-section of an in-vivo device, in accordance with an embodiment of the invention.

Reference is now made to FIG. 10A, which is a schematic illustration of a side-view cross-section of an in-vivo device in accordance with an embodiment of the invention. In-vivo device 600' may be an autonomous swallowable device. Device 600' may comprise housing 601', which encapsulates the components of device 600'. Housing 601' may comprise a sensing head in the form of a gap 602', typically located at one of the ends of housing 601'. Gap 602' may allow the flow of bodily fluids in and out thereof. On one side of gap 602' may be located a plurality of illumination sources 603', which may illuminate the bodily fluids that enter gap 602'. Each of the plurality of illumination sources 603' may irradiate the in-vivo fluids passing through gap 602' at a different narrow band wavelength. On the opposite side of gap 602', and facing illumination sources 603', may be located a light detector 604' for detecting light irradiated from illumination sources 603' after the light passed through the in-vivo bodily fluids which are present within gap 602'. Since gap 602' is open to free passage of fluids in and out thereof, it may also allow free entry of bubbles and content or non-fluid particles into the gap, which may disrupt the operation of device 600' by, for example, blocking passage of light from illumination source 603' towards light detector 604' and thus creating noise in the detected light signals collected by detector 604'.

Therefore, according to some embodiments, device 600' may comprise a cover 605', which may be placed over gap 602' such to cover gap 602' and which is designed to limit or even exclude passage of bubbles and non-fluid particles into gap 602'.

Cover 605' may be made of a flexible biocompatible material, such as silicone, latex, rubber or any other flexible biocompatible material. Cover 605' may have a shape similar to an accordion, e.g., cover 605' may change and reduce its shape by contracting or shrinking when pressure is applied onto it, while also being able to expand to its initial shape when no pressure is applied onto it. Cover 605' may have a shape different than an accordion, as long as the shape of cover 605' enables it to contract while under peristaltic pressure, and then enables it to expand to its initial shape once peristaltic pressure is no longer applied onto it. Cover 605' may further comprise at least one hole or opening 608', which may be located in close proximity to the sensing area that is defined as the area between illumination sources 603' and light detector 604', in which light detector 604' detects light irradiated from illumination sources 603' after the light passed through in-vivo fluids that were present within the sensing area. In some embodiments, at least one hole or opening 608' is located at the sensing area on an axis perpendicular to the axis along which illumination source 603' and light detector 604' are located.

Typically, at least one opening 608' may comprise two openings located on opposite sides of the sensing area, located along the same axis which is perpendicular to the axis along which illumination sources 603' and light detector 604' are located. Two, typically opposing openings 608' may facilitate better flow in and out of gap 602', since two opposing openings may enable quicker entry and exit of fluids therefrom. Furthermore, non-fluid particles or bubbles that may have entered through openings 608' have more than one opening through which they can exit thus freeing the sensing area from interruptions and noise more quickly and more effectively.

When peristaltic pressure is applied onto cover 605', i.e., when a peristaltic wave passes by device 600', the peristaltic pressure may cause cover 605' to squeeze and contract. When cover 605' is squeezed by peristaltic pressure, fluids that have already entered gap 602' (through at least one opening 608') are forced to be pushed out of gap 602', through at least one opening 608'. When peristaltic pressure is no longer present in proximity to device 600', and thus is no longer applied onto device 600', cover 605' may then be re-filled with new in-vivo fluids now entering gap 602' through at least one opening 608'. Cover 605' may then return to its initial un-squeezed flexible accordion-like shape. Peristaltic pressure is used as part of the operation of device 600' so as to facilitate better flow of fluids into and out of gap 602'. The flexible accordion-like shape, which takes advantage of the typical presence of peristaltic pressure along the GI tract, enables active flow of in-vivo fluids into and out of the sensing area and of gap 602'. The location of the at least one opening 608' is specifically at the sensing area in order to ensure that when fluids are pushed outside of gap 602' through the at least one opening 608', if for some reason, some non-fluid content or bubbles were able to enter into gap 602', these would be pushed outside of gap 602' and would specifically clear the sensing area for proper and accurate sensing of blood related particles only. If the location of at least one opening 608' was any different, for example, not located near the sensing area, then it would not be possible to ensure that the sensing area is constantly free of non-relevant particles related to the detection of blood within the GI fluids.

Furthermore, since peristaltic waves constantly pass along the GI tract, such pressure constantly squeezes cover 605' and forces fluids out of gap 602', while relaxation periods, (i.e., after a peristaltic wave has passed device 600' and is no longer applied onto cover 605'), enables cover 605' to return to its relaxed un-squeezed shape, while sucking in fluids through at least one opening 608' and into gap 602' and thus into the sensing area, for further detection of presence of blood within newly entered GI fluids.

The size of at least one opening 608' may be defined by the size of particles that are relevant for the detection of presence of blood. For example, the size of opening 608' may be similar to the size of blood cells. In other embodiments, the size of opening 608' may be larger than the size of blood cells, in order to enable easier flow of fluids in and out of opening 608', however, the squeezing and releasing mechanism of cover 605' may ensure that even if particles not relevant to detection of blood or bubbles do enter the sensing area within gap 602', such particles and/or bubbles would be pushed out of gap 602' through opening 608' and clear the sensing area for further detection of new in-vivo fluids that may enter during relaxation periods (i.e., after a peristaltic wave passes the location of device 600' and moves farther away from it).

According to some embodiments, device 600' may further comprise an imaging head 615', which may be located at an end of housing 601', which is different than the end at which sensing head 602' is located. Imaging head 615' may typically be located at an end of housing 601' which is opposite the end at which sensing head 602' is located, though other locations are possible. Imaging head 615' may comprise illumination sources 613' for illuminating in-vivo bodily fluids and in-vivo lumen through which device 600' passes along. Imaging head 615' may further comprise an optical head 614', which may comprise an optical system (e.g., a set of lenses or other optical elements) and an imager for acquiring in-vivo images of the bodily fluids and lumen. In some embodiments, the images acquired by imaging head 615' may assist in determining location of device 600' along the GI tract, thus determining location of a bleeding event or presence of blood along the GI tract.

In some embodiments, device 600' may further comprise a transmitter for transmitting the detected light signals to an external receiver. In some embodiments, if device 600' further comprises an imaging head, e.g., imaging head 615', the transmitter may transmit the acquired in-vivo images as well as the detected light signals to an external receiver.

Figure 11:
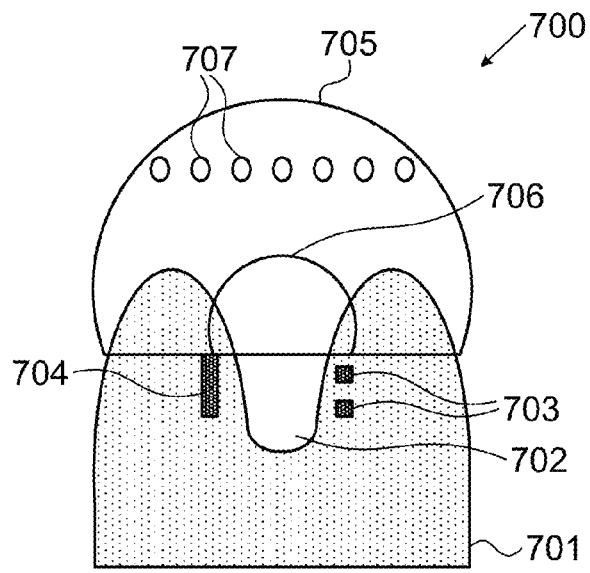
FIG. 11 is a schematic illustration of side-view cross-section of a section of an in-vivo device, in accordance with an embodiment of the invention.

Reference is now made to FIG. 11, which is a schematic illustration of side-view cross-section of a section of an in-vivo device in accordance with an embodiment of the invention. Device 700 may be a swallowable in-vivo autonomous device. Device 700 may comprise housing 701. Housing 701 may comprise gap 702, which may enable flow of in-vivo fluids in and out of gap 702. Illumination source 703 may be located on one side of gap 702, while detector 704 may be located on the opposite side of gap 702, facing illumination sources 703. Illumination sources 703 and detector 704 may define the sensing area in gap 702. In order to prevent tissue from entering gap 702, a cover 705 may be placed over gap 702. Cover 705 may be placed over gap 702 so as not to block the entire opening of gap 702. Cover 705 may comprise an arch 706, which may enable flow of fluids into gap 702, but may not be large enough to enable entrance of tissue into gap 702. Cover 705 may further comprise pores or openings 707 which may perform as openings through which fluid exit gap 702. Cavities or openings 707 may also assist in capturing bubbles, which may enter gap 702, at the top inner end of cover 705, thus distancing between the bubbles and the sensing area, so that the bubbles won't block the sensing area and cause false readings of signals. Cover 705 may be made of various biocompatible materials, e.g., polycarbonate.

Figure 12:
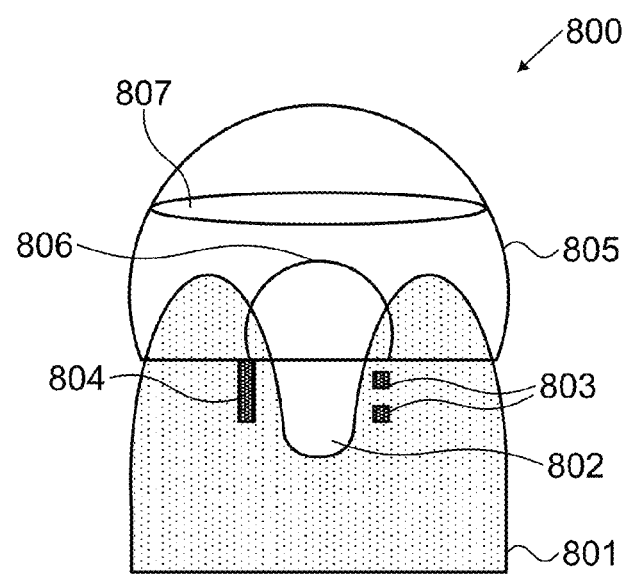
FIG. 12 is a schematic illustration of side-view cross-section of a section of an in-vivo device, in accordance with an embodiment of the invention.
Figure 15A:
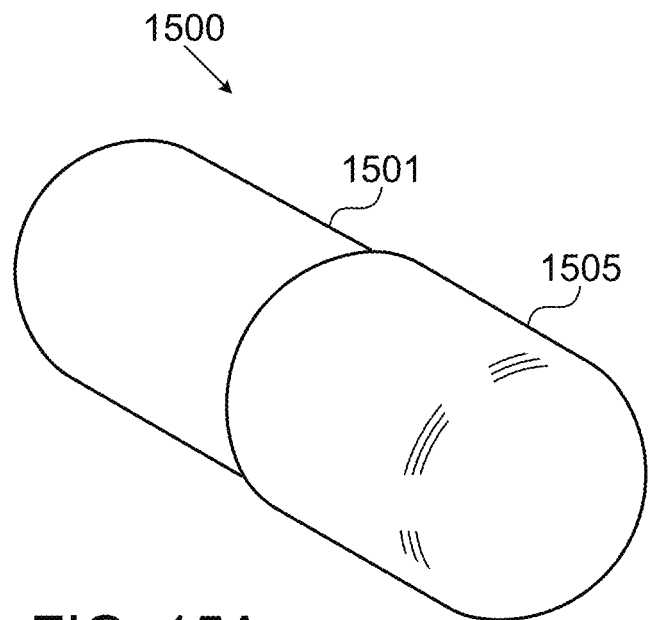
Figure 15B:
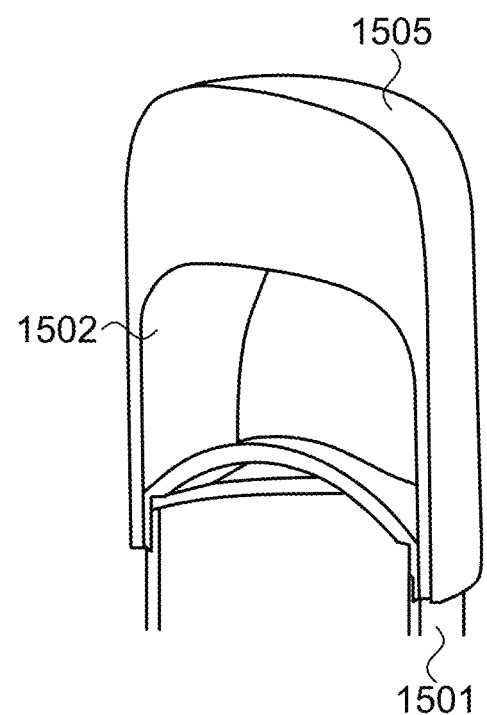

Reference is now made to FIG. 12, which is a schematic illustration of side-view cross-section of a section of an in-vivo device in accordance with an embodiment of the invention. Device 800 is similar to device 700, shown in FIG. 11. Device 800 comprises housing 801, which comprises a gap 802 with a sensing area. The sensing area is the area within gap 802, where illumination sources 803 and detector 804 are located, each being positioned behind one of the opposite sides of gap 802. Device 800 may further comprise a cover 805, which may be placed over gap 802. Cover 805 is preferably not placed over gap 802 such to cover and block the entire opening of gap 802. That is, cover 805 is preferably not placed all the way down over gap 802. In some embodiments, cover 805 may comprise an arch 806, which may enable flow of fluids into gap 802, but may not be large enough to enable entrance of tissue into gap 802. In some embodiments, cover 805 may comprise an opening 807 from the top end of cover 805, which is the end farthest from gap 802, in order to enable better flow through cover 805, while restricting entrance of tissue into gap 802. However, in other embodiments, cover 805 may not comprise opening 807, but rather only arch 806, such that cover 805 may be used to restrict entrance of tissue into gap 802, while not interfering with entry of fluids into gap 802. Cover 805 may be coated from the inside with parylene, which is a hydrophobic material, or other similar materials, thus preventing adherence of fluids and bubbles to the inside of gap 802. This enables fluids and bubbles to exit gap 802 without being stuck inside it.

Reference is now made to FIGS. 13A-B, which are schematic illustrations of a side-view cross-section and an upper-view of a section of an in-vivo device in accordance with an embodiment of the invention, respectively. Device 900 is similar to device 700 (in FIG. 11) and to device 800 (in FIG. 12). Device 900 comprises housing 901, which comprises a gap 902 with a sensing area. The sensing area is the area within gap 902, where illumination sources 903 and detector 904 are located, each being positioned behind one of the opposite sides of gap 902. Device 900 may further comprise a cover 905, which may be placed over gap 902. Cover 905 is preferably not placed over gap 902 such to cover and block the entire opening of gap 902. That is, cover 905 is preferably not placed all the way down over gap 902. According to some embodiments, cover 905 may be in the shape of gratings surrounding gap 902, which may prevent entrance of tissue into gap 902. Gratings 906 may be located around cover 905 so as to block tissue from entering gap 902. Gratings 906 may either comprise two or more gratings surrounding the perimeter of gap 902.

Reference is now made to FIGS. 14A-B, which are schematic illustrations of a side-view cross-section, and an enlargement of a section, respectively, of an in-vivo device in accordance with an embodiment of the invention. FIG. 14A illustrates swallowable autonomous in-vivo device 1000, which may comprise housing 1100. Housing 1100 may typically be in an elongated shape. Housing 1100 may comprise two sensing heads located on opposite sides of elongated housing 1100, along the longitudinal axis of housing 1100. Sensing head 1001 may comprise a gap 1002 which fluids may enter into or exit from. Sensing head 1001 may comprise illumination sources 1003 located on one side of gap 1002 and detector 1004 located on the opposite side of gap 1002, facing illumination sources 1003. The second sensing head 1010 may be similar to sensing head 1001, i.e., head 1010 may also comprise a gap 1012, illumination sources 1013 and detector 1014 located on opposite sides of gap 1012. However, sensing head 1010 may further comprise a coating 1015 coated around the entire gap 1012, thus sealing gap 1012 from contact with external in-vivo fluids. Gap 1012 may be filled with a gel or membrane 1020, which may enable entrance of selected particle, e.g., blood cells, by having pores in the size of blood cells. Membrane 1020 may enable entrance of particles of a specific size through diffusion.

Coating 1015 may be made of a dissolvable material, which may be designed to dissolve after a predetermined time period. For example, the thickness of the coating may be designed such that the coating would dissolve only after the period of time it normally takes a swallowable capsule to reach the colon, e.g., approximately 8 hours after swallowing the capsule. Coating 1015 may be made of lactose, and the thickness of the lactose coating may be designed such that the lactose would dissolve after approximately 8 hours from swallowing device 1000, in order to have gap 1012 be exposed to in-vivo fluids only inside the colon.

Device 1000 is designed to have one sensing head 1001 which begins to examine bodily fluids from the instant it is inserted in-vivo. That is, the upper GI tract is examined for presence of blood by sensing head 1001, and the colon's fluids are to be examined for presence of blood by sensing head 1010. Coating 1015 is designed to dissolve when device 1000 approximately reaches the colon, and membrane or gel 1020 ensure that substantially no content present within the colon would enter gap 1012 besides particles in the size of blood cells, which increases the chances of achieving accurate results in the colon, similar to the upper GI tract, where in-vivo fluids are much less turbid.

Sensing head 1010 may further comprise a coating made of a non-dissolvable material, e.g., parylene, which may cover the dissolvable material of the coating. In order to cause the non-dissolvable coating to rupture inside the colon, so that the gap may be exposed to colon fluids, sensing head 1010 may comprise a device to puncture the non-dissolvable coating. Fluids may then pass through the non-dissolvable coating into the dissolvable coating 1015 such that dissolving of coating 1015 may begin. The puncturing device may be a pin that may be extracted outside of device 1000 in order to puncture the non-dissolvable part of the coating, and may be pulled back into device 1000 at the end of the puncturing procedure, in order to prevent any harm to the lumen. The puncturing device may be operated either by an internal timer carried by device 1000 or by a command provided by the operator of device 1000, e.g., medical care personnel.

Reference is now made to FIGS. 15A-16B, which are schematic illustrations of a side-view and a side-view cross-section, respectively, of an in-vivo device in accordance with an embodiment of the invention. Device 1500 may be a swallowable in-vivo autonomous device. Device 1500 may comprise housing 1501. Housing 1501 may comprise gap 1502, through which in-vivo fluids may enter and exit a sensing area of device 1500 defined by gap 1502, illumination sources (not shown) and a light detector (not shown). The Illumination sources may be located on one side of gap 1502, while a light detector may be located on the opposite side of gap 1502, facing the illumination sources, such that light exits from the illumination sources, passes through fluids present in gap 1502 and reaches the light detector. In order to prevent tissue from entering gap 1502, a cover 1505 may be placed over gap 1502. Cover 1505 may be placed over gap 1502 such to substantially cover the entire gap 1502, though in other embodiments, cover 1505 may not wrap the entirety of gap 1502. Cover 1505 may be made of a sponge or sponge like material comprising pores such to enable passage of fluids through cover 1505 into gap 1502. The size of the pores may be chosen so as to enable passage of blood particles while blocking passage of particles larger than the blood related particles. This would ease on detection of presence of blood in the sensing area, since less particles that are not relevant to blood detection would enter the sensing area.

In some embodiments, cover 1505 may further comprise a layer of membrane that covers the external side of cover 1505. The membrane covering sponge cover 1505 may be a semi-permeable membrane to further filter the fluids before they enter gap 1502.

In some embodiments, when a peristaltic wave passes through the GI tract, and pressure is applied onto cover 1505, since cover 1505 is made of a sponge it may be squeezed such that fluids and particles, which were able to enter the pores of cover 1505 and be present within cover 1505 and gap 1502, may be pressurized to exit gap 1502 through the pores of cover 1505, if the pressure is high enough to fully squeeze cover 1505. When the peristaltic wave moves past the location of device 1500, cover 1505 may return to its relaxed state, and fluids and particles smaller than the size of the pores of cover 1505 may again enter and fill cover 1505 and gap 1502, such that new fluids and particles may enter the sensing area and be detected for presence of blood.

Figure 16A:
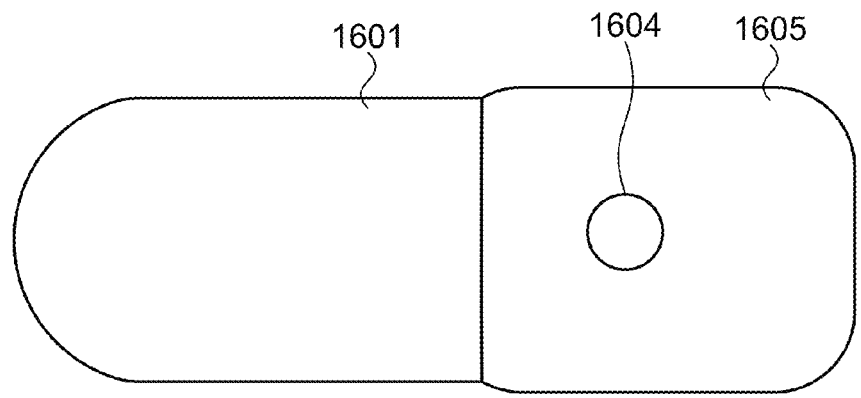
Figure 16B:
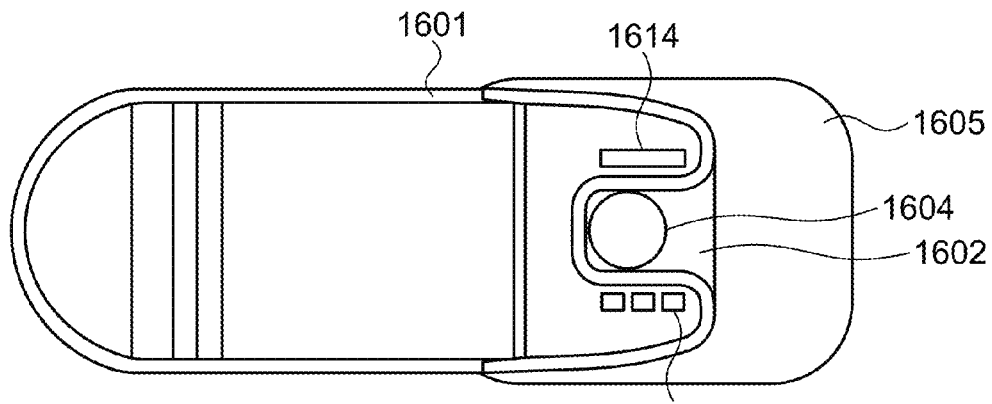
Figure 16C:
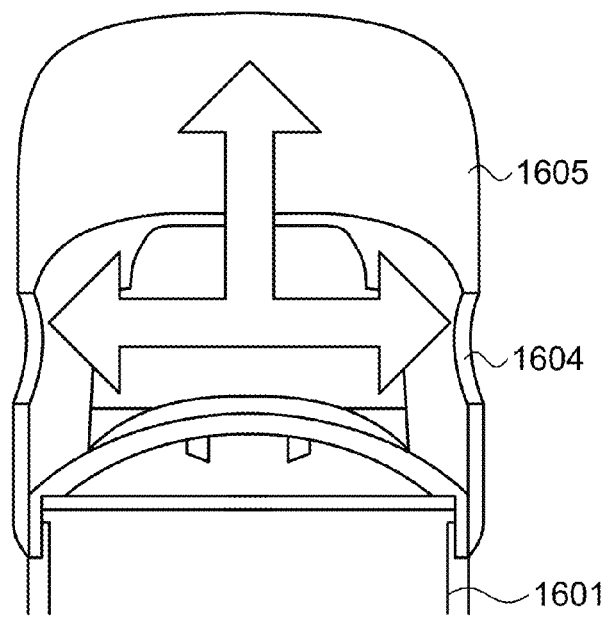

Reference is now made to FIGS. 16A-16C, which schematically illustrate a side-view, a side-view cross section and an enlargement of a section of a side view cross-section, respectively, of an in-vivo device in accordance with an embodiment of the invention. Device 1600 may be a swallowable in-vivo device. According to some embodiments, device 1600 may be similar to device 1500. According to FIG. 16B, device 1600 may comprise housing 1601, which on one end may comprise a sensing area defined by gap 1602, illumination sources 1613 and light detector 1614. Illumination sources 1613 may be located on one side of gap 1602, while light detector 1614 may be located on the opposite side of gap 1602; facing illumination sources 1613 such that light exits from illumination sources 1613, passes through fluids present between illumination sources 1613 and light detector 1614 within gap 1602, and reaches light detector 1614. In order to prevent tissue from entering gap 1602, a cover 1605 may be placed over gap 1602. Cover 1605 may be placed over gap 1602 such to substantially cover the entire gap 1602, though in other embodiments, cover 1605 may not wrap the entirety of gap 1602. Cover 1605 may be made of a sponge or sponge like material comprising pores such to enable passage of fluids through cover 1605 into gap 1602. The size of the pores may be chosen such to enable passage of blood particles while blocking passage of particles larger than the blood related particles. This would ease on detection of presence of blood in the sensing area, since less particles that are not relevant to blood detection would enter the sensing area.

In some embodiments, cover 1605 may further comprise a layer of membrane that covers the external side of cover 1605. The membrane that is coating/covering sponge cover 1605 may be a semi-permeable membrane to further filter the fluids before they enter gap 1602.

In some embodiments, cover 1605 may further comprise holes 1604 in order to enable additional openings at additional directions, with respect to device 1500, through which in-vivo fluids and particles may enter and exit gap 1602 (following detection of presence of blood). In some embodiments, holes 1604 may be located on opposite sides of cover 1605 in order to facilitate better flow in and out of holes 1604, though other locations and other numbers of holes may be used. As illustrated in FIG. 16C, device 1600 may comprise three directions through which in-vivo fluids may enter and/or exit gap 1602. During peristaltic pressure, cover 1605 may be squeezed such that fluids and particles may exit gap 1602 and cover 1605 through the pores of cover 1605, as well as through holes 1604. After the peristaltic wave moves beyond the location of device 1600 along the GI tract, cover 1605 may return to its relaxed state, and new fluids and particles may enter cover 1605 and gap 1602 through the pores in cover 1605, as well as through holes 1604. Thus, peristaltic movement may cause evacuation of fluids and particles from holes 1604 and from cover 1605, as well as enable new fluids and flowing particles to enter gap 1602, and thus be detected for presence of blood.

As illustrated in FIGS. 16A-16B, holes 1604 may include two holes located one opposite the other as well as located across gap 1602, between illumination sources 1613 and light detector 1614. In other embodiments, holes 1604 may be located in other locations along cover 1605 and may include more than two holes. One hole may also be used, although flow would be better with at least two holes.

According to some embodiments, device 1600 may comprise an imaging head located opposite the blood sensing head.

Figure 17:
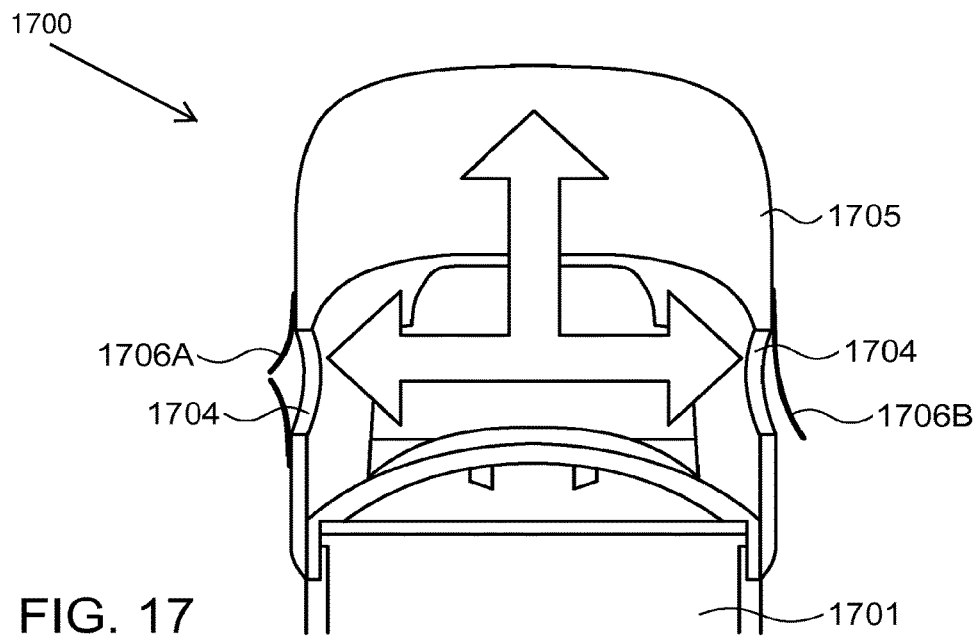
FIG. 17, is a schematic illustration of a side-view cross section of an in-vivo device in accordance with an embodiment of the invention.

Reference is now made to FIG. 17, which schematically illustrates a side-view cross section of an in-vivo device in accordance with an embodiment of the invention. Device 1700 may be a swallowable in-vivo device. According to some embodiments, device 1700 may be similar to device 1600 with a few additions. In some embodiments, device 1700 may comprise housing 1701 that may comprise a sensing area defined by a gap, illumination sources and a light detector located opposite the illumination sources (as illustrated in FIG. 16B). Similarly to device 1600, device 1700 may comprise a cover 1705 to protect the sensing area and block large particles and tissue from entering the sensing area. Cover 1705 may be made of a sponge or sponge like material, in order to filter the fluids and particles prior to entering the sensing area, such as to prevent particles larger than blood related particles from entering the sensing area and thus interfering with detection of blood in-vivo. The size of the pores of cover 1705 may be determined based on the size of typical blood related products flowing within in-vivo GI fluids, when bleeding in the GI tract is present. In some embodiments, cover 1705 may comprise a membrane cover or coating that is covered or coated on the external surface of cover 1705, for extra filtering.

Also, similarly to device 1600, device 1700 may comprise more than one hole 1704 in order to facilitate better flow of in-vivo fluids in and out of the sensing area. Typically, holes 1704 may be located one across the other or one opposite the other, such that flow of fluids from one hole through the other is easy. However, in addition to holes 1704, which are also present in device 1600, device 1700 may comprise valves 1706. Valves 1706 may be one way valves that determine the direction of fluid flow from one end towards the other, and only in that direction, not in the opposite direction. For example, as illustrated in FIG. 17, fluids may flow through valve 1706A into device 1700, and out of valve 1706B. This dictation of direction of flow may enable a more efficient detection of in-vivo fluids, since when in-vivo fluids enter through one certain direction, one may assume that detection of new fluids is made each time new fluids enter device 1700, since the fluids that were already examined by the device moved past device 1700. In addition, valves 1706 limit the entrance of bubbles, feces and tissue into the sensing area.

Figure 18:
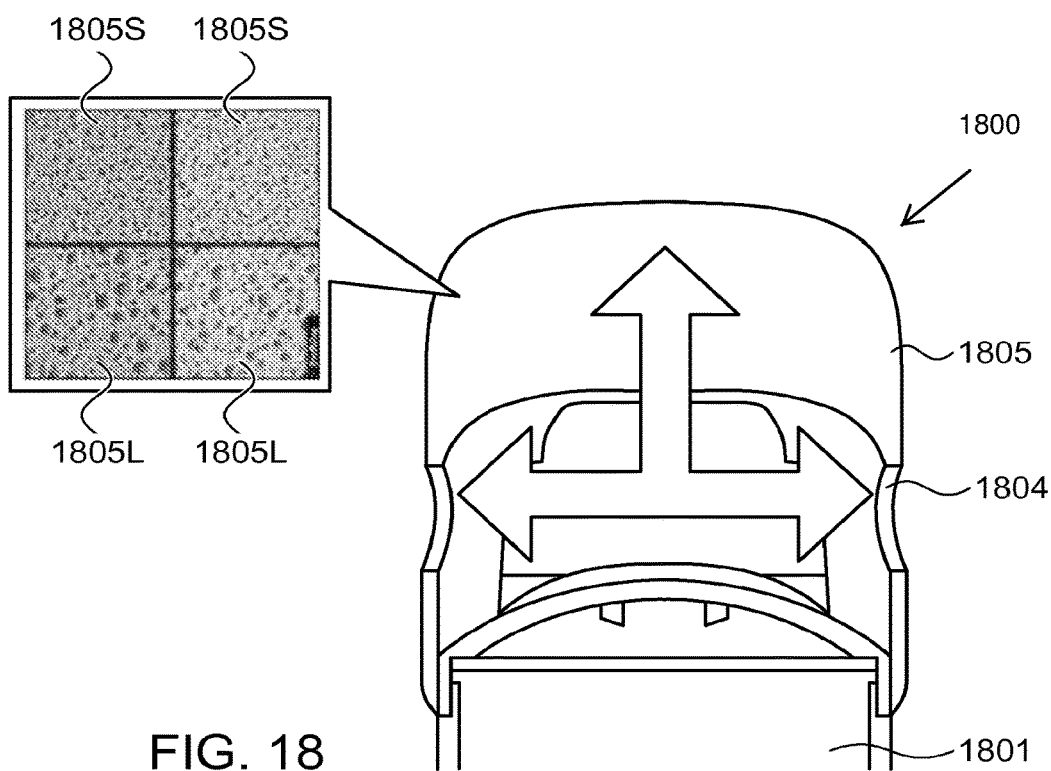
FIG. 18, is a schematic illustration of a side-view cross section of an in-vivo device in accordance with an embodiment of the invention.

Reference is now made to FIG. 18, which schematically illustrates a side-view cross section of an in-vivo device in accordance with an embodiment of the invention. Device 1800 may be a swallowable in-vivo device. According to some embodiments, device 1800 may be similar to device 1800 with a few additions. In some embodiments, device 1800 may comprise housing 1801 that may comprise a sensing area defined by a gap, illumination sources and a light detector located opposite the illumination sources (as illustrated in FIG. 16B). Similarly to device 1600, device 1800 may comprise a cover 1805 to protect the sensing area and block large particles and tissue from entering the sensing area. Cover 1805 may be made of a sponge or sponge like material, in order to filter the fluids and particles prior to entering the sensing area, such as to prevent particles larger than blood related particles from entering the sensing area and thus interfering with detection of blood in-vivo. The size of the pores of cover 1805 may be determined based on the size of typical blood related products flowing within in-vivo GI fluids, when bleeding in the GI tract is present. In some embodiments, cover 1805 may comprise a membrane cover or coating that is covered or coated on the external surface of cover 1805, for extra filtering.

Also, similarly to device 1600, device 1800 may comprise more than one hole 1804 through cover 1805 in order to facilitate better flow of in-vivo fluids in and out of the sensing area. Typically, holes 1804 may be located one across the other or one opposite the other, such that flow of fluids from one hole through the other is continuous. However, device 1800 may comprise a more complex cover 1805 compared to that of device 1600. Cover 1805 may comprise differential pore size layers. In some embodiments, cover 1805 may comprise at least two types of sponges with different sizes of pores. For example, in the enlarged section of cover 1805, it is shown that the external surface of cover 1805, section 1805S that is to be in contact with the in-vivo environment once device 1800 is inserted into the GI tract, may comprise smaller pores with respect to the pore size of the inner section 1805L of cover 1805. External section 1805S, which comprises the small pores, may be used to filter the fluids and particles flowing with the fluids, prior to them entering the sensing area for detection of blood. And the pores become larger in the internal section 1805L so as to enable easier passage of fluids and particles into the sensing area after filtration was accomplished.

In some embodiments, cover 1805 may further comprise one-way valves, such as those described in FIG. 17, so as to direct fluid flow in one specific direction through holes 1804.

Figure 19A:
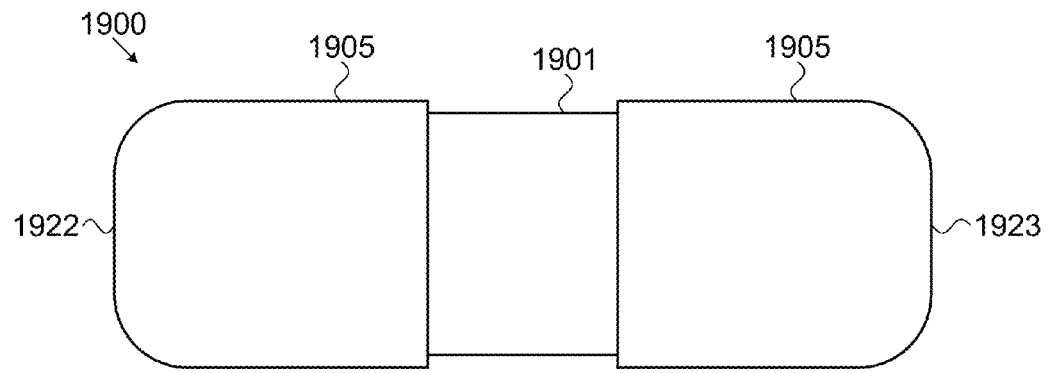
FIGS. 19A-19B, are schematic illustrations of a side-view and a side-view cross section, respectively, of an in-vivo device in accordance with an embodiment of the invention.
Figure 19B:
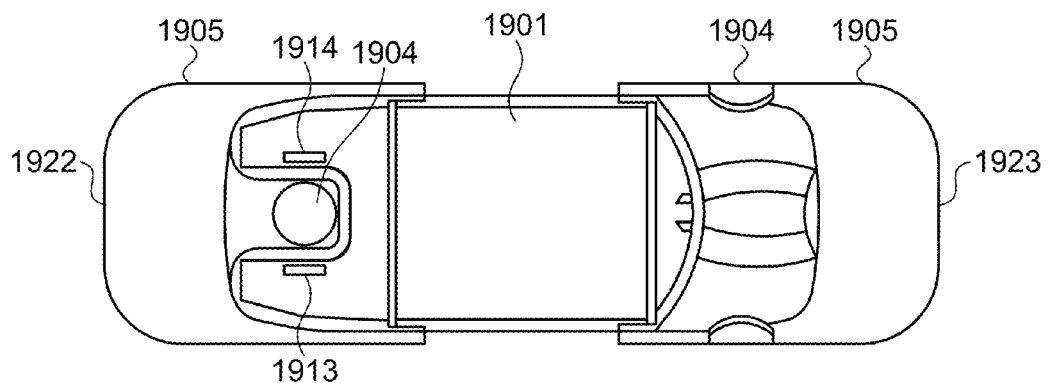

Reference is now made to FIGS. 19A-19B, which schematically illustrate a side-view and a side-view cross section, respectively, of an in-vivo device in accordance with an embodiment of the invention. Device 1900 may be a swallowable in-vivo device. According to some embodiments, device 1900 may be similar to device 1600 (FIG. 16A) but with two blood sensing heads instead of one. In some embodiments, device 1900 may comprise housing 1901 that may comprise two sensing areas, each of the sensing areas may be defined by a gap, illumination sources 1913 and a light detector 1914 located opposite the illumination sources 1913 (as illustrated in FIG. 16B). In some embodiments, each of blood sensing heads 1922 and 1923 may comprise a cover 1905 to protect the sensing area and block large particles and tissue from entering the sensing area. Cover 1905 may be made of a sponge or sponge like material, in order to filter the fluids and particles prior to entering either of the sensing areas in either of heads 1922 or 1923, such as to prevent particles larger than blood related particles from entering the sensing area and thus avoiding interference with detection of blood in-vivo. The size of the pores of cover 1905 may be determined based on the size of typical blood related products flowing within in-vivo GI fluids, when bleeding in the GI tract is present. In some embodiments, cover 1905 may comprise a membrane cover or coating that is covered or coated on the external surface of cover 1905, for extra filtering.

Also, similarly to device 1600, device 1900 may comprise more than one hole 1904 through each of the covers 1905 in order to facilitate better flow of in-vivo fluids in and out of the sensing area. Typically, holes 1904 may be located one across the other or one opposite the other, such that flow of fluids from one hole and through the other is continuous.

In some embodiments, each of ends 1922 and 1923 may comprise the same type of cover 1905. However, in other embodiments, end 1922 may comprise a different type of cover 1905 than the cover of end 1923.

In some embodiments, device 1900 may comprise at least one cover 1905 similar to cover 1805 (FIG. 18). Cover 1905 may comprise differential pore size layers. In some embodiments, cover 1905 may comprise at least two types of sponges with different sizes of pores. For example, the external surface of cover 1905 that is to be in contact with the in-vivo environment once device 1900 is inserted into the GI tract, may comprise smaller pores with respect to the pore size of the inner section of cover 1905. The external section of cover 1905, which comprises the small pores, may be used to filter the fluids and particles flowing with the fluids, prior to them entering the sensing area for detection of blood. And the pores become larger in the internal section of cover 1905 so as to enable easier passage of fluids and particles into the sensing area after filtration has been accomplished.

In some embodiments, at least one of covers 1905 may further comprise one-way valves, such as those described in FIG. 17, so as to direct fluid flow in one specific direction through holes 1904.

Figure 20A:
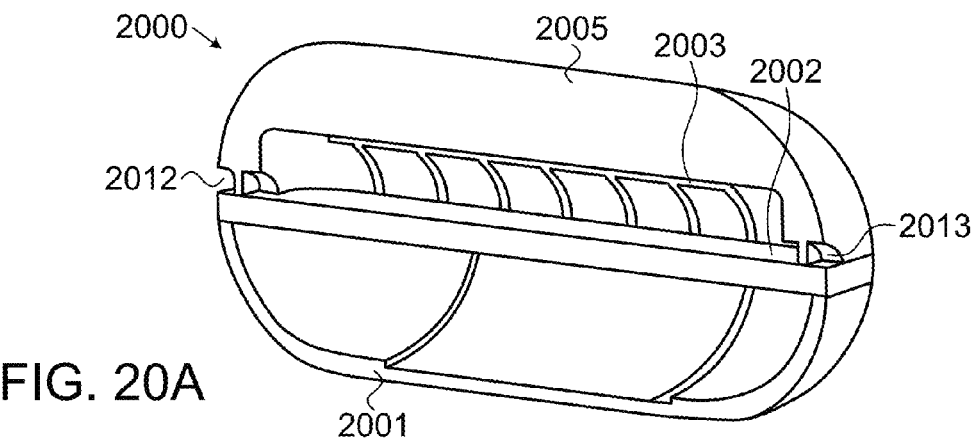
FIGS. 20A-20B, are schematic illustrations of side-view cross sections of an in-vivo device in accordance with an embodiment of the invention.
Figure 20B:
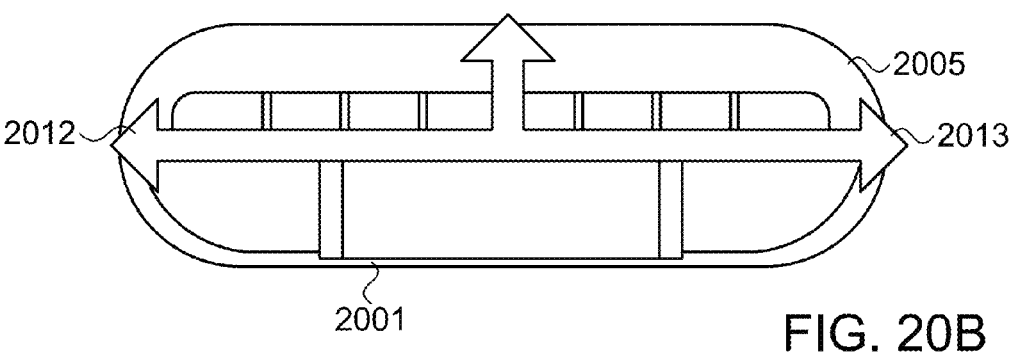

Reference is now made to FIGS. 20A-20B, which schematically illustrate side-view cross sections of an in-vivo device in accordance with an embodiment of the invention. Device 2000 may be a swallowable in-vivo device. Device 2000 may comprise housing 2001 with an elongated shape that enables ease of swallowing, e.g., cylindrical with rounded edges or ellipsoidal. Housing 2001 may comprise passage 2002, which may pass longitudinally through entire housing 2001 from one end of housing 2001 (e.g., end 2012) to the opposite end of housing 2001 (e.g., end 2013), thereby creating a tube-shaped device. Device 2000 may comprise an optical area (or sensing area) located along the passage. The optical area may comprise illumination sources (e.g., having different narrow band wavelengths) and a light detector facing the illumination sources such that light exits from the illumination sources, passes through fluid flowing through passage 2002 and then reaches the light detector. Unlike device 200 (FIG. 5), device 2000 may comprise a symmetrical passage 2002 that has the same diameter all the way through passage 2002.

In some embodiments, the diameter of passage 2002 and the diameter of the openings at ends 2012 and 2013 may be between 3 to 5 mm. In some embodiments, 3 mm is the minimum diameter in order to ensure continuous flow of fluids through passage 2002. At a diameter smaller than 3 mm, flow may be slowed down and be less continuous. In some embodiments, 5 mm is the maximum diameter, since a larger diameter would affect the optical distance between the illumination sources and the light detector, and the longer the distance the light is required to pass, the lower the intensity of the detected light signal. In some embodiments, the location of the light detector and illumination sources may be at a distance of at least 5 mm from each of ends 2012 and 2013, such that GI tissue that might enter through the openings (typically during peristaltic waves when tissue may be pushed into either of the openings on ends 2012 and 2013) would not interfere and would not block the passage of light between the illumination sources and the light detector.

Device 2000 may comprise a protective cage 2003, which protects the sensing area, i.e., the illumination sources and the light detector, which detect presence of blood within the in-vivo fluids. Typically, the illumination sources and the light detector are located one facing the other, although in some embodiments the illumination sources and the light detector may be located on the same side of passage 2002 and a reflective element may be located on the opposite side of passage 2002 to reflect the light passing through the fluids towards the light detector. Cage 2003 may comprise a cover 2005 which covers the entirety of cage 2003. Cover 2005 may be made of a sponge or sponge-like material, which contains pores with a size that is typically designed to be small enough so as to prevent feces and bubbles from entering cage 2003 and thus preventing entrance of such particles into the sensing area, and yet large enough to allow passage of blood and blood related particles to enter the sensing area through cage 2003.

As shown in FIG. 20B, there may be three directions through which in-vivo fluids may enter and/or exit device 2000. For example, fluids may enter passage 2002 through either of the ends of device 2000, e.g., ends 2012 and 2013, or through the pores in cover 2005. As described with regards to device 1500 (FIG. 15), cover 2005 may be squeezed when pressure is applied onto it, for example, when a peristaltic wave is passing the location at which device 2000 is present. When squeezed, cover 2005 may push fluids and particles from it into passage 2002 and out of passage 2002 through openings 2012 or 2013. After the pressure is gone, e.g., after the peristaltic wave has moved past device 2000, cover 2005 may return to its relaxed state and allow entrance of new in-vivo fluids into cover 2005 and into passage 2002, so the fluids may be examined for presence of blood.

Figure 21:
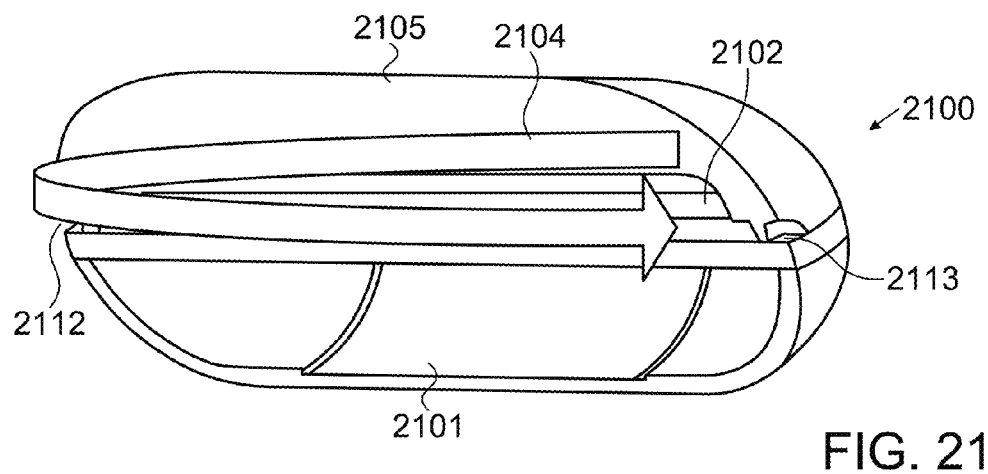
FIG. 21 is a schematic illustration of a side-view cross section of an in-vivo device in accordance with an embodiment of the invention.

Reference is now made to FIG. 21, which schematically illustrates a side-view cross section of an in-vivo device in accordance with an embodiment of the invention. Device 2100 may be a swallowable in-vivo device. Device 2100 may comprise housing 2101 with an elongated shape that enables ease of swallowing, e.g., cylindrical with rounded edges or ellipsoidal. Housing 2101 may comprise passage 2102, which may pass longitudinally through entire housing 2101 from one end of housing 2101 (e.g., end 2112) to the opposite end of housing 2101 (e.g., end 2113), thereby creating a tube-shaped device. Device 2100 may comprise an optical area (or sensing area) located along the passage. The optical area may comprise illumination sources (having different narrow band wavelengths) and a light detector facing the illumination sources such that light exits from the illumination sources, passes through fluid flowing through passage 2102 and then reaches the light detector. Unlike device 200 (FIG. 5), device 2100 may comprise a symmetrical passage 2102 that has the same diameter all the way through passage 2102.

Device 2100 may comprise a protective cage 2103, which protects the sensing area, i.e., the illumination sources and the light detector, which detect presence of blood within the in-vivo fluids. Typically, the illumination sources and the light detector are located one facing the other, although in some embodiments the illumination sources and the light detector may be located on the same side of passage 2102 and a reflective element may be located on the opposite side of passage 2102 to reflect the light passing through the fluids towards the light detector. Cage 2103 may comprise a cover 2105 which covers the entirety of cage 2103. Cover 2105 may be made of a sponge or sponge-like material, which contains pores with a size that is typically designed to be small enough so as to prevent feces and bubbles from entering cage 2103 and thus preventing entrance of such particles into the sensing area, and yet large enough to allow passage of blood and blood related particles to enter the sensing area through cage 2103.

Unlike device 2000, device 2100 may be designed such to have directed flow, from one end of passage 2102 to the opposite end of passage 2102. Directed flow may be achieved, for example, by implementing a one-way valve on the openings of passage 2102, as in device 1700 (FIG. 17). Directed flow may ensure fluid flow through passage 2102 and thus through the sensing area, as well as improve circulation of the flowing fluid. Implementation of a one-way valve may minimize false positives by minimizing particles entering passage 2102 and thus minimizing their entrance into the sensing area.

Figure 22A:
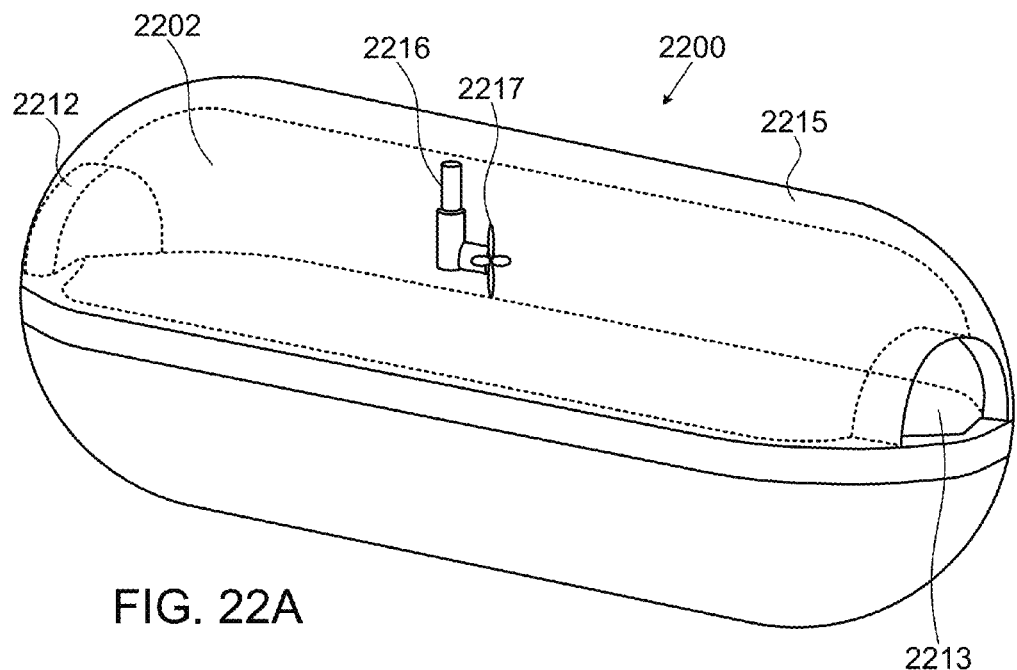
FIGS. 22A-22B are schematic illustrations of side views of an in-vivo device in accordance with an embodiment of the invention.
Figure 22B:
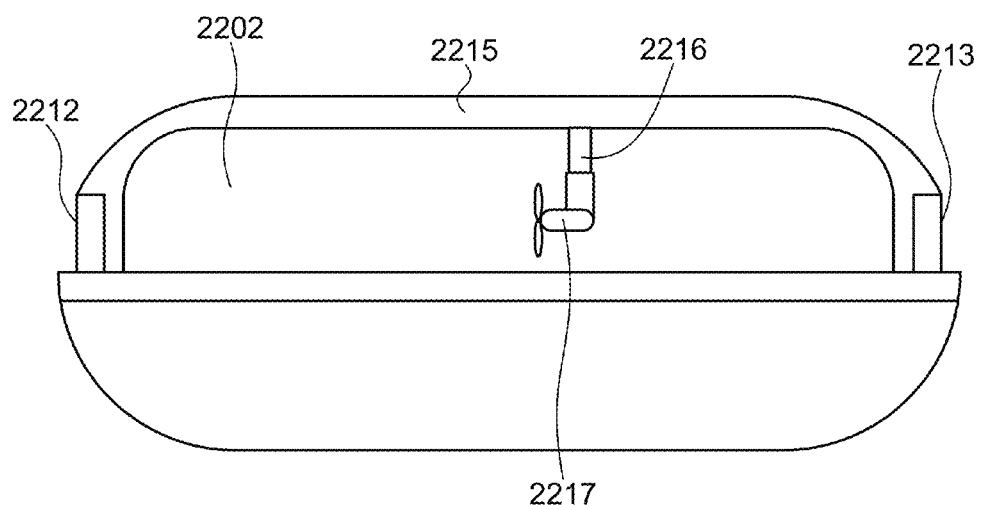

Reference is now made to FIGS. 22A-22B, which schematically illustrate side views of an in-vivo device in accordance with an embodiment of the invention. Device 2200 may be a swallowable in-vivo device. Device 2200 may comprise housing 2201 with an elongated shape that enables ease of swallowing, e.g., cylindrical with rounded edges or ellipsoidal. Housing 2201 may comprise passage 2202, which may pass longitudinally through entire housing 2201 from one end of housing 2201 (e.g., end 2212) to the opposite end of housing 2201 (e.g., end 2213), thereby creating a tube-shaped device. Device 2200 may comprise an optical area (or sensing area) located along passage 2202. The optical area may comprise illumination sources (e.g., having different narrow band wavelengths) and a light detector facing the illumination sources such that light exits from the illumination sources, passes through fluid flowing through passage 2202 and then reaches the light detector. Unlike device 200 (FIG. 5), device 2200 may comprise a symmetrical passage 2202 that has the same diameter all the way through passage 2202.

In some embodiments, device 2200 may further comprise a soft membrane 2215, which may be pressed by the intestinal walls surrounding in-vivo device 2200. Once membrane 2215 is pushed by the intestinal wall, for example, during a peristaltic wave, spring 2116 becomes loaded. Once external pressure is released, spring 2216 is also released and rotor 2217 may activate flow through passage 2202. This mechanism causes directed flow (flow at a certain direction) through device 2200. A rotor, such as rotor 2217, may be useful in activating and facilitating directed fluid flow through passage 2202 which may cause new fluids with blood or blood residues to enter passage 2202 and thus enable their detection in the sensing area. Rotor 2217 may convert a series of random contractions into a nearly continuous rotation and fluid flow.

Figure 23A:
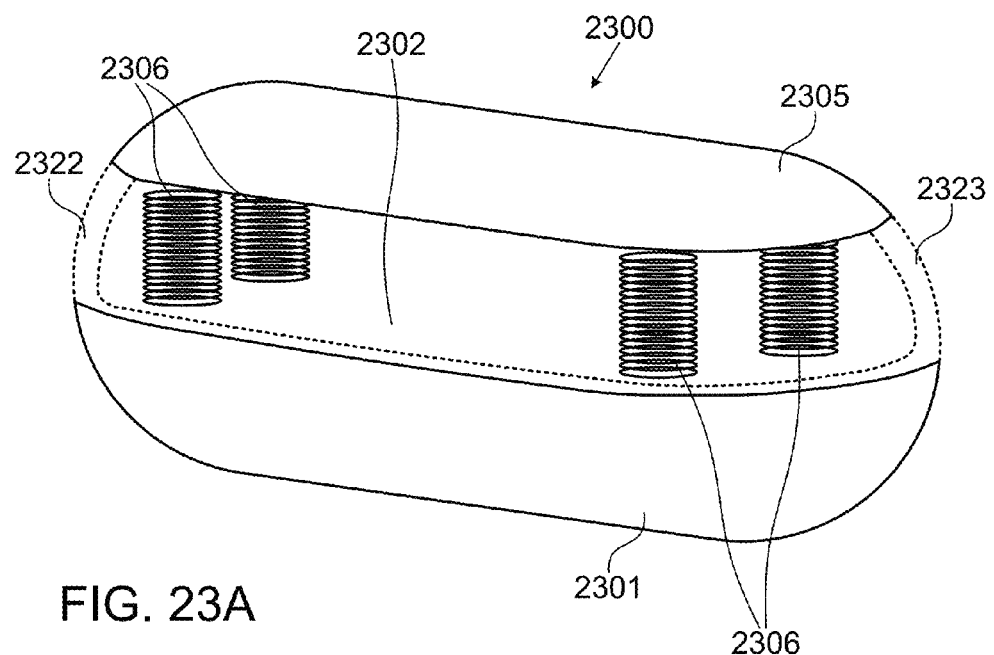
FIGS. 23A-23C are schematic illustrations of side views of an in-vivo device in accordance with an embodiment of the invention.
Figure 23B:
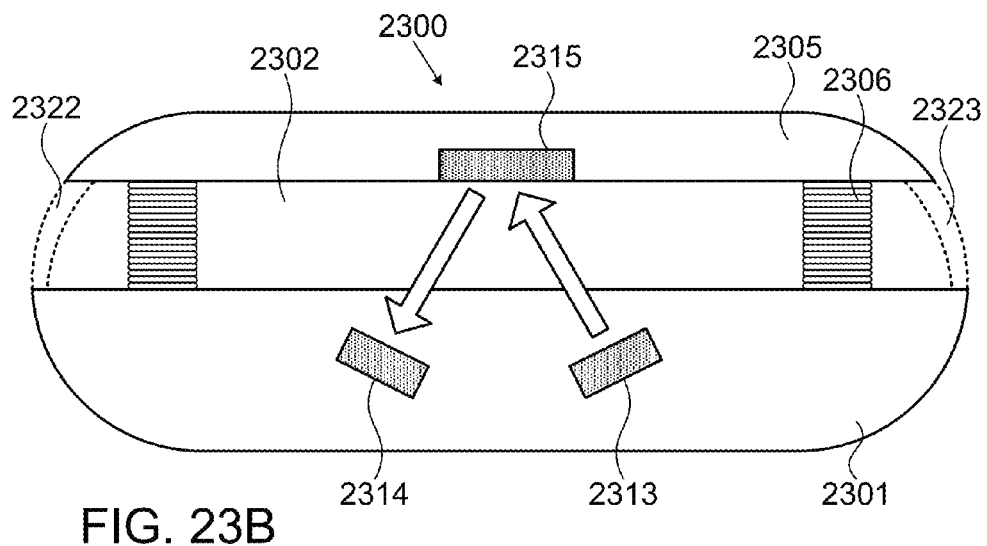
Figure 23C:
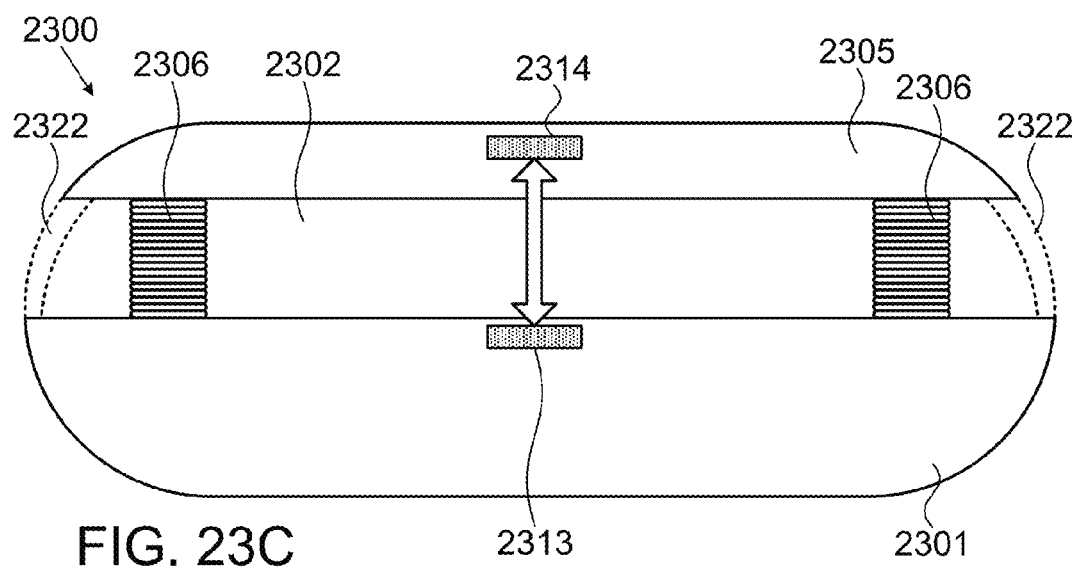

Reference is now made to FIGS. 23A-23C, which schematically illustrate side views of an in-vivo device in accordance with an embodiment of the invention. Device 2300 may be a swallowable in-vivo device. Device 2300 may comprise housing 2301 with an elongated shape that enables ease of swallowing, e.g., cylindrical with rounded edges or ellipsoidal. Housing 2301 may comprise passage 2302, which may pass longitudinally through entire housing 2301 from one end of housing 2301 (e.g., end 2322) to the opposite end of housing 2301 (e.g., end 2323), thereby creating a tube-shaped device. Device 2300 may comprise an optical area (or sensing area) located along passage 2302. The optical area may comprise illumination sources for illuminating the passing fluid with different narrow band wavelengths, and a light detector for detecting light signals after light passed through the fluid flowing along passage 2302.

In some embodiments, device 2300 may further comprise a cover 2305 which covers a portion of housing 2301, while maintaining the two open ends 2322 and 2323. Cover 2305 may be made of a solid and hard material. Cover 2305 may be connected to a plurality of springs 2306. For example, as illustrated in FIG. 23A, device 2300 may comprise four springs 2306, two for each end of device 2300, though other numbers of springs and other orientations of the springs may be used. Once pressure is applied onto cover 2305 by, for example, the GI walls during peristaltic wave, cover 2305 is pushed towards the other portion of housing 2201, and the hollow passage 2302 retains a smaller diameter, thus causing fluids to exit from the openings of housing 2301, e.g., openings 2322 and 2323. When pressure is released, springs 2306 may relax and return to their initial state, thus the diameter of passage 2302 may return to its initial wider diameter, and new fluids may enter passage 2302. Device 2300 may provide good entrance and evacuation of fluids from passage 2302 and thus from device 2300.

According to some embodiments, as illustrated in FIG. 23B, illumination sources 2313 may be located on the same side of housing 2301 as is light detector 2314. In order for light signals emanating from illumination sources 2313 to reach light detector 2314, cover 2305 may comprise a reflector 2315 to reflect light illuminated from illumination source 2313 towards light detector 2314.

According to other embodiments, as illustrated in FIG. 23C, illumination sources 2313 may be located on one side of passage 2302, while light detector 2314 may be located on the opposite side of passage 2302, while facing illumination sources 2313, such that light illuminated by illumination sources 2313 may pass through the fluids flowing through passage 2302 and may be collected by light detector 2314. It should be noted that the light path in the device illustrated in FIG. 23C is shorter than that in the device illustrated in FIG. 23B, so it may be assumed that the signals detected by the light detector in the device of FIG. 23C would be stronger compared to the device in FIG. 23B.

Figure 24A:
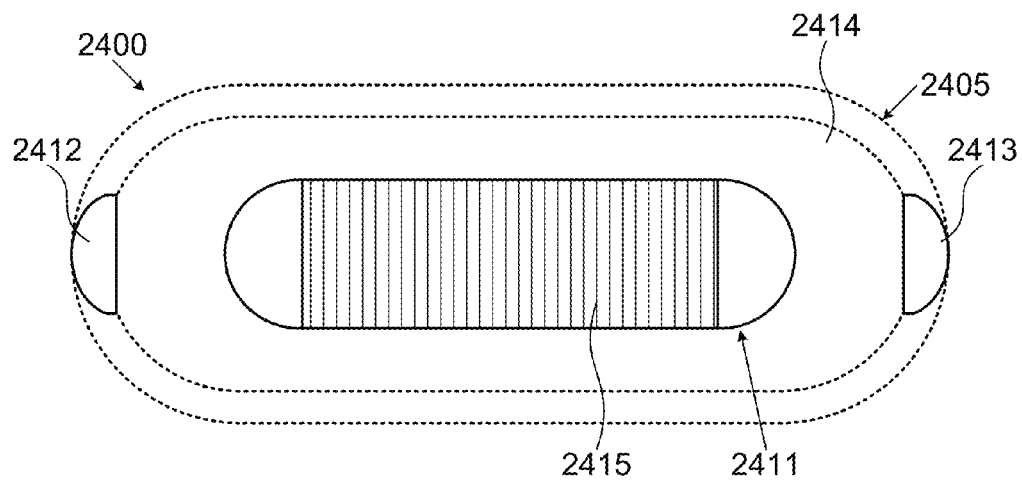
FIGS. 24A-24C are schematic illustrations of side views of an in-vivo device in accordance with an embodiment of the invention.
Figure 24B:
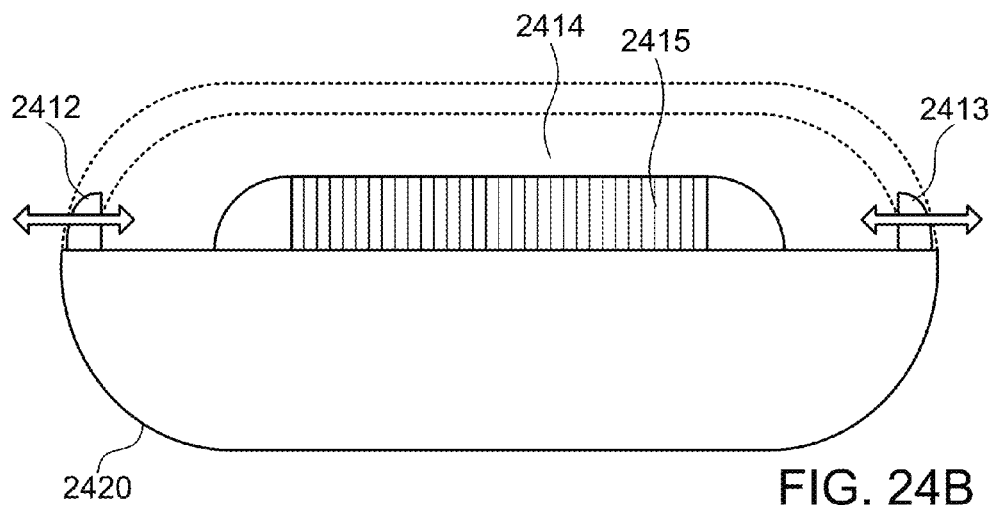
Figure 24C:
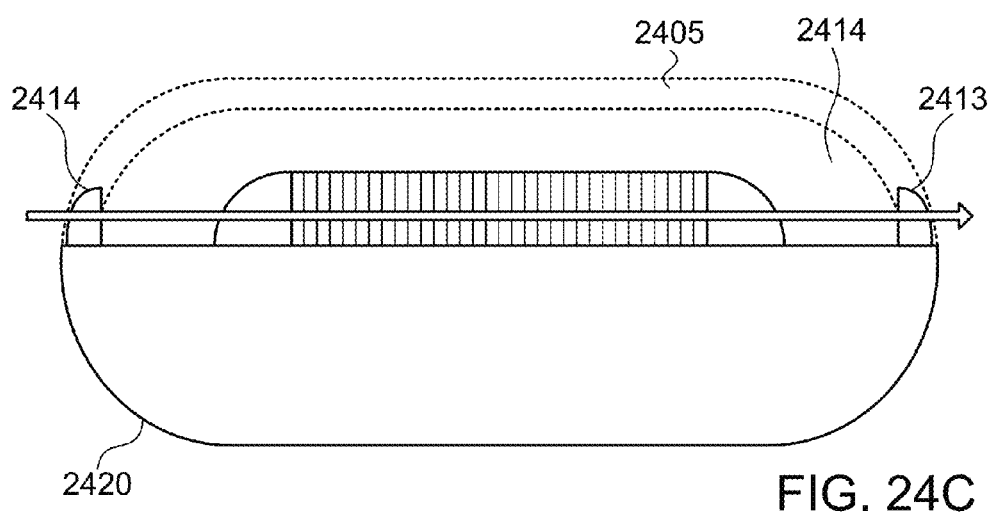

Reference is now made to FIGS. 24A-24C, which schematically illustrate side views of an in-vivo device in accordance with an embodiment of the invention. Device 2400 may comprise a blood sensing device 2411 located within space 2414 within cover 2405. Blood sensing device 2411 may comprise a passage passing through the longitudinal axis of device 2411, and illumination sources and a light detector may be housed within device 2411 for detecting presence of blood or blood residues within the fluids passing the passage. In some embodiments, the passage may be covered with a net or membrane 2415 for filtering the in-vivo fluids before they enter the passage for detection of presence of blood. The size of the openings or pores of net/membrane 2415 may be determined by the typical size of blood related particles. The size of the openings or pores of net/membrane 2415 may be large enough to allow entry (and exit) of blood related particles but small enough to prevent other particles from entering through net/membrane 2415, thus enabling a high signal to noise ratio during examination of in-vivo fluids.

In some embodiments, device 2411 may be covered with cover 2405 while space 2414 within which in-vivo fluids flow, may be defined between device 2411 and cover 2405. Cover 2405 may be made of either a rigid material or an elastic material, which may be squeezed when pressure is applied onto it. Cover 2405 may comprise two openings 2412 and 2413, typically located from opposing ends of the longitudinal axis of device 2400. When cover 2405 is made of a rigid material, it is designed to maintain its shape under pressure, for example, peristaltic pressure. Fluids may enter through either of openings 2412 or 2413 or through both, fluids and particles flowing within the fluids may then be filtered by net/membrane 2415 and only blood or blood residues (if present) may pass through the openings or pores of net 2415 and be examined by the illumination sources and the light detector located within device 2411.

In other embodiments, when cover 2405 is made of an elastic material, e.g., soft silicon, the silicon may collapse due to peristaltic pressure and may recover due to its elasticity, once pressure ceases to be applied onto device 2400. Cover 2405 being elastic facilitates fluid flow in and out of cover 2405 and thus into device 2411. When cover 2405 collapses, fluid is pushed outside device 2400 through opening 2412 and/or opening 2413. And when cover 2405 returns to its relaxed state, new fluids may enter device 2400 through openings 2412 and/or 2413 for new examination of presence of blood.

In some embodiments, as illustrated in FIGS. 24B-24C, device 2400 may comprise a protective portion 2420, which is made of rigid material. When cover 2405 is made of an elastic material, the entire cover 2405 might collapse over device 2411 and thus completely block passage of fluids through openings 2412 and 2413. In order to avoid such a scenario, protective portion 2420 may ensure that the section of cover 2405 that is covered with protective portion 2420 may not change its shape and may not collapse, so as to substantially block entry and exit of fluids in and out of device 2400.

FIG. 24B illustrates one embodiment in which fluid flow may be multi-directional, meaning that fluids may enter and exit either one of openings 2412 and 2413 (each opening has an arrow pointing both in and out of device 2400). FIG. 24C illustrates directional flow through device 2400, where fluids enter through one opening (e.g., opening 2412) and exit device 2400 through the other opening (e.g., opening 2413). Directional flow may be achieved by adding one-way valves at openings 2412 and 2413. Directional flow may increase probability of new fluids entering device 2400 and not fluids that were already examined by device 2411.

Figure 25A:
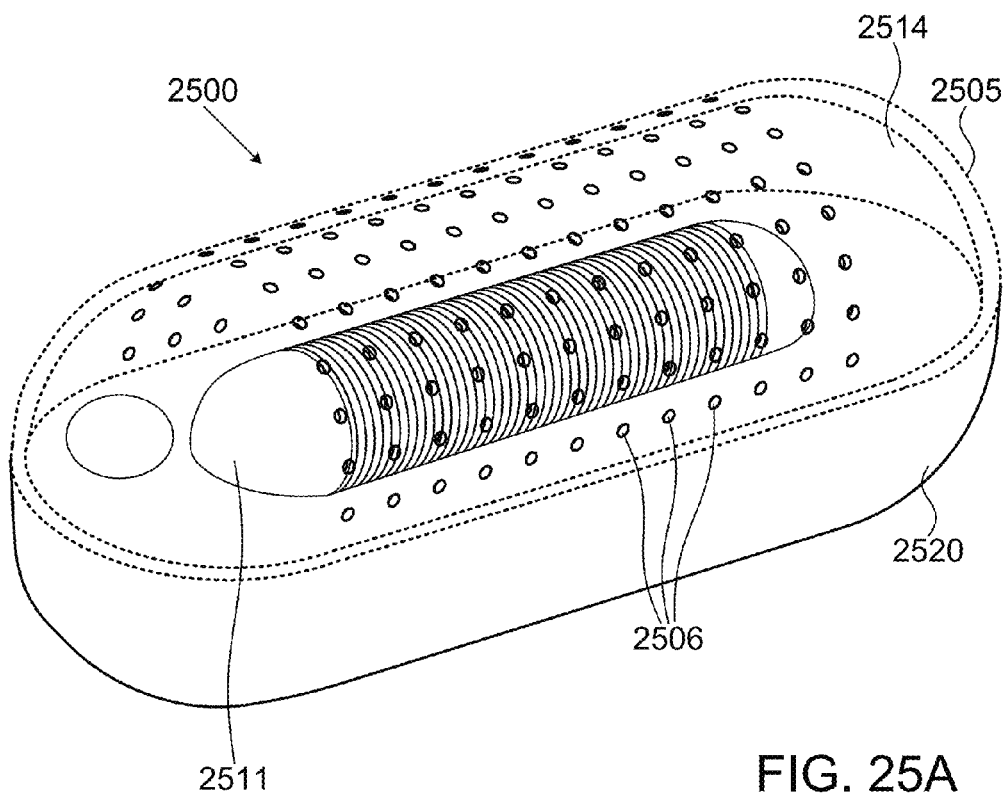
FIGS. 25A-25B are schematic illustrations of a side view and a front view, respectively, of an in-vivo device in accordance with an embodiment of the invention.
Figure 25B:
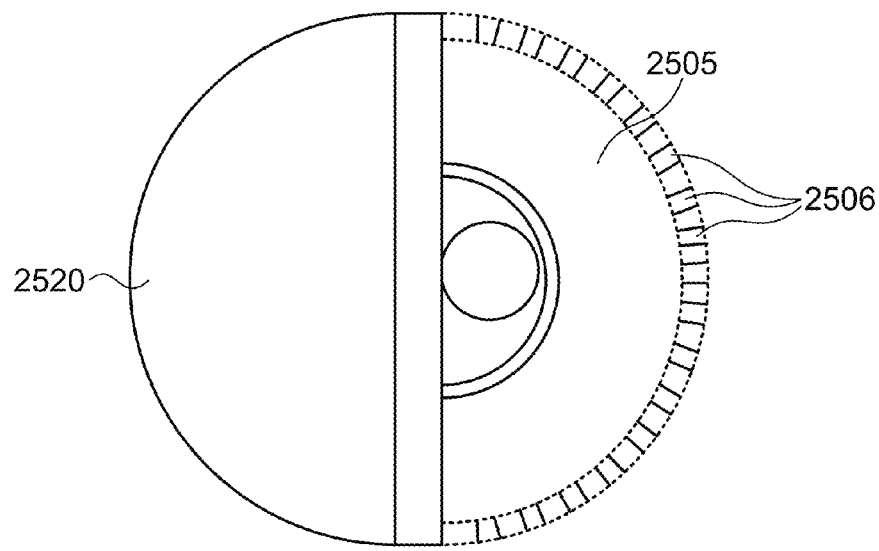

Reference is now made to FIGS. 25A-25B, which schematically illustrate a side view and a front view, respectively, of an in-vivo device in accordance with an embodiment of the invention. Device 2500 may comprise a blood sensing device 2511 located within space 2514 within cover 2505. Blood sensing device 2511 may comprise a passage passing all the way through the longitudinal axis of device 2511, and illumination sources and a light detector may be housed within device 2511 for detecting presence of blood or blood residues within the fluids passing the passage. In some embodiments, the passage may be covered with a net or membrane 2515 for filtering the in-vivo fluids before they enter the passage for detection of presence of blood. The size of the openings or pores of net/membrane 2515 may be determined by the typical size of blood related particles. The size of the openings or pores of net/membrane 2515 may be large enough to allow entry (and exit) of blood related particles but small enough to prevent other particles from entering through net/membrane 2515, thus enabling a high signal to noise ratio during examination of in-vivo fluids.

In some embodiments, device 2511 may be covered with cover 2505, while space 2514 within which in-vivo fluids may flow, may be defined between device 2511 and cover 2505. Cover 2505 may be made of a rigid material, e.g., rigid silicon, which doesn't change shape while under peristaltic pressure. However, in other embodiments, cover 2505 may be made of an elastic or pliable material, e.g., pliable silicon, which may change its shape due to applied pressure, e.g., peristaltic pressure. Cover 2505 may comprise be perforated, and thus comprise openings 2506, which may enable passage of fluids into the space created by cover 2505 and later into the passage of device 2511. The perforation of cover 2505 may create openings 2506 at a size that complies with the size of blood or blood related particles, and small enough so that feces, bubbles and particles unrelated to blood, may not enter. The perforation of cover 2505 may act as an additional filter of the in-vivo fluids prior to their entrance into the passage of device 2511.

In some embodiments, cover 2505 may cover the entire device 2511 while maintaining space 2514 surrounding device 2511, within which in-vivo fluids may flow after entering through cover 2505. However, in other embodiments, specifically when cover 2505 is made of an elastic material, perforated cover 2505 may cover only one section of device 2511, while another section is covered by a protective portion 2520. Protective portion 2520 may not comprise openings and may be made of a rigid material which is not pliable under pressure. Thus, device 2500 may have only cover 2505 be squeezed in the event of peristaltic wave passing by device 2500, while protective cover 2520 may maintain a space between device 2511 and protective portion 2520 through which in-vivo fluids may still flow. When a peristaltic wave passes by device 2500, fluids and particles may be pushed out of space 2514, making room for new fluids to enter later on. If cover 2505 is elastic and not rigid, then the entire cover 2505 may be squeezed and further facilitate fluid flow out of openings 2506, and out of device 2511. After the peristaltic wave moves past device 2500, cover 2505 may return to its relaxed state and new fluids and particles may enter through openings 2506 into space 2514 and into the passage, passing along the longitudinal axis of device 2511 in order to be examined for presence of blood or blood residues.

Figure 26A:
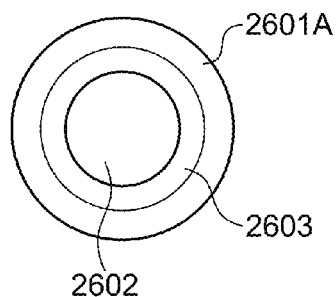
FIGS. 26A-26E are schematic illustrations of three front-views and two side views cross sections, respectively, of an in-vivo device in accordance with an embodiment of the invention.
Figure 26B:
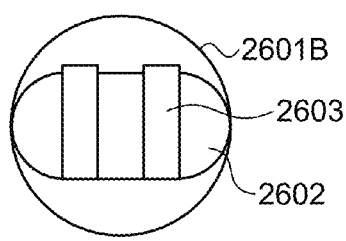

Reference is now made to FIGS. 26A-26E, which schematically illustrate three front-views and two side views cross sections, respectively, of an in-vivo device in accordance with an embodiment of the invention. Reference is now made to FIG. 26A, which schematically illustrates a front view of an in-vivo device in accordance with an embodiment of the invention. According to embodiments of the invention, in order to facilitate flow through tunnel or passage 2602, which passes along the entire longitudinal axis of housing 2601A of an in-vivo device, the ends of tunnel or passage 2602 may be designed to have rounded edges, which may achieve a smooth tunnel 2602 through which in-vivo fluids may flow. The center of passage 2602 may be concentric with the center of housing 2601A. In the small bowel, since the in-vivo device occupies the majority of the tract's cross-section area, fluids may be forced to flow through passage 2602. In FIG. 26B, a different front view of housing 2601B is illustrated. Housing 2601B may comprise a passage or tunnel 2602 passing through the entire longitudinal axis of housing 2601B. In some embodiments, the openings on both sides of passage 2602 may comprise one or more partitions 2603, which may further block entrance of tissue into passage 2602.

Figure 26C:
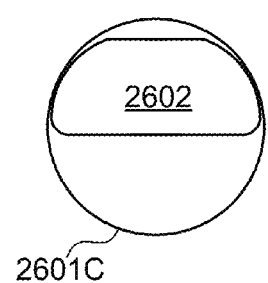

In FIG. 26C, the passage or tunnel 2602 may be located along a longitudinal axis of housing 2601C, but located off-center. That is, the center of passage 2602 is not concentric with the center of housing 2601C but is rather decentered with respect to housing 2601C. Passage 2602 being decentered from housing 2601C is easier to manufacture than, for example, the passages illustrated in FIGS. 26A-26B.

Figure 26D:
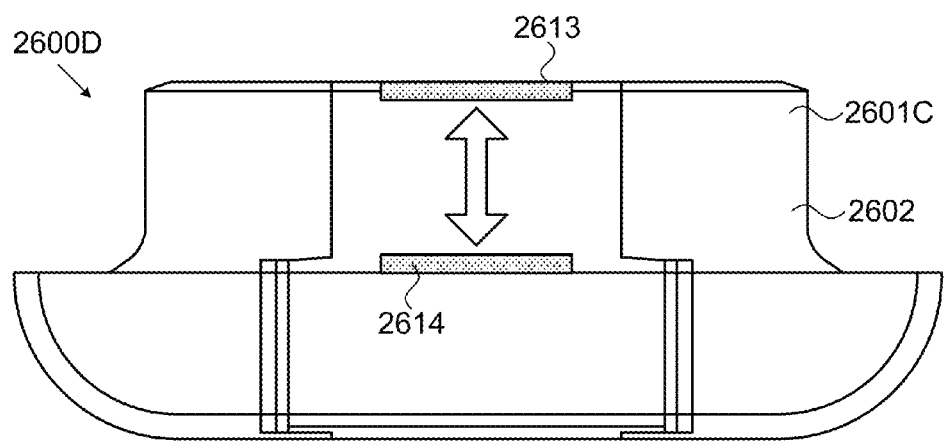
Figure 26E:
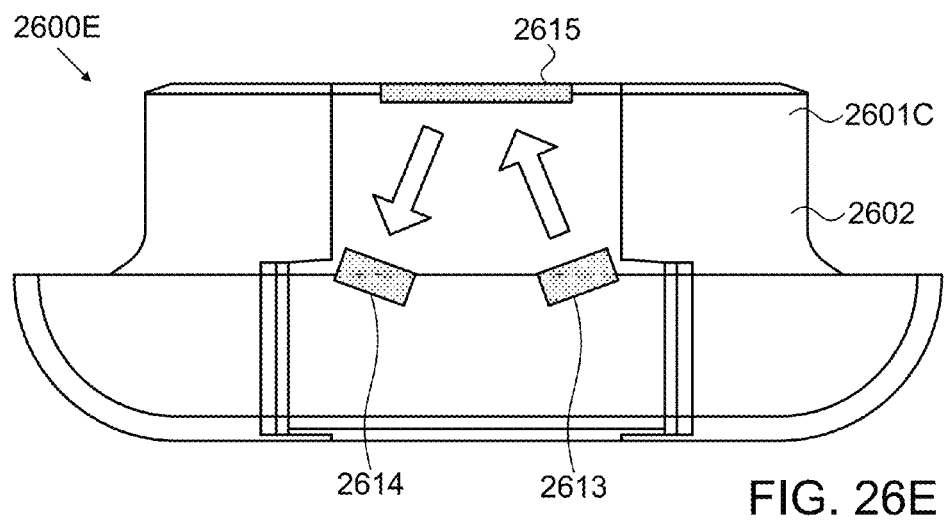

FIGS. 26D-26E illustrate side view cross sections of two possible embodiments comprising a decentered passage 2602. In device 2600D, passage 2602 may be located along a longitudinal axis of device 2600D but decentered from the longitudinal axis of symmetry of device 2600D. In some embodiments, as in device 2600D, illumination sources 2613 and light detector 2614 may be located on opposite sides of passage 2602. Light from illumination sources 2613 may pass through in-vivo fluids flowing through passage 2602 and may be detected by light detector 2614. In other embodiments, as illustrated in FIG. 26E, device 2600E may comprise a passage 2602 that may be located along a longitudinal axis of device 2600E but decentered from the longitudinal axis of symmetry of device 2600E. However, unlike device 2600D, device 2600E may comprise illumination sources 2613 located at the same side of passage 2602 as light detector 2614. In order for light to pass through in-vivo fluids flowing through passage 2602 and reach light detector 2614, a reflector 2615 may be located opposite illumination sources 2613 and light detector 2614. Reflector 2615 may be located behind a side of passage 2602 which is opposite the side behind which illumination sources 2613 and light detector 2614 are located. Light may emanate from illumination sources 2613, reach reflector 2615, and then be reflected towards light detector 2614 for detection of light signals.

Figure 27A:
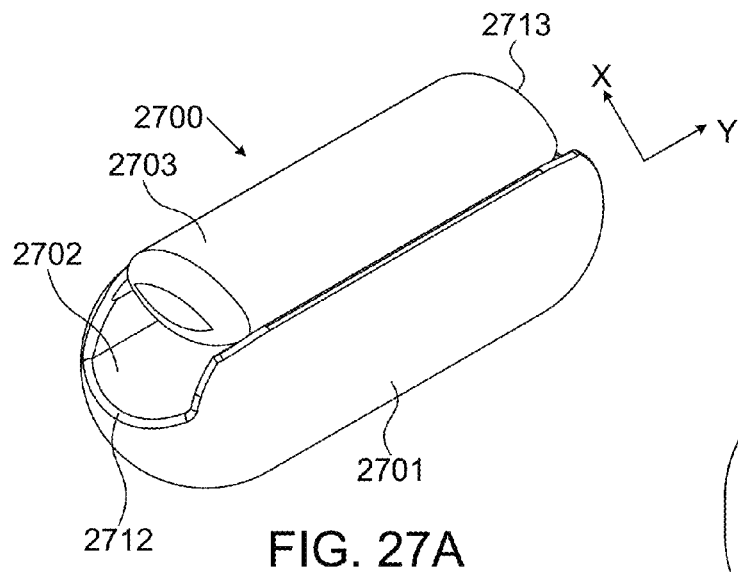
FIGS. 27A-27B are schematic illustrations of a side view and a front view, respectively, of an in-vivo device in accordance with an embodiment of the invention.
Figure 27B:
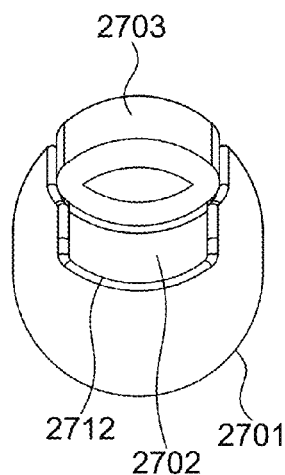

Reference is now made to FIGS. 27A-27B, which schematically illustrate a side view and a front view, respectively, of an in-vivo device in accordance with an embodiment of the invention. In-vivo device 2700 may be a swallowable device. Device 2700 may comprise an elongated housing 2701. Housing 2701 may comprise a passage or tunnel 2702, which may pass along the longitudinal axis (axis Y) of housing 2701, from one end of housing 2701 until the opposite end of housing 2701. In some embodiments, the sensing area wherein illumination sources and a light detector are typically located one across the other, may be located at an equal distance from either ends 2712 and 2713 of housing 2701. Assuming each end 2712 and 2713 comprises an opening the size of 3-5 mm, then the sensing area should be located at an equal distance of at least 5 mm from each of the ends of housing 2701, i.e., 5 mm away from end 2712 and 5 mm away from end 2713.

In some embodiments, device 2700 may comprise balloon 2703, which may change its shape due to applied pressure. Pressure applied onto balloon 2703 may either be direct pressure from villi collapsing around device 2700 during peristaltic wave, or may be indirect pressure caused by peristaltic waves but applied onto device 2700 through fluids flowing around device 2700, and not necessarily through GI tissue contacting device 2700. During peristaltic wave, balloon 2703 may be squeezed and may transfer the pressure towards the side of balloon 2703 which is in contact with passage 2702, which may cause fluids present within passage 2702 to be pushed outside of either or both of openings 2712 and 2713. When no pressure is applied onto device 2700, then balloon 2703 may return to its relaxed state which is less pushed into passage 2702 such that new fluids may enter through either or both of openings 2712 and 2713, for detection of blood or blood residues. Balloon 2703 may enable active fluid flow through passage 2702 instead of passive flow of fluids through passage 2702, since the active and pressurized balloon 2703 facilitates flow due to its pumping, pushing, and pressure transferring motions.

Figure 28A:
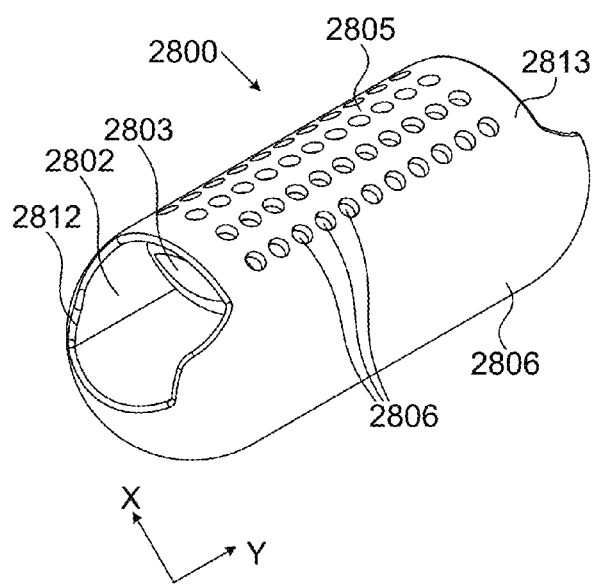
FIGS. 28A-28B are schematic illustrations of a side view and a front view, respectively, of an in-vivo device in accordance with an embodiment of the invention.
Figure 28B:
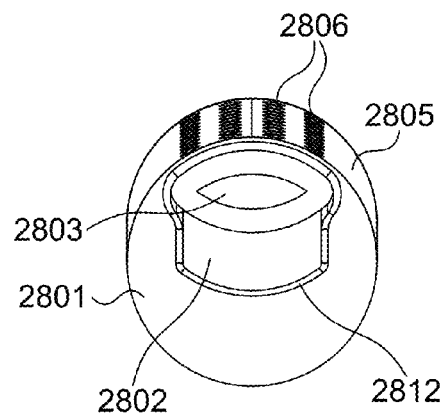

Reference is now made to FIGS. 28A-28B, which schematically illustrate a side view and a front view, respectively, of an in-vivo device in accordance with an embodiment of the invention. In-vivo device 2800 may be a swallowable device. Device 2800 may comprise an elongated housing 2801. Housing 2801 may comprise a passage or tunnel 2802, which may pass along the longitudinal axis (axis Y) of housing 2801, from one end of housing 2801 until the opposite end of housing 2801. In some embodiments, the sensing area wherein illumination sources and a light detector are typically located one across the other may be located at an equal distance from either ends 2812 and 2813 of housing 2801. Assuming each end 2812 and 2813 comprises an opening the size of 3-5 mm, then the sensing area should be located at an equal distance of at least 5 mm from each of the ends of housing 2801, i.e., 5 mm away from end 2812 and 5 mm away from end 2813.

In some embodiments, device 2800 may comprise balloon 2803, which may change its shape due to applied pressure, similarly to balloon 2703 of device 2700 (FIGS. 27A-27B). However, device 2800 may further comprise a cover 2805 which may be located over balloon 2803 opposite the side of balloon 2803, which may be in contact with passage 2802. Cover 2805 may be in contact with balloon 2803 from one side and in contact with the GI tissue from the other side. In some embodiments, cover 2805 may comprise holes or openings 2806. Openings 2806 may enable GI fluids to transfer surrounding GI pressure towards balloon 2803, which may change the shape of balloon 2803 to be pushed towards passage 2802 and thus cause examined fluids to exit device 2800; once external pressure is reduced, balloon 2803 may return to its less squeezed shape, thus opening passage 2802 for entry of new fluids into and through passage 2802.

According to some embodiments, although device 2700 (FIGS. 27A-27B) is more sensitive to direct pressure (caused by GI tissue, e.g., villi) as well as to indirect pressure (transferred to balloon 2703 by GI fluids) with respect to balloon 2803, since balloon 2803 is covered by cover 2805 and is not in direct contact with the GI environment, device 2800 is easier to manufacture compared to device 2700.

Figure 29A:
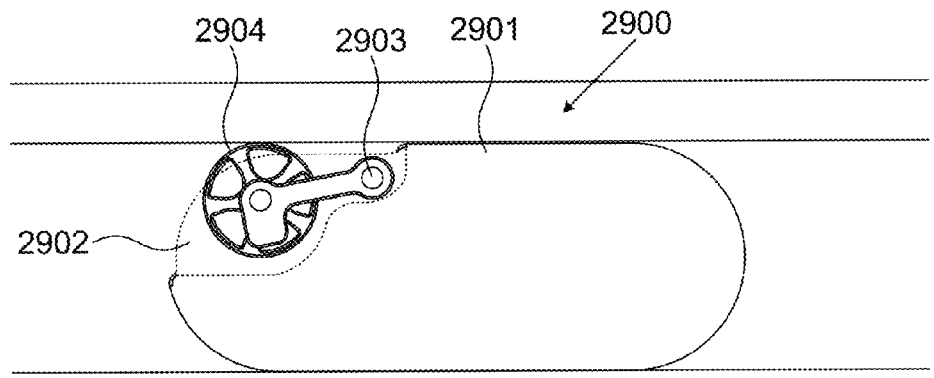
FIGS. 29A-29C are schematic illustrations of two side views and close side view, respectively, of an in-vivo device in accordance with an embodiment of the invention.
Figure 29B:
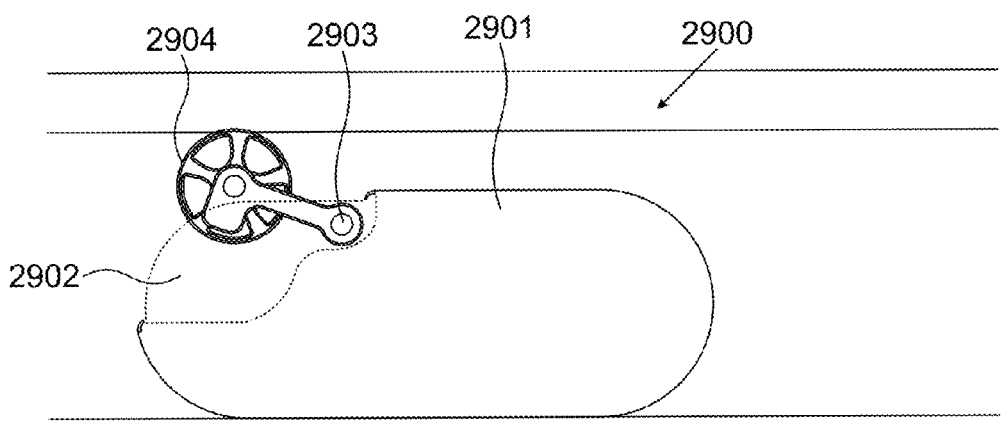
Figure 29C:
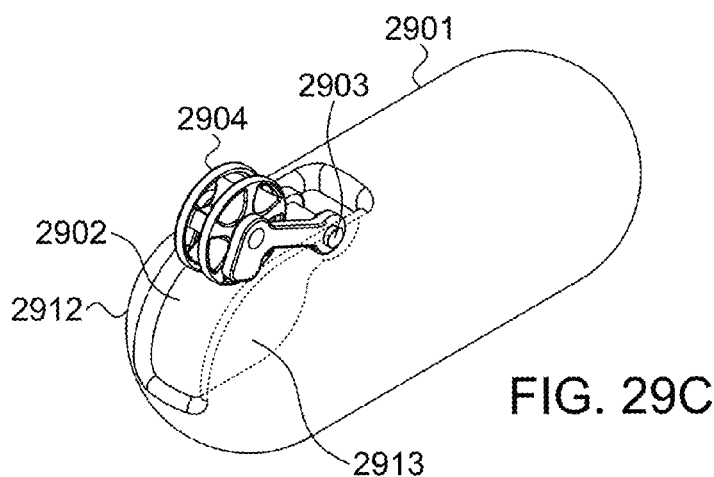

Reference is now made to FIGS. 29A-29C, which schematically illustrate two side views and close side view, respectively, of an in-vivo device in accordance with an embodiment of the invention. Device 2900 may be a swallowable in vivo device. Device 2900 may comprise housing 2901. Housing 2901 may have an elongated shape. As illustrated in FIG. 29C, device 2900 may comprise an opening 2902, which may be located between two walls 2912 and 2913. Opening 2902 need not pass through the entire elongated housing 2901 (e.g., through a longitudinal axis of housing 2901) but may only be open at one of the ends of housing 2901. Illumination sources (not shown) may be located on one of walls 2912 or 2913, and a light detector (not shown) may be located on one of walls 2912 or 2913, one of which is not already occupied by the illumination sources. In some embodiments, the illumination sources and the light detector may be located one across the other, both on the side of walls 2912 and 2913, which is in contact with fluids flowing through opening 2902. Light at different narrow wavelengths, which emanates from the illumination sources, may pass through fluids flowing within opening 2902, and may reach the light detector for detection of presence of blood.

In order to facilitate flow of fluids through opening 2902, housing 2901 may comprise wheel 2904, located within opening 2902. In some embodiments, wheel 2904 may turn when in contact with GI tissue. When GI tissue is in close proximity to wheel 2904, such that the tissue touches wheel 2904, the wheel may be turned against the tissue. The turning of wheel 2904 may cause fluids present within opening 2902 and fluids in close proximity to opening 2902 to mix. Thus, when wheel 2904 turns, it may cause some of the fluids to exit opening 2902 and may cause some fluids to enter opening 2902. When wheel 2904 turns and mixes the fluids within and near opening 2902, it may be assumed that fluids, which were already examined by the light detector will exit opening 2902, while some "new" fluids, which weren't examined yet, may enter opening 2902 and be examined for presence of blood or blood residues.

FIG. 29A illustrates the GI tissue walls surrounding device 2900, such that wheel 2904 may touch the GI tissue wall. This may be the case in the small bowel, when the tract is relatively narrow and the diameter of device 2900 may conform to the diameter of the small bowel's tract. FIG. 29B illustrates the GI tissue wall located at a distance from housing 2901, at least at a distance from the section of housing 2901 which comprises wheel 2904. This may be the case in the colon, where the colon tract's diameter is larger than the diameter of device 2900. Therefore, in some embodiments, wheel 2904 may be connected to a pivot or hinge 2903 that may be moved so as to provide various opening angles to wheel 2904 in order to bring wheel 2904 in close proximity to the GI tissue until wheel 2904 touches the tissue. Once wheel 2904 touches the tissue, the tissue may turn wheel 2904, which may mix the examined and new fluids out of and into opening 2902. Control on the appropriate opening angles required by pivot 2903 until contact is made with the GI tissue, may be determined either by an external operator or by a closed loop within device 2900, assuming there is indication when contact is made between wheel 2904 and the GI tissue (e.g., by various "touch" sensors located along wheel 2904).

Figure 30A:
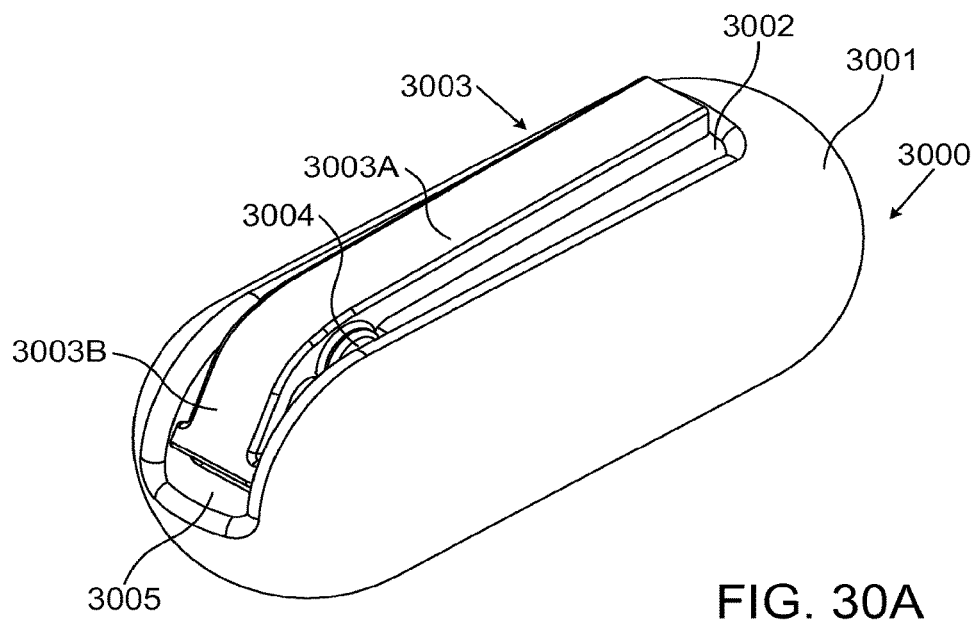
FIGS. 30A-30B are schematic illustrations of side views of an in-vivo device in accordance with an embodiment of the invention.
Figure 30B:
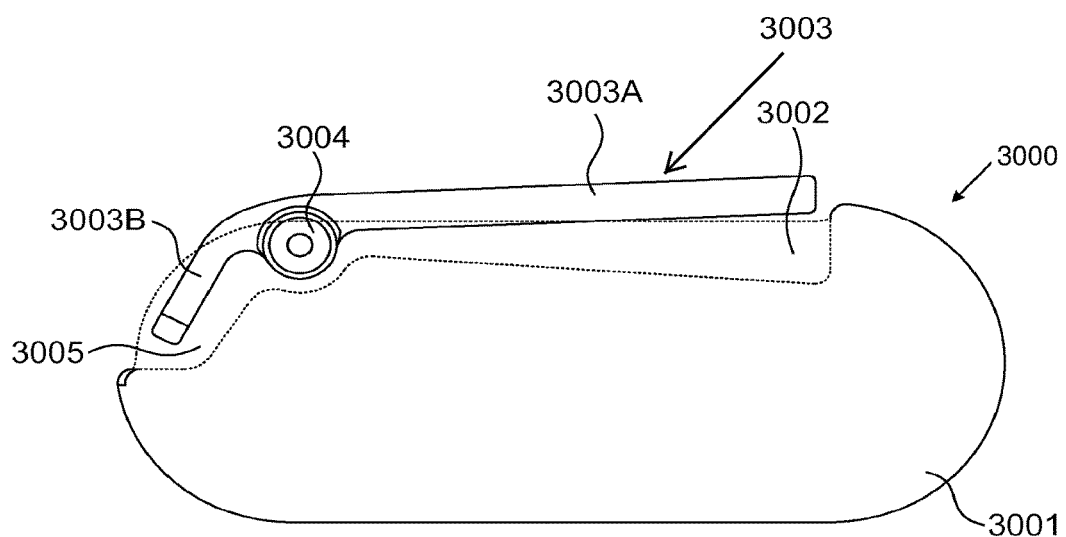

Reference is now made to FIGS. 30A-30B, which schematically illustrate side views of an in-vivo device in accordance with an embodiment of the invention. Device 3000 may be a swallowable in-vivo device. Device 3000 may comprise housing 3001, which may have an elongated shape, e.g., a cylinder with rounded edges, a capsule, or any other shape that is easy to swallow and would easily pass through the GI tract. Device 3000 may comprise an opening or passage 3002 into which and through which in-vivo fluids may enter and exit. In some embodiments, passage 3002 may pass through a longitudinal axis of housing 3001 from one end of housing 3001 to the other end of housing 3001 along the longitudinal axis. In other embodiments, passage 3002 need not pass along the entire longitudinal axis of housing 3001 but may rather pass along a section of housing 3001, although still along the longitudinal axis of housing 3001. On one side of passage 3002 may be illumination sources (not shown) for illuminating fluids within passage 3002, e.g., at different narrow wavelengths, and on the other side of passage 3002 may be a light detector (not shown) for detecting wavelengths of light that passed through the fluids.

In some embodiments, device 3000 may comprise a moveable arm 3003, which may comprise a pivot 3004 around which arm 3003 rotates. Arm 3003 may comprise two sections; section 3003A is the section of arm 3003 that may enter and exit passage 3002, and section 3003B is the section of arm 3003 that is located at one of the ends of housing 3001 and comprises a respective dent 3005 into which section 3003B may enter or exit. When section 3003B is located within dent 3005, then section 3003A may be located at a distance from passage 3002, and when section 3003B is located outside of or at a distance from dent 3005, section 3003A may be located within passage 3002. Moveable arm 3003 may rotate around pivot 3004 when tissue is pushed against arm 3003. For example, when a peristaltic wave passes through the GI tissue that is in close proximity to device 3000, and pressure is applied onto section 3003A, then section 3003A may be pushed into passage 3002, and section 3003B may be pushed at a distance from dent 3005. If pressure is applied onto section 3003B during peristaltic wave, then section 3003B may be pushed into dent 3005 and thus section 3003A would be distanced from passage 3002. Since pressure may be applied onto either of the sections of arm 3003, and then onto the other section of arm 3003, arm 3003 may freely rotate around pivot 3004 whenever a peristaltic wave passes by device 3000. Rotation of arm 3003 around pivot 3004 may cause fluids passing through passage 3002 to mix and may cause fluids to enter and exit into and out of passage 3002. Thus, "new" fluids that were not examined yet for presence of blood may be examined following the mixing motion caused by rotation of arm 3003 around pivot 3004.

Figures 31A, 31B:
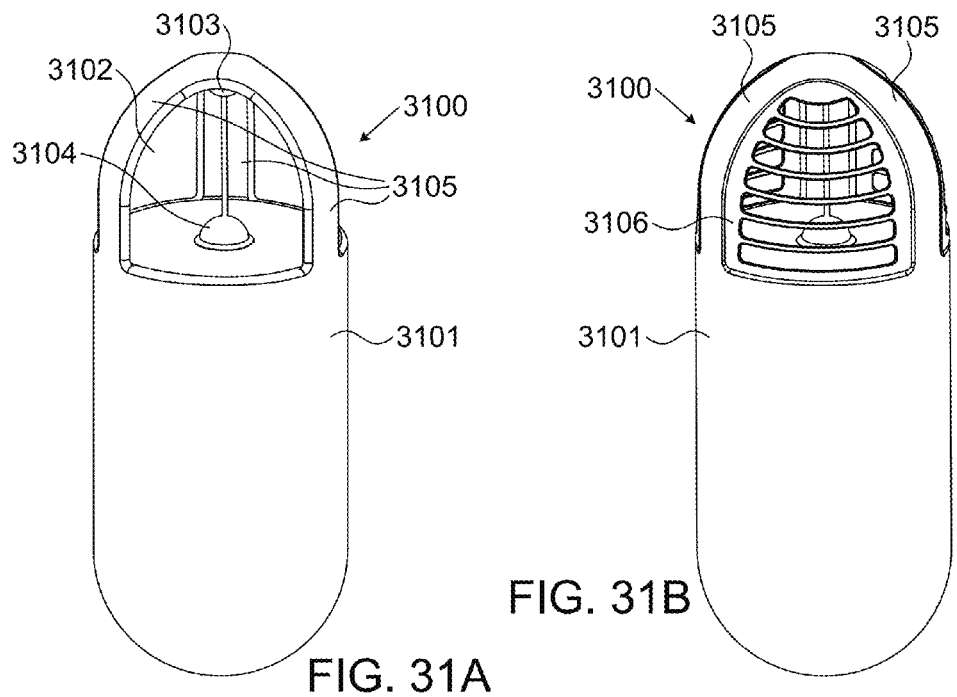
FIGS. 31A-31B are schematic illustrations of side views of an in-vivo device in accordance with an embodiment of the invention.

Reference is now made to FIGS. 31A-31B, which schematically illustrate side views of an in-vivo device in accordance with an embodiment of the invention. Device 3100 may be a swallowable in-vivo device. Device 3100 may comprise housing 3101. Housing 3101 may comprise one end comprising an imager (not shown) and one end for sensing presence of blood.

Reference is now made to FIG. 31A. The end of housing 3101 that is for sensing presence of blood may comprise at least two arms 3105 which project from housing 3101 and meet at the top end of housing 3101, such that between arms 3105 there is a space 3102 through which in-vivo fluids may flow. In some embodiments, in order to detect presence of blood, illumination sources 3103 may be located at the top end of housing 3101, where arms 3105 meet, and a light detector 3104 may be located within housing 3101 across illumination sources 3103. Light of different wavelengths may emanate from illumination sources 3103, pass through fluids flowing within space 3102, and be detected by light detector 3104, which is located directly opposite to illumination sources 3103. In other embodiments, light detector 3104 may be located where arms 3105 meet, while illumination sources 3103 may be located within housing 3101 across light detector 3104, as long as the sensing units are located one across the other, or one opposite the other.

In some embodiments, as shown in FIG. 31A, space 3102 may be "interrupted" only by arms 3105. The size of arms 3105 may be determined by the size and amount of circuitry that is required to pass through arms 3105 in order to connect the illumination sources 3103 and light detector 3104 to the rest of the electronic components of device 3100.

Reference is now made to FIG. 31B, which schematically illustrates device 3100 with the addition of bars 3106 for blocking entry of tissue and other large particles into space 3102. The size of bars 3106 and the distance between each of the bars may be determined by the size of particles that should be blocked from entering space 3102.

Figures 32A, 32B, 32C:
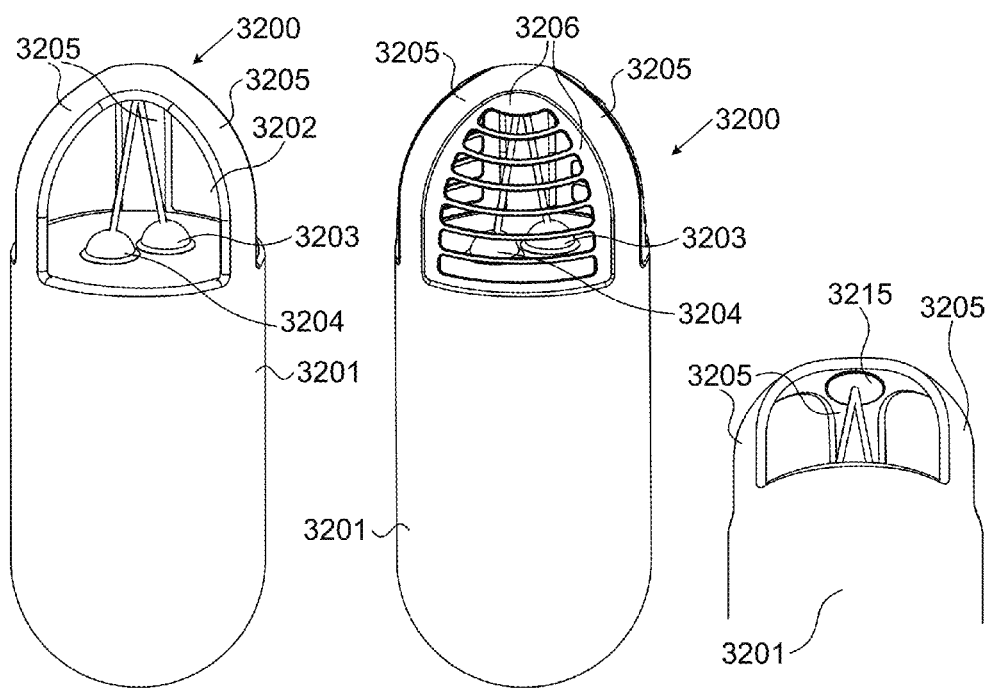
FIGS. 32A-32C are schematic illustrations of side views of an in-vivo device in accordance with an embodiment of the invention.

Reference is now made to FIGS. 32A-32C, which schematically illustrate side views of an in-vivo device in accordance with an embodiment of the invention. Device 3200 may be a swallowable in-vivo device. Device 3200 may comprise housing 3201. Housing 3201 may comprise one end comprising an imager (not shown) and one end for sensing presence of blood.

Reference is now made to FIG. 32A, which illustrates a device similar to device 3100 (FIG. 31A). Similarly to housing 3101, the end of housing 3201 that is for sensing presence of blood may comprise at least two arms 3205 (for example, three arms 3105, as illustrated in FIG. 32A) which project housing 3201 and meet at the top end of housing 3201, such that between arms 3205 there is space 3202 through which in-vivo fluids may flow.

In some embodiments, in order to detect presence of blood, housing 3201 may comprise illumination sources and a light detector. However, unlike device 3100, device 3200 may comprise such components at a different location along housing 3201. In some embodiments, illumination sources 3203 as well as light detector 3104 may be located within housing 3201 below the canopy created by arms 3205. Illumination sources 3203 and light detector 3204 may be located side by side, below arms 3205. In order for light of different wavelengths to pass through the in-vivo fluids flowing within space 3202 and then be detected by light detector 3204, when illumination sources 3203 are positioned side by side with light detector 3204, a reflector 3215 is required reflect light reaching it from illumination sources 3203 towards light detector 3204. As illustrated in FIG. 32C, reflector 3215 may be located at the meeting point of arms 3205, which is located across illumination sources 3203 and light detector 3204. Thus, light of different wavelengths emanating from illumination sources 3203 may reach reflector 3215 and be reflected off reflector 3215 towards light detector 3204, while passing through in-vivo fluids present within space 3202.

In some embodiments, as shown in FIG. 31A, space 3202 may be "interrupted" only by arms 3205. However, unlike device 3100, in which the size of arms 3105 is determined by the amount of circuitry that is required to pass through arms 3105 in order to connect the illumination sources 3103 and light detector 3104 to the rest of the electronic components of device 3100, arms 3205 need not pass any circuitry, which makes device 3200 easier to produce.

Reference is now made to FIG. 32B, which schematically illustrates device 3200 with the addition of bars 3206 for blocking entry of tissue and other large particles into space 3202. The size of bars 3206 and the distance between each of the bars may be determined by the size of particles that should be blocked from entering space 3202.

Figure 33:
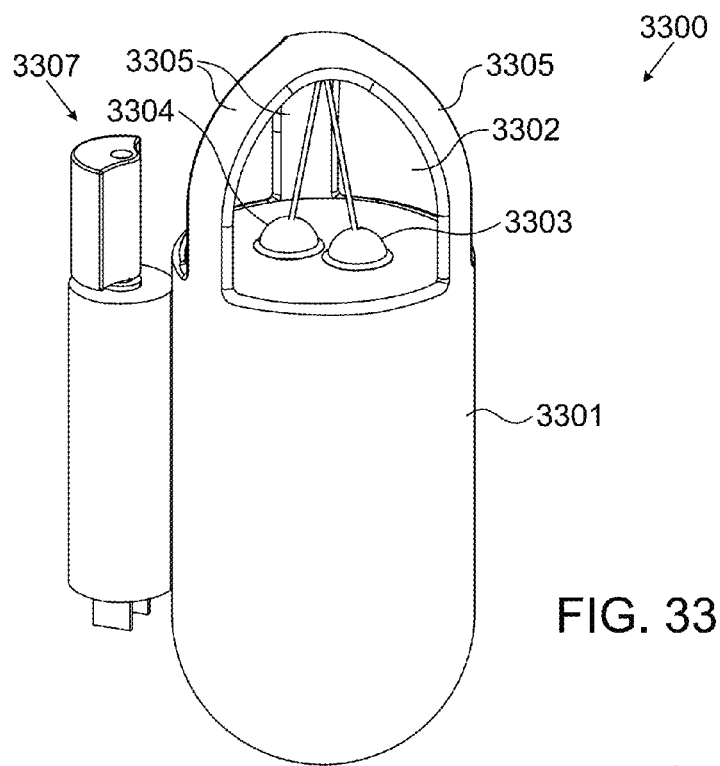
FIG. 33 is a schematic illustration of a side view of an in-vivo device in accordance with a thirtieth embodiment of the invention.

Reference is now made to FIG. 33, which schematically illustrates a side view of an in-vivo device in accordance with an embodiment of the invention. Device 3300 may be a swallowable in-vivo device. Device 3300 may comprise housing 3301. Housing 3301 may comprise one end comprising an imager (not shown) and one end for sensing presence of blood. Similarly to housing 3101 (FIG. 31A), the end of housing 3301, which is for sensing presence of blood may comprise at least two arms 3305 (for example, three arms 3305, as illustrated in FIG. 33) which project from housing 3301 and meet at the top end of housing 3301, such that between arms 3305 there is space 3302 through which in-vivo fluids may flow.

In some embodiments, housing 3301 may comprise illumination sources 3303 located side by side with light detector 3304, while a reflector (not shown) may be located across illumination sources 3303 and light detector 3304, at the point where arms 3305 meet, similarly to the components' positioning in device 3200 (FIGS. 32A, 32C).

Device 3300 may further comprise vibrating motor 3307. Vibrating motor 3307 may be designed to occasionally vibrate and may thus cause particles such as feces that may be caught within space 3302 to exit space 3302 through the openings between arms 3305. Particles may enter into space 3302, and if fluid flow isn't sufficient, these particles may get stuck and occupy space 3302 and thus interrupt free passage of light from illumination sources 3303 towards the reflector and then towards light detector 3304. Since such particles may interfere with blood detection, a vibrating motor that may cause such particles to exit and free space 3302 to free fluid flow may be a good solution for overcoming such a problem.

Figure 34A:
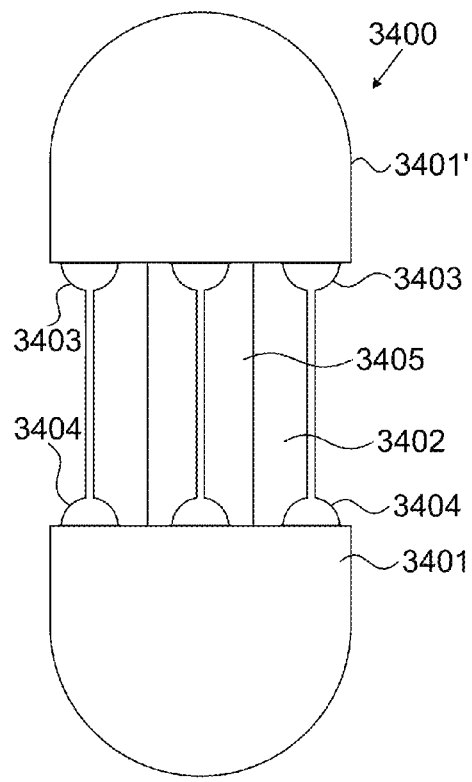
FIGS. 34A-34B are schematic illustrations of side views of an in-vivo device in accordance with an embodiment of the invention.
Figure 34B:
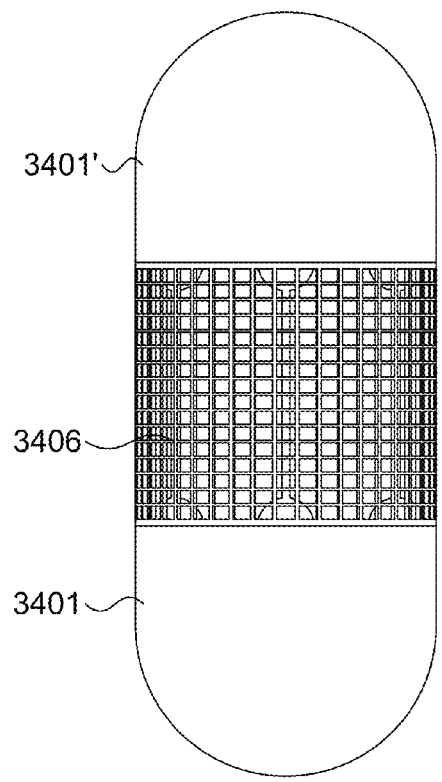

Reference is now made to FIGS. 34A-34B, which schematically illustrate side views of an in-vivo device in accordance with an embodiment of the invention. Device 3400 may be a swallowable in-vivo device. Device 3400 may comprise a housing comprising three portions; a first portion 3401, a second portion 3401' and a third portion 3405. Portion 3401 and portion 3401' may both be connected to portion 3405. Each of portions 3401 and 3401' may have a rounded shape, e.g., half a sphere or a mushroom, though other shapes are possible. The rounded edge of each of portions 3401 and 3401' may be pointed towards the surroundings of device 3400, while the flat surface of each of portions 3401 and 3401' may be in contact with portion 3405. Device 3400 may thus comprise space 3402 in between portions 3401 and 3401'. Through space 3402 may flow in-vivo fluids, and these fluids may be examined for the presence of blood.

Device 3400 may further comprise illumination sources 3403 and light detector 3404 for detecting presence of blood or blood residues. The illumination sources 3403 may be located on the flat surface of either of portions 3401 or 3401', while the corresponding light detector may be located on the flat surface of the opposing portion, whether 3401 or 3401'. In some embodiments, there may be more than one light detector 3404 and more than one group of illumination sources 3403 such that a plurality of light detectors corresponding to a plurality of illumination sources 3403 may be located one across the other. For example, portion 3401' may comprise a plurality of illumination sources 3403 located on the flat surface of portion 3401' around the connecting point between portion 3401' to portion 3405. And portion 3401 may comprise a plurality of light detectors 3404 located on the flat surface of portion 3401, while surrounding the connecting point of portion 3401 to portion 3405. Illumination sources 3403 may be located opposite and across light detectors 3404, so that light may pass from illumination sources 3403 through in-vivo fluids and be detected by respective light detectors 3404. Since device 3400 comprises more than one light detector 3404 and more than one group of illumination source 3403, even if one light path is blocked by flowing particles, there would still be light paths free for detection of blood.

Reference is now made to FIG. 34B, which schematically illustrates device 3400 with the addition of net or mesh 3406. Net or mesh 3406 may be located onto space 3402 in order to block entrance of particles of a certain size into space 3402, since the presence of particles unrelated to blood or blood residues may interrupt the light path between illumination source 3403 and light detectors 3404, which may interrupt detection of blood within in-vivo fluids flowing through space 3402. The size of the holes of mesh or net 3406 may be determined by the size of blood related particles, such that the size of the holes in mesh 3406 may be larger than the size of blood related particles, yet smaller than particles larger than blood related particles. Net or mesh 3406 may, of course, also prevent tissue from entering space 3402, thus avoiding false positive readings by light detectors 3404.

Reference is now made to FIG. 35, which schematically illustrates a side view of an in-vivo device, in accordance with an embodiment of the invention. FIG. 35 illustrates device 3500 which may comprise housing 3501. Housing 3501 may comprise a gap 3502 through which in-vivo fluids may enter and exit. Gap 3502 may be defined between two walls, wall 3512 and wall 3513. One of walls 3512 and 3513 may comprise illumination sources (not shown) for illuminating the fluids passing through gap 3502, while the other wall, located opposite the wall that comprises the illumination sources, may comprise a light detector for detecting the light after the light passed through the fluids. The illumination sources and the light detector may be located one across the other, while fluids are present in between these components. Device 3500 may further comprise a pump 3506 which may pump air (or clear fluids) through tube 3507 into gap 3502 in order to clear gap 3502 following it being clogged by particles. Air or clear fluids which are forcedly pushed out through tube 3506 may clear any content blocking gap 3502, and may enable new in-vivo fluids to enter gap 3502 for detection of presence of blood.

Reference is now made to FIGS. 36A-36B, which schematically illustrate side views of an in-vivo device, in accordance with an embodiment of the invention. FIGS. 36A-36B illustrate device 3600, which may comprise a gap 3602 between two opposing walls 3612 and 3613, similarly to device 3500 (FIG. 35). The difference is that instead pump 3506, device 3600 may comprise a wheel 3606 that may turn and mix fluids within gap 3602 such to ensure continuous entrance of new fluids and exit of fluids that were already examined for presence of blood.

Figure 37A:
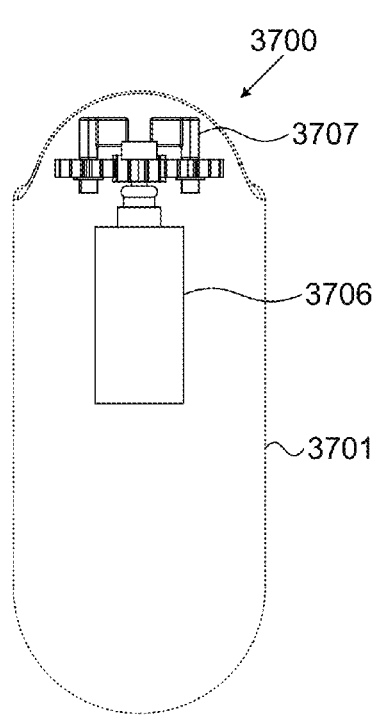
FIGS. 37A-37C are schematic illustrations of side views of an in-vivo device, in accordance with an embodiment of the invention.
Figure 37B:
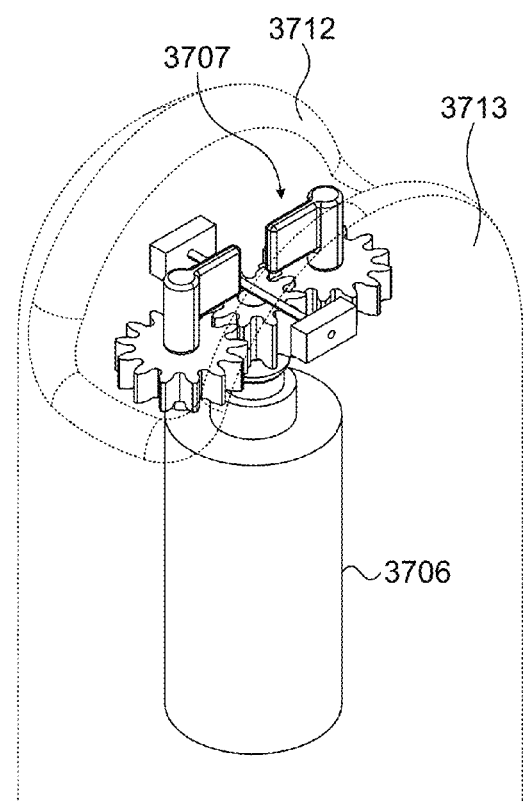
Figure 37C:
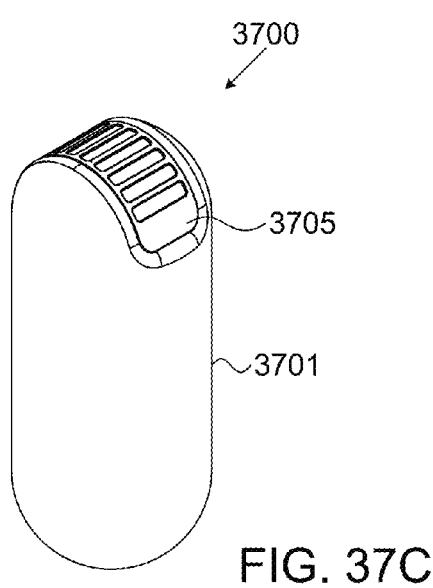

Reference is now made to FIGS. 37A-37C, which schematically illustrate side views of an in-vivo device, in accordance with an embodiment of the invention. FIGS. 37A-37C illustrate device 3700, which may be a swallowable in-vivo device, similar to device 3500 (FIG. 35). Similarly to device 3500, device 3700 may comprise a gap through which in-vivo fluids may enter and be detected for presence of blood, and through which fluids may exit following examination. Instead of pump 3506 and tube 3507, housing 3701 may comprise a motor 3706 that may operate mechanism 3707. Mechanism 3707 may comprise a plurality of cog wheels which may turn one or more racks 3708. Once racks 3708 are moved within gap 3702 from one side to the other, the fluids flowing within gap 3702 may be mixed, which may facilitate better fluid flow out of gap 3702 and into gap 3702. Thus movement of racks 3702 may enable better flow of fluids that were already examined out of gap 3702 and enable better fluid flow of new fluids into gap 3702 for detection of presence of blood or blood residues. FIG. 37C illustrates a cage or bars 3705 located on top of gap 3702 in order to block entrance of tissue, bubbles and particles of a certain size. The size of space between the bars of cage 3705 may be determined by the typical size of blood related particles, such that only particles of the same size of blood related particles (or smaller) may enter gap 3702. Blocking entrance of large particles and tissue may be beneficial in order to achieve a cleaner signal detected by the light detector, which may be located within gap 3702.

Figure 38A:
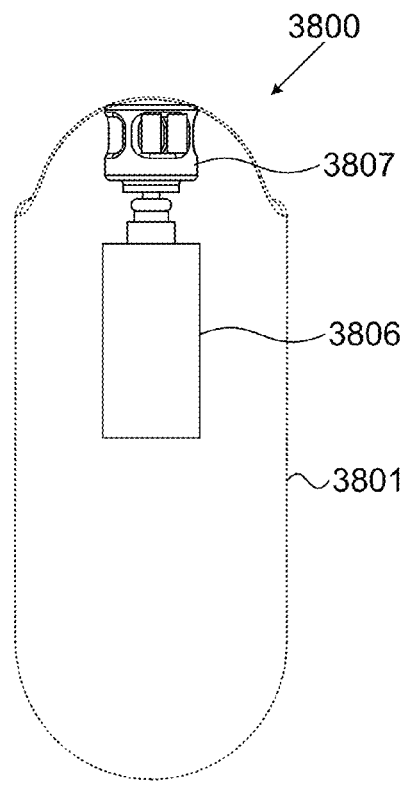
FIGS. 38A-38C are schematic illustrations of side views of an in-vivo device, in accordance with an embodiment of the invention.
Figure 38B:
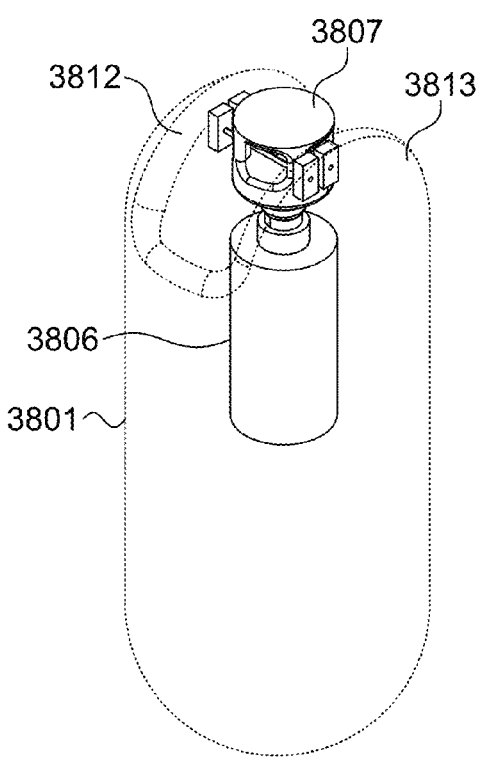
Figure 38C:
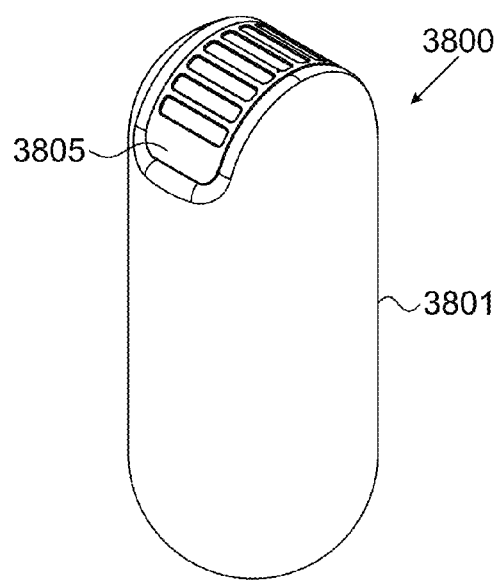

Reference is now made to FIGS. 38A-38C, which schematically illustrate side views of an in-vivo device, in accordance with an embodiment of the invention. FIGS. 38A-38C illustrate in-vivo device 3800, which may be similar to device 3500 (FIG. 35) since it may also comprise a gap 3802 through which in-vivo fluids may flow. Gap 3802 may be defined between two opposing walls 3812 and 3813 (FIG. 38B). On one of the walls may be illuminations sources while on the opposing wall may be a light detector. Light may emanate from the illumination sources, pass through the fluids within gap 3802 and reach the light detector. Device 3800 may comprise a motor 3806, which may turn an ultrasonic transducer 3807 within gap 3802. Ultrasonic transducer 3807 may be used to clean particles blocking the passage of light from the illumination sources towards the light detector. Ultrasonic waves may be used to cause the blocking particles to vibrate and break into smaller particles that may easily exit through gap 3802. Motor 3806 may turn ultrasonic transducer 3807 at 360 degrees, so ultrasonic transducer 3807 could be aimed at any particle in whatever location within gap 3802. FIG. 38C illustrates device 3800 comprising a cage or bars 3805 located on top of gap 3802 in order to block entrance of tissue, bubbles and particles of a certain size. The size of space between the bars of cage 3805 may be determined by the typical size of blood related particles, such that only particles of the same size of blood related particles (or smaller) may enter gap 3802. Blocking entrance of large particles and tissue may be beneficial in order to achieve a cleaner signal detected by the light detector, which may be located within gap 3802.

Figure 39A:
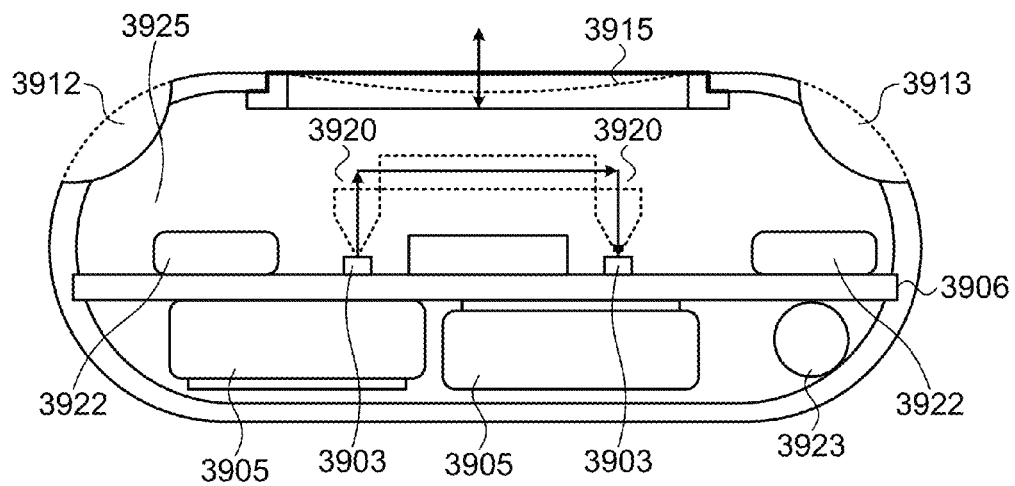
FIGS. 39A-39C are schematic illustrations of side-views cross-sections of an in-vivo device, in accordance with an embodiment of the invention.
Figure 39B:
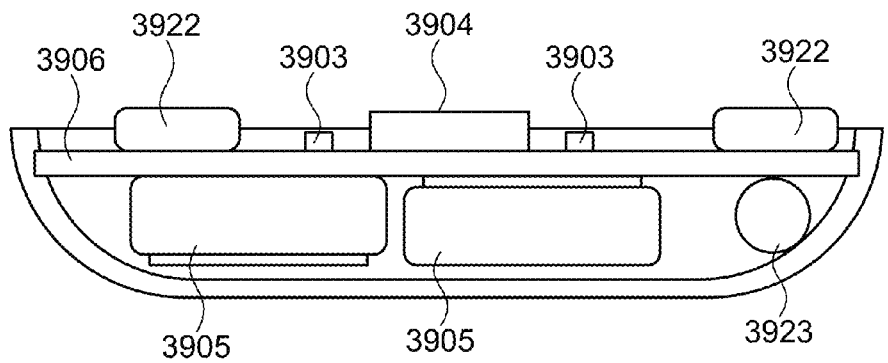
Figure 39C:
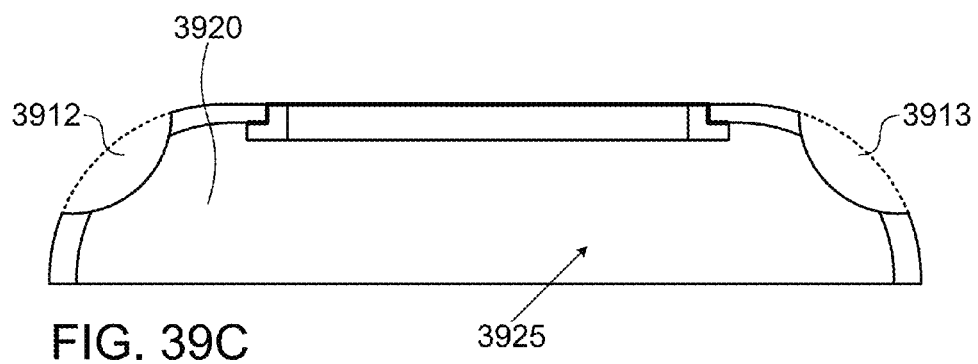

Reference is now made to FIGS. 39A-39C, which schematically illustrate side-views cross-sections of an in-vivo device, in accordance with an embodiment of the invention. FIG. 39A illustrates the entire in-vivo device 3900, while FIG. 39B and FIG. 39C illustrate the "dry" section and the "wet" section (described later in detail), respectively, of device 3900. Device 3900 may comprise housing 3901, which may have an elongated shape. Housing 3901 may comprise passage 3902, which may pass through the longitudinal axis of housing 3901. Passage 3902 may pass through the entire elongated housing 3901, from one open end 3912 till the opposite open end 3913. In-vivo fluids may flow through passage 3902, and may be examined for presence of blood or blood residues while flowing through passage 3902.

Device 3900 may comprise illumination sources 3901 for illuminating fluid passing through passage 3902 at different narrow wavelengths. Device 3900 may further comprise a light detector 3904 for detecting light signals following the light's passage through the in-vivo fluids. Illumination sources 3903 and light detector 3904 may be positioned on the same side of passage 3902 on the same PCB 3906. Thus, in order for light to pass through the fluids within passage 3902 and then reach detector 3904, housing 3901 may comprise an integrated optical element 3925. Integrated optical element 3925 may be positioned above illumination sources 3903 and detector 3904, such that optical element 3925 may be positioned between passage 3902 and illumination sources 3903 and light detector 3904. Integrated optical element 3925 may comprise two portions 3920 and 3920', each of which may be positioned above and at a close proximity to one of illumination sources 3903. Optical portion 3920 of optical element 3925 may direct light emanating from its respective illumination source 3903 through passage 3902 towards the second optical portion 3920' and then through the second optical portion 3920' towards its respective illumination source 3903. Light may also be directed the other way round, namely from the illumination source located in close proximity to the second optical portion 3920' towards optical portion 3920 and its respective illumination source 3903. This path of light from the illumination sources 3903 through integrated optical element 3925 may occur above light detector 3904, between detector 3904 and passage 3902. This may enable light emanating from either of illumination sources 3903 to reach the fluids flowing within passage 3902 as well as be detected by detector 3904, since detector 3904 may be designed to view the passage of light through the fluids between optical portion 3920 and optical portion 3920'.

In some embodiments, housing 3901 may further comprise a flexible membrane 3915. Membrane 3915 may change its shape due to applied pressure. For example, membrane 3915 may be squeezed due to pressure applied onto membrane 3915 in the occasion of a peristaltic wave passing by device 3900. Membrane 3915 may be pushed into passage 3902, which may cause fluids flowing through passage 3902 to be pushed towards either of openings 3912 or 3913. After the peristaltic wave has moved past device 3900, membrane 3915 may return to its relaxed state, and free passage 3902 from its presence, so as to allow free fluid flow into passage 3902 through either or openings 3912 or 3913. The pumping motion of membrane 3915 occurs when pressure is applied onto membrane 3915, and once pressure ceases to be applied onto membrane 3915 active fluid flow in and out of passage 3902 may be cause. Active flow of fluids through passage 3902 may be beneficial for ensuring that no particles get stuck within passage 3902, which may interfere with detection of light signals passing through the in-vivo fluids. When fluids are forced to exit and enter passage 3902, such fluids may push any particles that may have gotten stuck within passage 3902 out of passage 3902.

As illustrated in FIG. 39B, device 3900 may comprise many components in the "dry" section of device 3900. The "dry" section is the section of housing 3901 which has no contact with the in-vivo fluids flowing through passage 3902, and which may be positioned behind integrated optical element 3925. These components may be illumination source 3902, detector 3904, controller 3922, and transmitter 3921, which may transmit the detected information to an external receiver. These components may be disposed onto PCB 3906 from a first side, while other components may be disposed onto PCB 3906 from its second side. For example, antenna 3923 and batteries 3905 may also be located within the "dry" section, while being disposed onto the second side of PCB 3906. Other locations for the various components may be implemented. However, illumination sources 3903 and detector 3904 need to be on the same side of PCB 3906, while their active planes are directed towards passage 3902, so that light may be illuminated from illumination source 3903 towards passage 3902, and so that light signals may be detected by detector 3904 after passing through fluids flowing within passage 3902.

FIG. 39C illustrates the "wet" section of device 3900, which comprises components that are in contact with in-vivo fluids passing through passage 3902. For example, the "wet" section may comprise integrated optical element 3925 (which comprises portions 3920 and 3920' for directing light emanating from illumination sources 3903). The "wet" section of device 3900 may further comprise flexible membrane 3915 and openings 3912 and 3913 through which fluids may enter passage 3902 and through which fluids may exit passage 3902, after these fluids have been examined for presence of blood or blood residues.

In some embodiments, the in-vivo device may be designed to detect presence of blood within the stomach and the small bowel. Such a device may be any of devices 400, 500, 600, 700, 800, 900, 1500, 1600, 1700, 1800, 1900, 2900, 3100, 3200, 3300, 3400, 3500, 3600, 3700, and 3800 (described above in detail). In some embodiments, an imager may be located at one end of any of these devices, and the blood sensing head may be located at another end of either of these devices.

In some embodiments, the in-vivo device may be designed to detect presence of blood along the entire GI tract, from the esophagus, through the stomach and small bowel and until the end of the colon. Such a device may include a passage passing along a longitudinal axis of the device's housing, from one end to the opposite end of the housing, without any additional blocking or filtrating means located at the at least two openings of the device, in order to enable free passage for all kinds of particles through the sensing area. Such devices intended for detecting presence of blood along the entire GI tract, may be any of devices 10, 100, 200, 300, 2000, 2100, 2200, 2300, 2400, 2500, 2600, 2700, 2800, 3000, and 3900.

Figure 40:
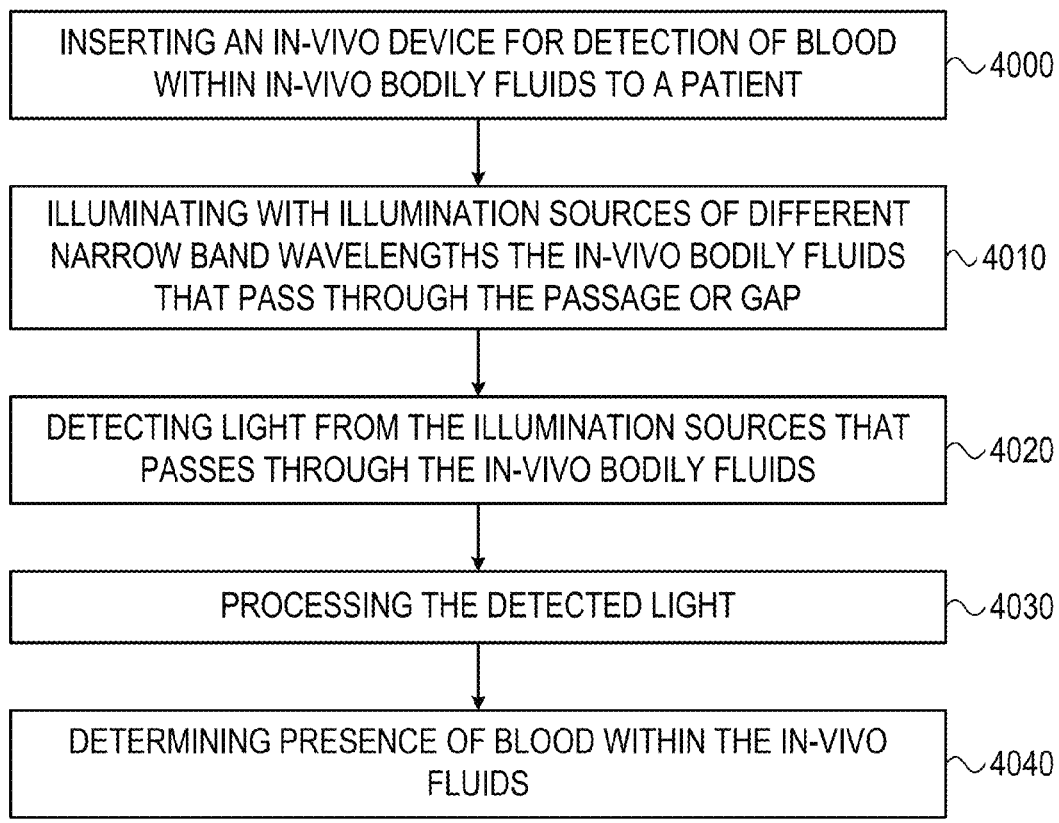
FIG. 40 is a flow chart describing a method for detection of blood within in-vivo fluids, in accordance with an embodiment of the present invention.

Reference is now made to FIG. 40, which is a flow chart describing a method for detection of blood within in-vivo bodily fluids, in accordance with an embodiment of the present invention. The method may comprise the step of inserting an in-vivo device for detection of blood within in-vivo bodily fluids to a patient (4000). The in-vivo device that may be inserted into the patient, typically to the patient's GI tract, may be any of the in-vivo devices described above, e.g., any of devices 10, 100, 200, 300, 400, 500, 600, 700, 800, 900, 1000, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, and 3900. Each of the in-vivo devices described above comprises a gap or passage through which in-vivo bodily fluids may pass. Each of the in-vivo devices described above further comprises illumination sources of different narrow band wavelengths that are located on one side of the gap or passage, and a light detector that is located on the opposite side of the gap or passage, facing the illumination sources. The method may thus further comprise the steps of illuminating with illumination sources of different narrow band wavelengths the in-vivo bodily fluids that pass through the passage or gap (4010), and detecting light from the illumination sources that passes through the in-vivo bodily fluids by the light detector (4020).

The method may further comprise the steps of processing the detected light (4030) and determining presence of blood within the in-vivo fluids (4040), which may be inferred from the processed data. According to some embodiments, the method may further comprise the step of displaying the processed light detections. The method may further comprise the step of displaying the determination of presence of blood within the in-vivo bodily fluids.

Figures 41A, 41B:
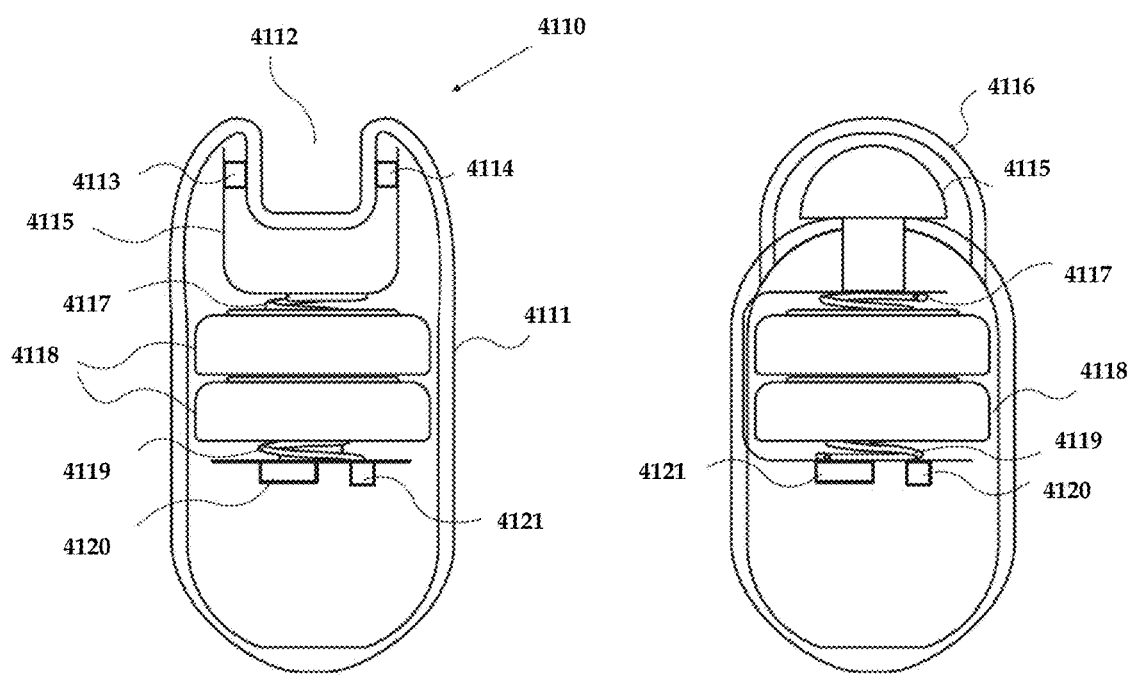
FIGS. 41A-41B are cross-sectional front view and side view of a prior-art non-imaging in-vivo diagnostic device, respectively.

As mentioned above, the in-vivo diagnostic device, according to one embodiment, is based on the in-vivo device described in WO 2010/086859 and shown in the prior-art FIGS. 41A and 41B, which demonstrate a cross-sectional front and side view of a non-imaging in-vivo diagnostic device 4110 for the in-vivo detection of bleeding, respectively. This prior-art device comprises housing 4111. One end of the housing forms gap 4112, which may be hydrodynamically curved in order to allow continuous flow of the bodily fluids through it. In some embodiments, the width of gap 4112 may be between 4-5 mm, although other widths may be used. In order for gap 4112 to allow continuous flow of the fluids through it, the in-vivo device should constantly be in contact with the body fluids in the GI tract. Therefore, in some embodiments, the device has a specific gravity of just above 1. When the specific gravity of the device is above 1, the device may pass through the colon in an optimal way. Specific gravity of just above 1 may ensure, on one hand, that the in-vivo diagnostic device does not float above the fluids, i.e., that the device and, more important, gap 4112 is in constant contact with the fluids, and, on the other hand, may ensure that the device does not sink to the bottom of the body lumen wall in the GI tract and, consequently, lose its ability to move freely.

In some embodiments, in order to avoid entry of big insoluble particles found in the GI tract into gap 4112, thereby perhaps blocking it, gap 4112 may include a membrane cover or a hydrogel cover (not shown). The membrane or hydrogel may cover the entire gap 4112, and may have holes or pores that allow only particles of a certain size or smaller to pass through them. On the other hand, the holes or pores in the membrane should not be so small so as to prevent the constant flow or passage of the liquid (due to surface tension) and blood particles through the gap. For example, the size of the holes or pores may be about 0.1-1 mm.

In a further embodiment, housing 4111 of the in-vivo diagnostic device may be made transparent or semi-transparent, and of any suitable biocompatible material, for example, Parylene®, Parylene C®, Isoplast® or Makrolon®. Other biocompatible materials may be used.

In one embodiment, there may be at least four illumination sources, e.g., LEDs 4113, located on one side of the gap 4112, irradiating at different wavelengths, while there may be at least one light detector photodiode 4114 located on the opposite side of the gap 4112.

In one embodiment, light detector photodiode 4114 is positioned such that it is directly facing LEDs 4113, while gap 4112 is located between LEDs 4113 and photodiode 4114. Light irradiated by LEDs 4113 passes through the bodily fluids and strikes photodiode 4114. Some of the light may be absorbed by the fluids, some may be scattered by insoluble particles, some may be reflected, and some may be transmitted to photodiode 4114, which may then transmit signals, created in response to the detected light, to an external receiver. According to some embodiments, LEDs 4113 may irradiate at a low frequency in order to save energy during the procedure of blood detection. Photodiode 4114 may also be activated in synchronization with LEDs 4113, e.g., the signals from the in-vivo device may be detected every 10 sec or every 1 minute. Other frequencies may be used.

The non-imaging in-vivo diagnostic device shown on FIGS. 41A-41B may comprise a printed circuit board assembly (PCB) 4115 onto which LEDs 4113 and photodiode 4114 are electronically connected. The PCB 4115 may be made of rigid portions and flexible portions. Onto PCB 4115 may further be mounted a transmitter 4120 and antenna 4121.

The photodiode 4114 may pass to the transmitter a signal created by the detected light, which had passed through the in-vivo fluids. In order to preserve energy, transmitter 4120 may be synchronized with the light detector 4114. The device may further comprise a power source 4118, such as silver-oxide batteries, and power source contacts 4117 and 4119 which are both mounted on PCB 4115. Power source 4118 should supply enough power to keep the device operating during its passage through the entire GI tract, e.g., at least for as long as 72 hours.

The power source 4118 may take the form of internal batteries, power cells, or power circuitry such as a wireless power receiving unit based on RF power transmission, which may be included in the device. The battery within the power source 4118 may be very small. An example of a suitable battery is a silver oxide battery often used to power watches, lithium batteries or any other suitable electrochemical cells having a high energy density. The model battery has voltage of 1.55 volts and a capacity of 12.5 mA-hours and has a disk-like shape with a diameter of approximately 5.7 mm and a thickness of approximately 1.65 mm. With a typical range of power requirements, the model battery can be expected to power the in vivo device for between approximately two weeks and eighteen months, depending on actual usage conditions. Other suitable power sources may be used. For example, power source 4118 may receive power or energy from an external power source (e.g., an electromagnetic field generator), which may be used to transmit power or energy to the in-vivo diagnostic device.

In further embodiments, power source 4118 may be rechargeable via induction or ultrasonic energy transmission, and may include an appropriate circuit for recovering transcutaneously received energy. For example, power source 4118 may include a secondary coil and a rectifier circuit for inductive energy transfer. In still other embodiments, power source 4118 may not include any storage element, and the in-vivo device may be fully powered via transcutaneous inductive energy transfer. As an example, such power source is commercially available from Medtronic, Inc. of Minneapolis, Minn.

The LEDs 4113 may operate in an alternating or sequential mode with different pulse duration, in order to distinguish between the different LEDs being constantly detected by the photodiode 4114. For example, one LED 4113 may irradiate the bodily fluids in the GI tract for a certain predetermined time period and then stop, and a second LED 4113 may begin irradiating the bodily fluids for another time period. When the second LED stops irradiating, the third LED may begin irradiating for yet another predetermined time period, and so on.

In some embodiments, the predetermined duration of irradiation may differ for each LED, but in other embodiments, they may all irradiate for the same duration, one subsequent to the other. The photodiode 4114 may then detect light, which passes through the bodily fluids, from one of the LEDs 4113 at a time.

One of the problems solved by the present invention is differentiating between blood and other components of the bodily fluid in the GI tract, while having a limited number of LEDs. For example, one may differentiate bile from blood by measuring the absorption above 600 nm. Thus, the intensity gradient in the absorbance area of 600-700 nm is indicative of the bile presence, whereas the intensity gradient in the absorbance area of 400-600 nm is indicative of the blood presence.

In a particular embodiment, there may be at least six LEDs, preferably white with different filters for illuminating at a specific narrow wavelength. The selection of the LEDs irradiating at different specific wavelengths is not a trivial task and constitutes an essential part of the present invention.

Figure 42:
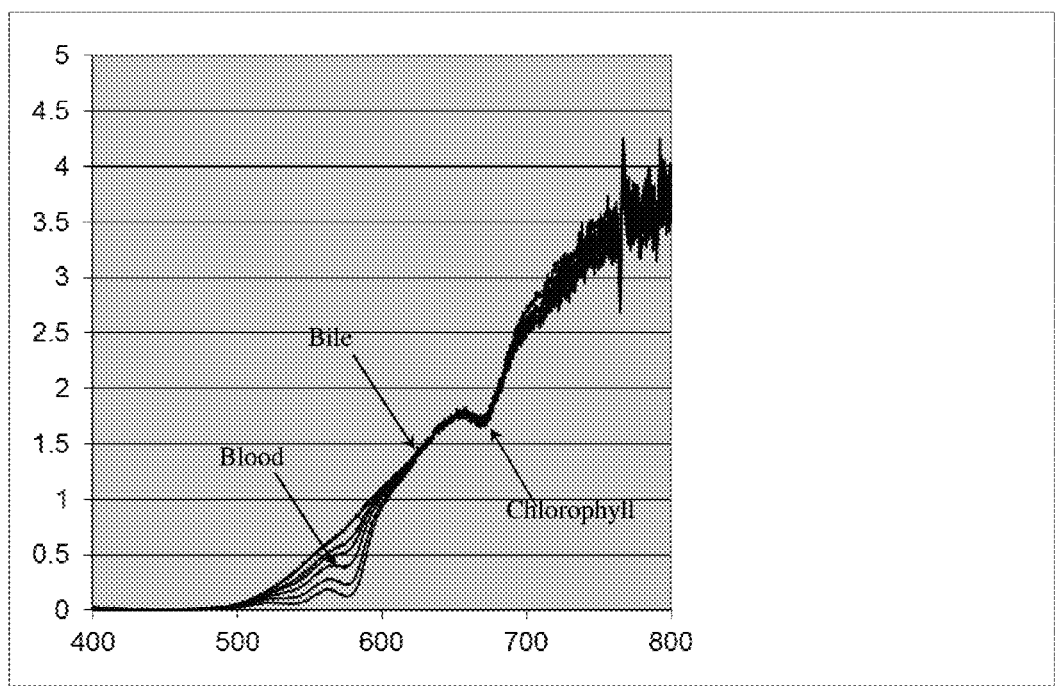
FIG. 42 is a transmittance spectrum of the three major components absorbing in the bodily fluid of the GI tract between 500 nm to 800 nm.

Reference is now made to FIG. 42, which shows absorption spectra of the three major components absorbing in the bodily fluid of the GI tract between 500 nm to 800 nm. Spectroscopic measurements of the human colon samples in the absorption range of 500-800 nm surprisingly showed some additional shoulders in the blood absorbance/transmittance spectrum, which cannot be attributed to the spectrum of blood. After evaluation of the results, two other components (in addition to blood), contributing to the overall absorbance spectrum of the bodily fluid from the GI tract, were determined to be bile and chlorophyll.

Since the absorbance spectrum of chlorophyll in water is known, it is possible to normalize the measured absorption during the in-vivo detection of blood in the GI tract, and to eliminate the contribution of chlorophyll in the transmitted absorbance data. This normalization may be done similarly to how the contribution of bile is eliminated from the transmitted absorbance data of blood, as described in WO 2010/086859.

Based on a new and unique algorithm developed by the common assignees of the present application and described elsewhere, at least six LEDs have been selected to account for the absorbance of blood, bile and chlorophyll in the bodily fluid of the GI tract. For example, chlorophyll has an absorbance peak at 670 nm, so the in-vivo diagnostic device should include the LEDs irradiating at approximately that wavelength, as well as the LEDs irradiating in range of 610-620 nm, which would help to determine the slope of the absorbance band.

Figure 43:
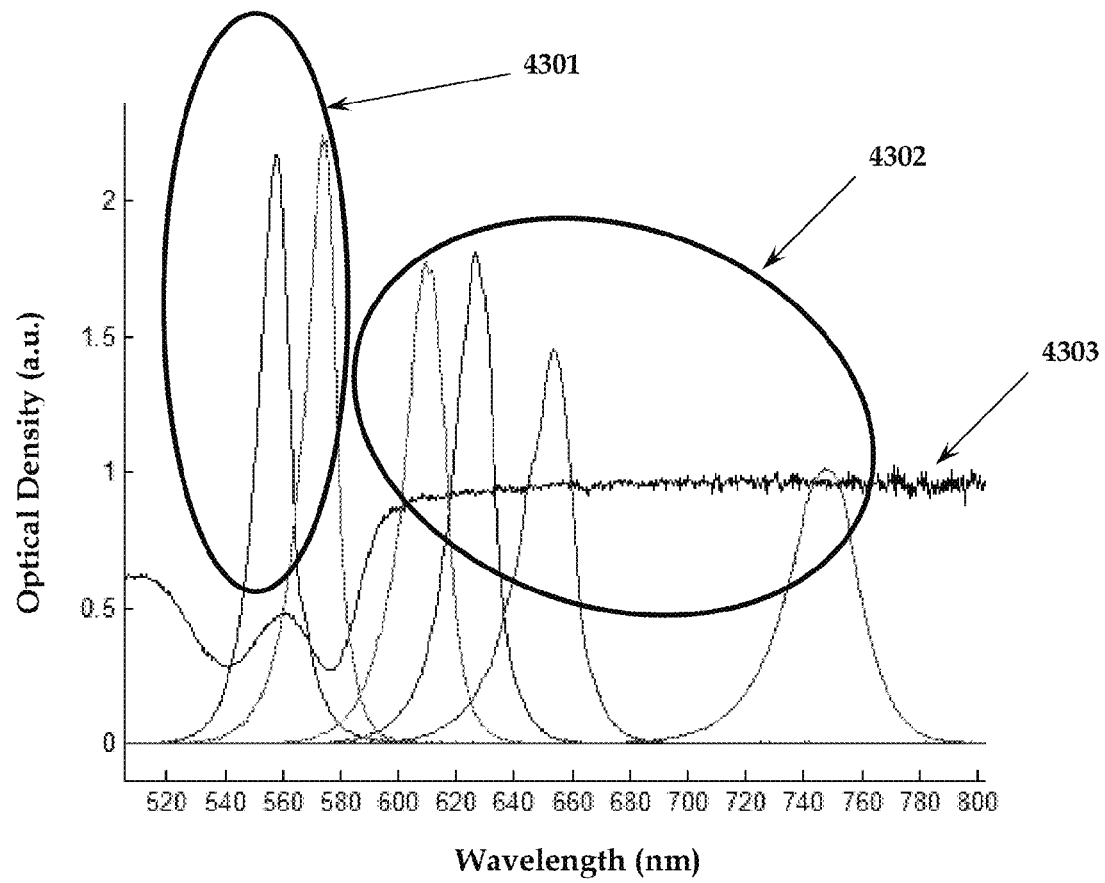
FIG. 43 is an emission spectrum of the six experimentally chosen LEDs for the in-vivo diagnostic device, in accordance with embodiments of the present invention.

Reference is now made to FIG. 43 showing the emission spectra of the six experimentally chosen LEDs, in accordance with embodiments of the present invention, though other LEDs may be chosen The configuration of LEDs was selected out of several configurations that gave similar results on the limited dataset. For example, as shown on FIG. 43, the first two LEDs emitting at 557 nm and 574 nm irradiate at the absorbance area of blood (4301). Other four LEDs emitting at 609, 626, 653 and 747 nm irradiate in the area where the absorbance of blood is insignificant but where bile and chlorophyll do absorb well (4302). Typical blood absorbance spectrum is represented by line 4303. The LEDs in the area 4302 are selected away from the blood steep slope in order to reduce sensitivity of the signal. In addition, the commercial LEDs drift and spectra overlap of about 10 nm is taken into account.

Typical LEDs 4113 have a relatively wide irradiation angle. Light from these LEDs might strike objects (e.g. tissue or the edges of the housing of device 4110) and change the reading in the photodiode 4114. In order to overcome this problem, in a particular embodiment, a blocker (not shown), which is similar to a fence surrounding the LEDs 4113 area, and slightly higher than these LEDs, is placed around them. In some embodiments, the blocker may have a dark opaque color in order to block passage of light through it.

The ranges which LEDs 4113 may be selected from may be separated into three; the first range may be between 400 nm and 600 nm, where blood absorbance is significant, the second range may be between 600 nm and 700 nm, where absorbance of bile and chlorophyll is significant whereas absorbance of blood is insignificant, and the third range may be between 700 nm and 900 nm, which is used for normalizing the absorbance of floaters floating in-vivo. At least one LED may be selected from each of the three ranges mentioned above. According to the example provided above, LEDs emitting at 557 nm and 574 nm are selected from the first range, LEDs emitting at 609, 626, and 653 nm are selected from the second range, and an LED emitting at 747 nm is selected from the third range. Other LEDs may be selected out of each of the three ranges.

In some embodiments, as described above, device 4110 may comprise six LEDs 4113. In these embodiments, the six LEDs 4113 may irradiate at approximately 560, 575, 610, 625, 650 and 750 nm. For example, approximately may mean the LEDs 4113 may irradiate at the wavelengths mentioned plus minus 5 nm, though other deviations may be used. In the example above, the six LEDs 4113 emit light at wavelengths 557, 574, 609, 626, 653 and 747 nm, all of which conform to the 5 nm deviation, though other deviations may be used.

Another LED that may be selected for use in device 4410 (FIGS. 44A-44C, described in detail below) may be an LED emitting at 660 nm, since chlorophyll b has high absorbance at 660 nm. This LED may either be used in addition to the list of six LEDs provided above, or it may replace one of the LEDs listed above, for example, LED emitting at 660 nm may replace the LED emitting at 653 nm.

The LEDs 4113 may be any commercially available LEDs, such as Hyper TOPLED® by Osram™, KPHHS-1005SECK® or KPHHS-1005CGCK by Kingbright™, ED-109UYGL, ED-107UR or ED-012UORS by Optotech, ELC-740-25 by Epigap, or TLPGE1008A by Toshiba.

The photodiode 4114 may be, for example, OPT101® by Burr-Brown Products™ from Texas Instruments, MLX75305C® by Melexis™ Microelectronic Integrated Systems, or TSL12S-E23®, TSL13T, or TSL257T by TAOS™ (Texas Advanced Optoelectronic Solutions).

Figure 44A:
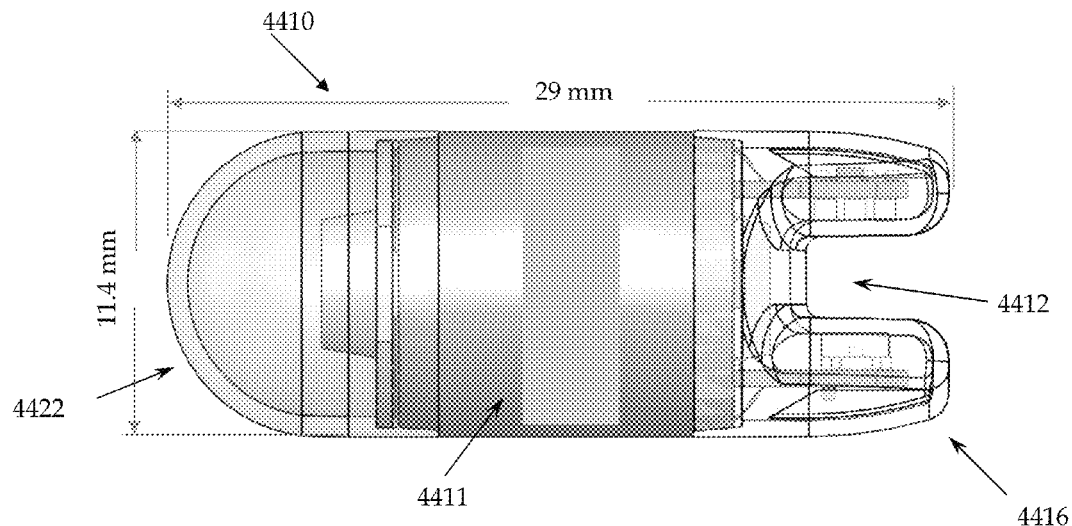
FIG. 44A is a front view of an imaging in-vivo diagnostic device, constructed and operative, in accordance with embodiments of the present invention.
Figure 44B:
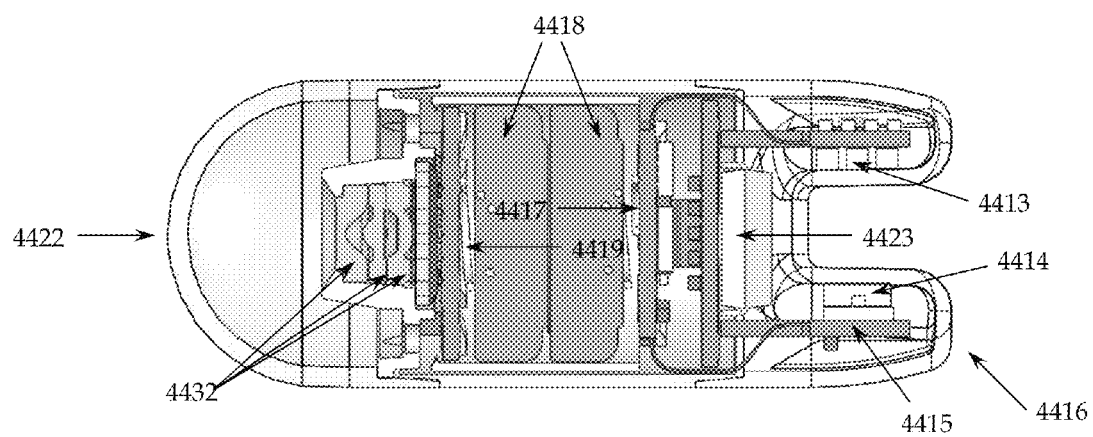
FIG. 44B is a cross-sectional front view of an imaging in-vivo diagnostic device, constructed and operative, in accordance with embodiments of the present invention.
Figure 44C:
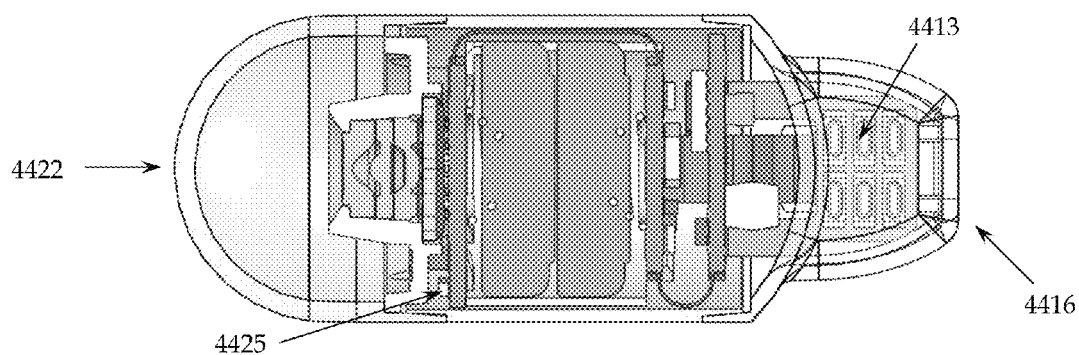
FIG. 44C is a cross-sectional side view of an imaging in-vivo diagnostic device, constructed and operative, in accordance with embodiments of the present invention.

In one embodiment, the in-vivo diagnostic device may also be an imaging device, e.g., it may contain an imager in order to acquire in-vivo images of the pathological lesions in the GI tract where the bleeding may occur. Reference is now made to FIGS. 44A, 44B and 44C, which show a front view, a cross-sectional front view and a cross-sectional side view of an imaging in-vivo diagnostic device 4410, constructed and operative, in accordance with embodiments of the present invention, respectively. This imaging in-vivo device may be based on the PillCam® capsule endoscopy system commercially available from the common assignee of the present invention.

The components of the imaging in-vivo diagnostic device 4410 may be similar to the components of the non-imaging in-vivo device, as described above. Housing 4411 may form gap 4412, which may be hydrodynamically curved in order to allow continuous flow or passage of the bodily fluids through it. In some embodiments, the width of gap 4412 may be between 4-5 mm, although other widths may be used. Illumination sources, e.g., LEDs 4413 may be placed on one side of the gap 4412, each irradiating at a different narrow band wavelength, while on the opposite side of the gap there may be at least one light detector or photodiode 4414, which may be positioned such that it is directly facing LEDs 4413. In some embodiments, the number of LEDs 4413 may be six, while in other embodiments other numbers may be used. The end of device 4410, which comprises gap 4412, LEDs 4413, and light detector or photodiode 4414 form sensing head 4416.

Reference is now made to FIGS. 45A and 45B showing printed circuit board assembly (PCB) 4415 that may have a rigid portion, onto which LEDs 4413 and photodiode 4414 are oppositely mounted, so that photodiode 4414 would directly faces LEDs 4413. In one embodiment, the shape of the rigid portion of PCB 4415, onto which LEDs 4413 and photodiode 4414 are mounted, may be any shape, as long as it complies with the shape and size of both sides of the in-vivo device, on either side of gap 4412.

Typically, the contour of the device should be round with no sharp edges, so that it is suitable for in-vivo insertion either by swallowing or through other methods, such that it would not cause any damage to tissue during insertion. Furthermore, the device should be designed with rounded edges so it does not cause any harm to tissue while passing along the GI tract by natural peristalsis. Thus, the shape of the rigid portion of PCB 4415, to which LEDs 4413 and photodiode 4414 are connected, as shown in FIGS. 45A and 45B, may be suitable. In other embodiments, other shapes such as a triangle, rectangle, and square may be used for PCB 4415, as long as the shape of housing 4411 of the in-vivo diagnostic device covering PCB 4415 is not sharp and is suitable for insertion in-vivo, since that is the part that actually comes in contact with the in-vivo tissues.

In a further embodiment, flexible portions 4424 of PCB 4415 may be folded in order to adjust the shape of the PCB to fit within the volume of the in-vivo device. For example, as shown on FIGS. 45A and 45B, flexible portions 4424 connect the five rigid portions to one central rigid portion. The flexible portions 4424 are then folded, as shown on FIG. 45C to create a U shape which fits the U shape of the device, designed such that there is room between the rigid portions in order to form gap 4412. Connected to the rigid portion may be battery contacts 4417 and 4419. In between battery contacts 4417 and 4419, batteries 4418 may be inserted, as shown in FIGS. 44B and 44C.

In another embodiment, the device may include imaging head 4422, as shown in FIGS. 44A-44C and 45C, in order to acquire in-vivo images of a body lumen. In this case, the combined mode of operation of the two heads (sensing head 4416 and imaging head 4422) may be either simultaneous, for example when the device is in the stomach or small bowel, or only sensing head 4416 may operate when the device is in the colon (thus saving energy). In other embodiments, the sensing head and the imaging head may operate simultaneously throughout the entire GI tract.

Figure 45C:
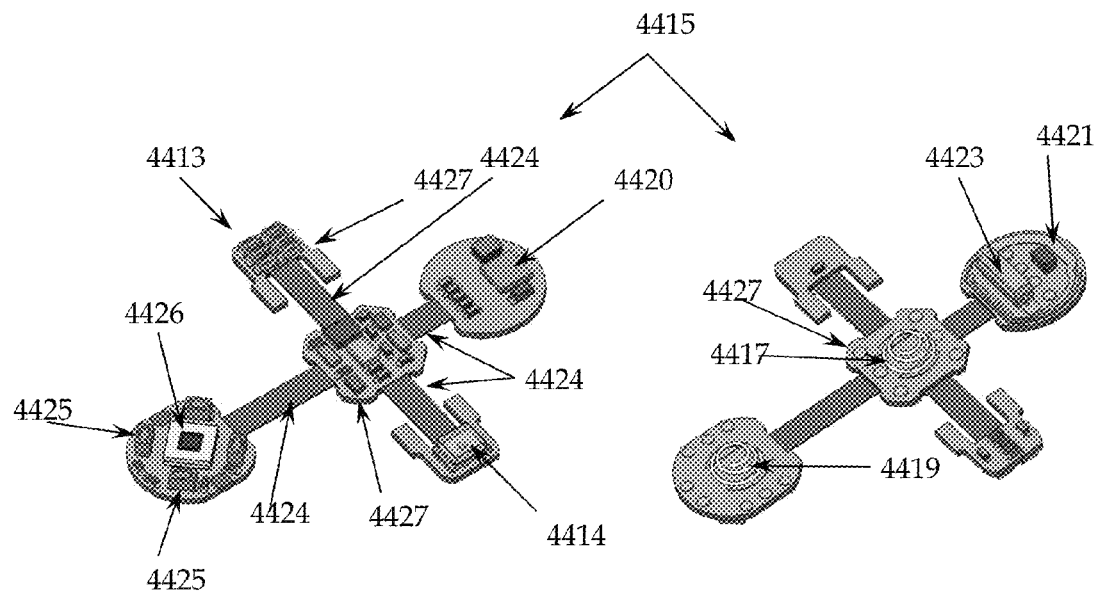
FIG. 45C is a perspective view of the folded printed circuit board assembly, in accordance with embodiments of the present invention.
Figure 45C:
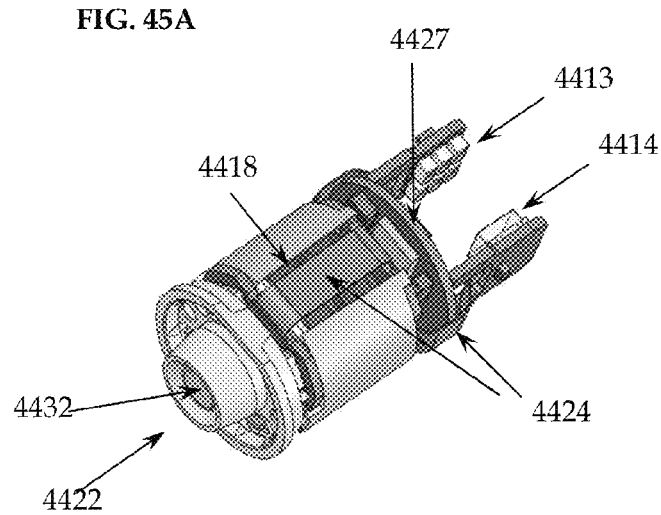

Imaging head 4422 of the device 4410, as shown in FIGS. 44B, 44C and 45C, may include one or more illumination sources 4425, such as LEDs or other suitable illumination sources, and lenses 4432 placed behind a transparent convex (e.g., dome-shaped) optical window.

In a particular embodiment, imaging head 4422 of the in-vivo device may include an in-vivo camera/imager 4426, as shown on FIG. 45A. The LEDs 4425 may, for example, illuminate a body lumen or cavity being diagnosed. An imaging optical system, may comprise, for example, one or more optical elements, such as one or more lenses 4432 or composite lens assemblies, one or more suitable optical filters, or any other suitable optical elements, and may be included in the in-vivo device and may aid in focusing reflected light onto an imager (not shown), focusing illuminated light, and/or performing other light processing operations.

In one embodiment, the device may contain reed switch 4423, which may be actuated by magnets and used as a proximity sensor. It may also be used to switch off the device when the operation is not needed, in order to extend the battery life. In a further embodiment, PCB 4415 may comprise a transmitter 4420 and antenna circuit 4421, which are shown on FIGS. 45A-45B.

Figure 46A:
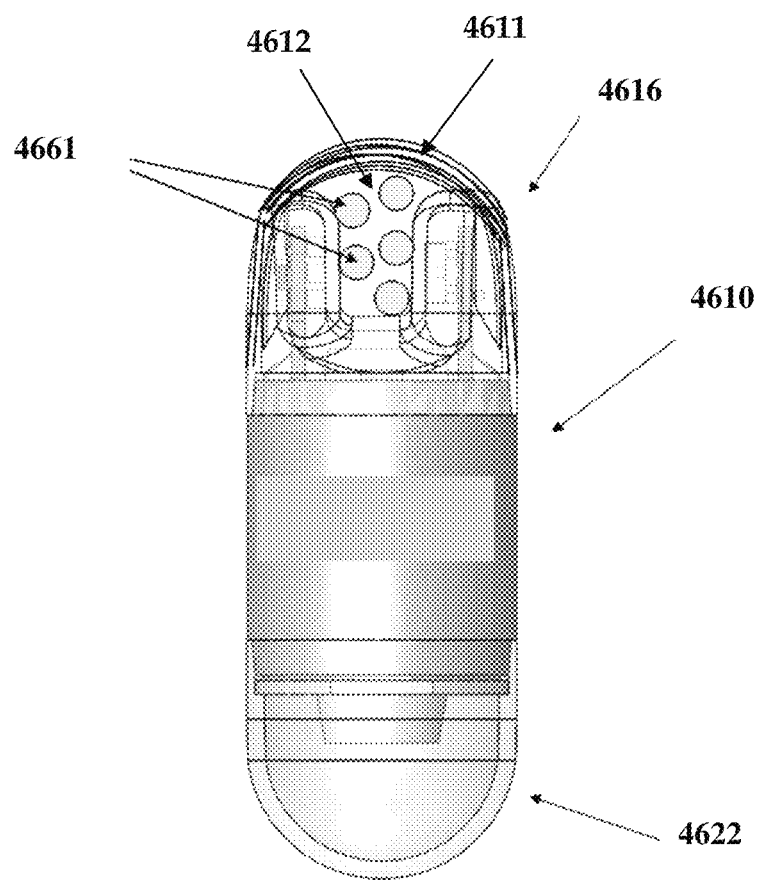
FIGS. 46A-46B are front views of different imaging in-vivo diagnostic devices, in accordance with embodiments of the present invention.
Figure 46B:
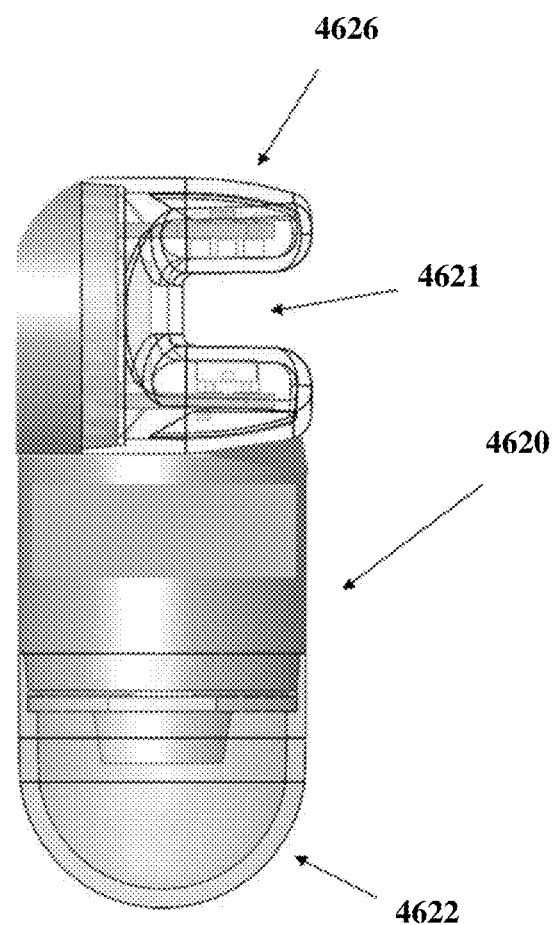

Reference is now made to FIGS. 46A-46B which illustrate front views of different imaging in-vivo diagnostic devices, in accordance with embodiments of the present invention. According to some embodiments, gap 4612, through which bodily fluids (carrying or not carrying blood related particles) pass, may be blocked by large particles flowing within the bodily fluids. In some embodiments, air bubbles flowing within the bodily fluids may be caught inside gap 4612. In yet other embodiments, the fluids within the GI tract may experience turbulences. When, for example, device 4610 passes through the small bowel, there may be turbulences in the bodily fluids that may cause device 4610 to be pushed against the tissue wall of the GI tract. The GI tract tissue may then be pushed into gap 4612 thus at least partially blocking LEDs 4613 from irradiating the bodily fluids. When gap 4612 is blocked such that constant flow of bodily fluids through it is prevented, the operation of sensing head 4616 may be interfered. In order to overcome possible blockage of gap 4612, a few in-vivo devices different than device 4610 may be used.

For example, device 4610 shown in FIG. 46A may comprise a cover 4611 that covers the entire sensing head 4616. Cover 4611 may be made of, for example, silicon, which is safe to use in-vivo as it is a biocompatible material, though other materials may be used. In some embodiments, cover 4611 may be placed over the entire sensing head 4616 following assembly of all plastic parts of device 4610, which constitute the shell of device 4610. Cover 4611 may comprise holes 4661 located on both sides of gap 4612 (which is now covered by cover 4611). Holes 4661 may be located on the sides of gap 4612 that are perpendicular to LEDs 4413 and to photodiode 4414 (as shown in FIG. 44B), and which are located in between the LEDs 4413 and photodiode 4414. In some embodiments, no holes are located on the top end of gap 4612, or the top end of cover 4611. The top end of cover 4611 (or top end of gap 4612) may be on a plane parallel to the plane of rigid portion 4427 of PCB 4415 (FIGS. 45A-45C), and farthest from it around the contour of cover 4611. However, in other embodiments, holes similar to holes 4661 may be located at the top end of cover 4611 in addition to the holes 4661 located on the sides of gap 4612 (described above). The size of each of holes 4661 may be large enough so as to allow free passage of blood particles, and yet small enough to prevent passage of large particles that might block gap 4612, thus blockage of irradiation from LEDs 4413 towards bodily fluids and/or blockage of absorbance or transmittance signals of the bodily fluids towards photodiode 4414 may be avoided. In some embodiments, cover 4611 and holes 4661 may be replaced with a net or mesh comprising holes at an appropriate size that allow free passage of blood particles but prevent passage of large particles, as described above. In some embodiments, device 4610 may comprise an imaging head 4622 located opposite the sensing head 4616, whereas in other embodiments, device 4610 need not comprise an imaging head 4622 in addition to sensing head 4616.

Another example of an imaging in-vivo diagnostic device may be device 4620, shown in FIG. 46B. In some embodiments, device 4620 may comprise an imaging head 4622 located opposite a sensing head 4626. Yet, in other embodiments, device 4620 need not comprise an imaging head 4622 in addition to sensing head 4626. In some embodiments, the sensing head 4626 may comprise a gap 4621 positioned perpendicularly to the longitudinal axis of device 4620. Unlike in device 4110, where the opening of gap 4112 is parallel to the longitudinal axis of device 4110, the opening of gap 4621 is perpendicular to the longitudinal axis of device 4620.

Figures 47A, 47B:
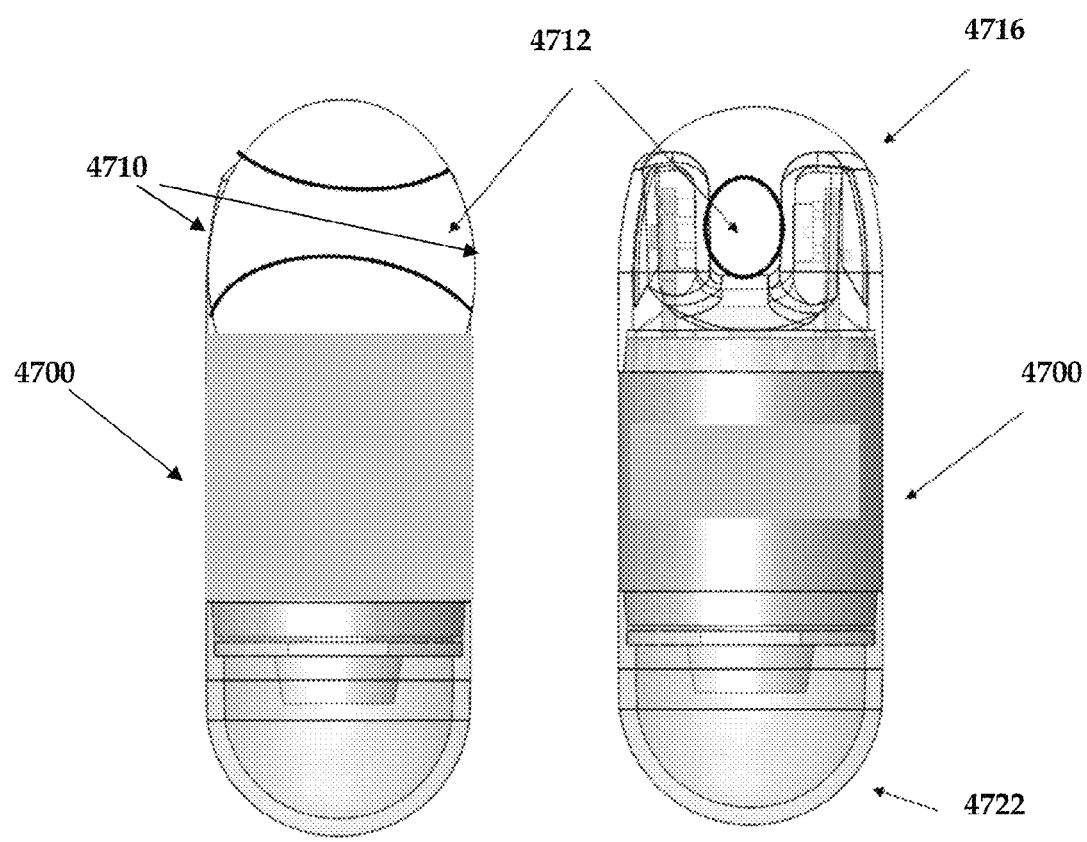
FIGS. 47A-47B are front and side views of an imaging in-vivo diagnostic device, respectively, in accordance with the present invention.

Reference is now made to FIGS. 47A-47B which illustrate front and side views, respectively, of another imaging in-vivo diagnostic device, in accordance with the present invention. In some embodiments, device 4700 may comprise an imaging head 4722 located opposite a sensing head 4716, whereas in other embodiments, device 4700 need not comprise an imaging head 4722 in addition to sensing head 4716. Device 4700, shown in FIGS. 47A-47B may comprise one tunnel 4712 that passes throughout the entire sensing head 4716. Device 4700 may comprise a tunnel 4712 instead of a gap (e.g., gap 4412 of device 4410, in FIG. 44A). In some embodiments, as shown in FIG. 47B, tunnel 4712 may comprise openings 4710 of a diameter larger than the diameter of the tunnel 4712 located between its openings 4710. Openings of a diameter larger than the diameter of the middle/inside of the tunnel 4712 may enable better flow of bodily fluids through tunnel 4712, thus avoiding blockage between the LEDs and the photodiode, e.g., LEDs 4413 and photodiode 4414 (FIG. 44B) and enabling proper operation of sensing head 4716.

Figure 48:
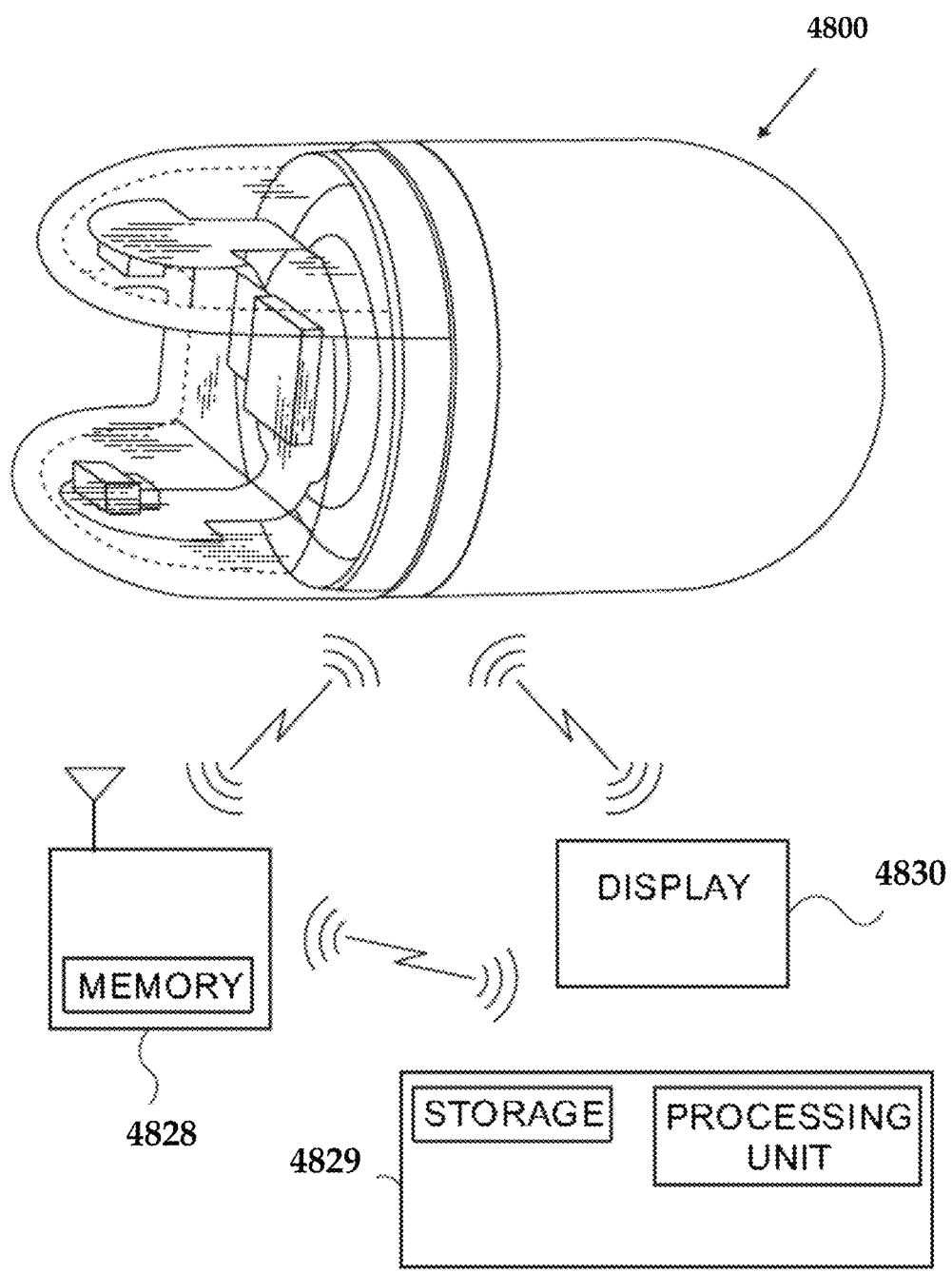
FIG. 48 is a schematic presentation of the system for the in-vivo detection of bleeding in the GI tract, in accordance with embodiments of the present invention.

Reference is now made to FIG. 48, which presents a schematic illustration of a system for obtaining absorbance data, or the like, from an in-vivo diagnostic device, e.g., device 4800, in accordance with embodiments of the present invention. The system may comprise an in-vivo diagnostic device, e.g., device 4800 (or any of devices 4410, 4610, 4620 or 4700), external receiver/recorder 4828, which is able to receive data (e.g., absorbance and/or image data) transmitted by the device 4800, computing platform (workstation) 4830, which may store, process, and analyze the received data, and optional display 4829. A transmitter, e.g., transmitter 4420 (FIG. 45A) may transmit the signals, detected by photodiode 4414, to external receiver 4828, which may be portable, non-portable, mobile, non-mobile, wearable, or the like. In a particular embodiment, the transmitter may operate using radio waves. Other known wireless methods of transmission may be used. The transmitter may include, for example, a transmitter module or sub-unit and a receiver module or sub-unit, or an integrated transceiver or transmitter-receiver.

The transmitter may also be capable of receiving signals/commands, for example from an external transceiver. For example, the transmitter may include an ultra-low power Radio Frequency (RF) high bandwidth transmitter, possibly provided in Chip Scale Package (CSP). The transmitter may include different control capabilities, for example, for controlling the various operations of the device, although control capabilities or one or more aspects of control may be included in a separate component. The transmitter is typically part of an ASIC (application specific integrated circuit), but may be of other constructions; for example, the transmitter may be a processor executing instructions. The transmitter may transmit at any frequency selected from Industrial, Scientific and Medical radio frequencies (ISM). For example, when the transmitter is to transmit data related to signals detected by the photodiode alone, it may transmit at a frequency of 433.9 Mhz, at bandwidth +/−200 Khz. And when, for example, the transmitter is to transmit image data as well as signals detected by the photodiode, it may transmit at a frequency of 434.1 Mhz, at bandwidth +/−8 Mhz.

In one embodiment, the transmitter, e.g., transmitter 4420 may transmit data to receiver 4828 via antenna 4421, shown on FIG. 45B. While or after the in-vivo diagnostic device 4410 passes through the GI tract, the signals detected by photodiode 4414 may be transmitted by a transmitter 4420 to external receiver 4828, outside the patient's body. In a particular embodiment, receiver 4828 may be a disposable receiver or a wearable disposable patch. It may possibly be close to or worn on a patient. A patient may wear the receiver and may swallow a new in-vivo diagnostic device every day for a week, for example, in order to constantly monitor the bodily fluid inside the GI tract, and consequently, detect the bleeding and determine the bleeding dynamics over time. Therefore, there may be a need to monitor the GI tract during a long period of time, e.g., a week, by inserting into a patient a new device every day during an examination period. The receiver 4828 may include a visual indication, which may show where along the GI tract the bleeding was detected.

Receiver 4828 may include a processor which may create absorbance spectra of the bodily fluids according to the signals detected from the at least four wavelengths. The processor may further compare the absorbance spectra of the in-vivo bodily fluids to a reference absorbance spectra of bile and chlorophyll and to a reference absorbance spectra of blood, which are created by detecting absorbance spectra of bile, of chlorophyll and of blood in water and of different concentrations of chlorophyll vs. blood, and bile vs. blood, and thus determine whether there is chlorophyll in-vivo, whether there is bile in-vivo, and whether there is blood or whether there is all three. Furthermore, the processor may compare between the measured absorbance spectra with the reference spectra and may determine the concentration of either bile, blood or both. When there is all bile, chlorophyll and blood present in the same sample, the processor, by comparing the measured absorbance spectra to the reference spectra, may indicate whether the ratios between the bile or the chlorophyll and blood indicate bleeding or whether the results indicate high concentration of blood but with no real bleeding, which may also indicate a pathology. In other embodiments, the concentration of blood, along with other detected in-vivo data, may indicate the location of blood in-vivo. In other embodiments, instead of comparing between transmittance or absorbance spectra, a comparison between discrete signals detected by photodiode 4414 and a predetermined threshold may be done, as described with respect to FIGS. 11-12 of WO 2010/086859, mentioned above.

In still further embodiments, receiver 4828 may comprise a memory unit for storing the data transmitted from the in vivo device over time. Receiver 4828 may include one or more antenna elements or arrays, for example, in order to improve signal reception and/or to allow localization of the in-vivo device. The in-vivo device may optionally include a processing unit separately from transmitter 4420 that may, for example, contain or process instructions. In other embodiments, instead of receiver 4828 comprising a memory unit, the device (e.g. device 4410, 4610, 4620, 4700 or 4800) may comprise a memory unit for recording and storing the detected signals/data. The device may then transmit the data to a processor for processing the data to calculate level of concentration of blood over time (as will be described below in FIG. 49) and a display system may then display it to a user.

In some embodiments, the receiver 4828 (or the device in itself) may be operatively associated with a computing platform or workstation 4830, which may, for example, store the received data (e.g., image data and/or other data), process the received data (e.g., using a processor), store the data in a storage unit, display the received data and/or processed data (e.g., using a monitor), analyze the data, perform post-processing operations, perform real-time processing operations, or the like.

In some embodiments, the in-vivo diagnostic device may communicate with an external receiving and display system 4829 (e.g., monitor) to provide display of data, for example, the absorbance spectra or a single optical density value, control, or other functions. In some embodiments, the display may be a separate unit not part of the computing device 4830. In other embodiments, display 4829 may display the absorbance spectra along with other information, such as pH values at the correlating in-vivo locations of where the pathological lesions are detected or expected. In other embodiments, where the device may for example comprise an imager and a broad band illumination, i.e., white light, in-vivo images may be displayed either alone or alongside the in-vivo locations where blood, or bile, or chlorophyll, or all them are detected. Other embodiments may have other configurations and capabilities. For example, components may be distributed over multiple sites or units, and control information or other information may be received from an external source.

According to some embodiments, the in-vivo diagnostic may comprise a pH detector (not shown). An example for a pH detector may be the pH detector by Endonetics Inc. as disclosed in U.S. Pat. No. 6,689,056. Such a pH detector may continuously detect pH levels, and transmitter 4420 may transmit the detected pH values along with the signals detected by photodiode 4414 to a receiver external to a patient's body. Since, at different locations along the GI tract there are substantially different pH levels, the detected pH may indicate the in-vivo location. For example, in the stomach there is a low acidic pH of between 1 to 4, while in the small bowel the pH values are between 7 to 8 (slightly alkaline), and in the colon the pH is between 5.5 and 7 (slightly acidic).

In other embodiments, the in-vivo location where bleeding is detected may be calculated by an algorithm, such as disclosed in U.S. Pat. No. 7,596,403 or by other algorithms. U.S. Pat. No. 7,596,403 discloses a method for determining path length through a body lumen, for example, path length or distance to a specified location. This information may be used alone or in combination with other in-vivo data, such as pH, in order to determine the in-vivo location in which light detector 14 detects light signals, which may indicate the presence of blood.

According to FIG. 42, and as mentioned above, six LEDs 4413 may irradiate at 557, 574, 609, 626, 653 and 747 nm. The ratio of absorbance of chlorophyll between intensity of detected light that is irradiated from at least two LEDs irradiating at wavelengths selected from 600 nm to 750 nm is typically very high, which is similar to how the absorbance spectrum of bile behaves. Therefore, in order to determine whether chlorophyll is present in-vivo at a specific location, there is a need for a calculation of a ratio between intensity of detected light that is irradiated from at least two LEDs irradiating at wavelengths selected from 600 nm to 750 nm, but which would give a result unique to the absorbance spectrum of chlorophyll and not to that of bile. For example, the ratio of absorbance between intensity of detected light resulting from one LED irradiating at a wavelength of 626 nm and a second LED irradiating light at a wavelength of 747 nm is calculated in that location. This ratio between intensity of detected light resulting from LEDs irradiating at wavelengths of 626 nm and 747 nm is then compared to a reference value, which may be calculated from the absorbance spectrum of chlorophyll in water, and may indicate the presence of chlorophyll. The ratio between intensity of detected light at 626 nm and at 747 nm in chlorophyll is typically larger than that ratio in bile; therefore this ratio is suitable to indicate the difference between the two. If the ratio calculated from in-vivo signals exceeds a certain threshold calculated by the processor from the reference spectra, it may be an indication to the presence of chlorophyll in-vivo in that specific location where the ratio between 626 nm and 747 nm was calculated.

In order to determine the presence of blood in-vivo, an additional ratio should be calculated and compared to a reference. The ratio of absorbance between intensity of detected light that is irradiated from at least two LEDs irradiating at wavelengths selected from 400 nm to 600 nm may be calculated. The ratio is then compared to a reference value which may be calculated from the absorbance spectrum of blood in water. If the ratio calculated from the detected signals exceeds a certain threshold calculated based on the reference absorbance spectra of blood, this may indicate the presence of blood, which may indicate a pathology in-vivo.

In some embodiments, in order to determine the presence of blood in-vivo and/or the presence of bile, LEDs 4413 may typically irradiate in at least three different narrow band wavelengths, among them, at least a first LED irradiating at a wavelength selected between 400 nm to 600 nm, at least a second LED irradiating at a wavelength selected between 600 nm to 700 nm, and at least a third LED irradiating at a wavelength selected between 700 nm to 900 nm. For example, LEDs 4413 may comprise LEDs that irradiate at 576 nm, 700 nm and 850 nm. In other embodiments, other numbers of LEDs may be used. For example, LEDs 4413 may comprise six LEDs illuminating at wavelengths of: 557, 574, 609, 626, 653 and 747 nm. Typically, a certain wavelength would be used in calculations of all of the ratios. This wavelength should be one that experiences good absorbance in blood, e.g., 747 nm.

Figure 49:
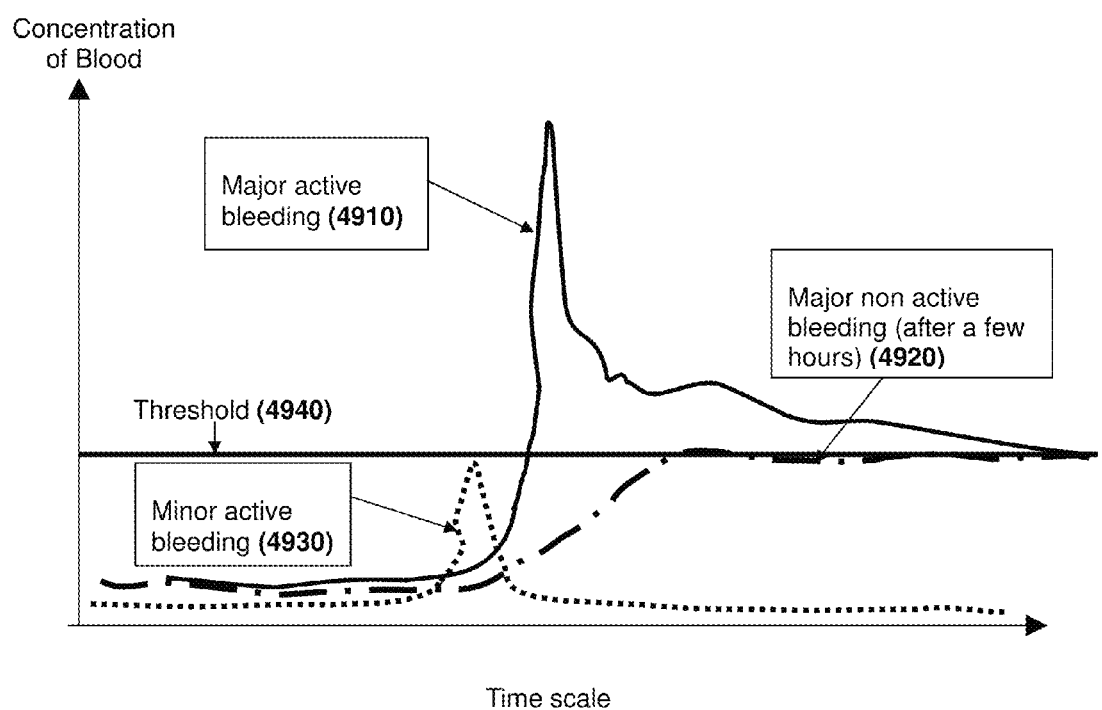
FIG. 49 is a graph describing different bleeding profiles in accordance with embodiments of the present invention.

Reference is now made to FIG. 49, which is a graph describing different bleeding profiles over time, in accordance with embodiments of the present invention. A bleeding profile over time may be presented as a time line of a bleeding event, as shown in FIG. 49. In some embodiments, display of a bleeding profile over time may be a display of blood concentration (e.g., liter of blood per liter of in-vivo bodily fluids) as a function of time. Display of a bleeding event or a bleeding profile over time, which is based on analyzed data acquired by a sensing head, e.g., sensing head 4416, may be a more efficient tool for determining presence of blood in-vivo (as well as determining the type of bleeding profile) compared to detection of redness levels in image data. A red area in an image does not necessarily indicate presence of bleeding but may, for example, appear due to a high concentration of blood vessels within the tissue. Whereas, analyzing data related to light absorbance of particles or fluids flowing within in-vivo bodily fluids and thus determining concentration of blood (over time) may provide a more accurate indication on presence of bleeding in-vivo, substantially eliminating errors that may occur due to the tissue background.

According to some embodiments, there may be a few different bleeding events or bleeding profiles in-vivo, which may correlate to different in-vivo pathologies. One of those bleeding events or profiles may be of "No Bleeding" (not shown in FIG. 49). Healthy patients should normally experience no bleeding along the GI tract. Therefore, in healthy patients the in-vivo diagnostic device 4410 may detect no bleeding, e.g., the absorbance or transmittance signals detected by device 4410 may not exceed a predetermined threshold, which is calculated based on the reference absorbance spectra of blood.

In some embodiments, the in-vivo diagnostic device may comprise an imaging head 4422 in addition to the sensing head 4416 that comprises gap 4412 (FIG. 44A). In such devices it may be possible to shorten viewing times by initially viewing the analyzed data acquired by the sensing head 4416, e.g., viewing the bleeding profile first and only then, if necessary, continue to view the image data acquired by the imaging head 4422. In an alternative embodiment, the analyzed data acquired by the sensing head 4416 may be displayed alongside the display of images captured by imaging head 4422. The viewer of the image stream may use the analyzed data acquired by the sensing head 4416 to identify portions of the image stream where a lesion or blood may be seen.

Another bleeding profile may be of "Major Active Bleeding" (4910). For example, if the in-vivo diagnostic device passes along the small bowel just about the same time when there is major bleeding, a very high peak in blood concentration may be detected. After that peak, the farther the capsule is from that bleeding area, the lower the concentration of blood detected by device 4410. In some embodiments, when a patient suffers from major bleeding, the computing device 4830 or display system 4829 may alert the physician and/or display the data related to the bleeding in a way the physician may not ignore, so as to ensure a quick assessment of the patient's condition by the physician. In some embodiments, when the in-vivo diagnostic device 4410 comprises an imaging head 4422, in addition to the sensing head 4416 (FIG. 44A), the analyzed data acquired by the sensing head 4416 may be displayed alongside the display of a stream of images captured by imaging head 4422.

A further bleeding profile or event may be of "Major Non-Active Bleeding" (4920). In some patients, an ulcer, for example, may not bleed continuously. Instead, the ulcer may bleed for a first period of time after which it may cease bleeding for a second period of time, and then begin bleeding again, and so on. In some embodiments, if the in-vivo diagnostic device 4410 reaches such an ulcer during its non-bleeding period, e.g., a few hours after a bleeding period, the peak of blood concentration may not be a high peak but rather a low and yet steady peak. The peak may be steady due to relatively long periods of bleeding, thus blood may be present along a large segment of the GI tract for a long time period, before it is less noticeable. For a physician to locate the area of the bleeding ulcer along the GI tract, he should refer to an area along the bleeding profile that is prior the steady peak. In some embodiments, the in-vivo device 4410 may comprise an imaging head 4422 in addition to the sensing head 4416 (e.g., FIG. 44A). The analyzed data acquired by the sensing head 4416 may then be displayed alongside the display of a stream of images captured by imaging head 4422. Images that correspond to the area along the bleeding profile prior to the steady peak may be viewed in order to determine the in-vivo location of the bleeding ulcer.

Another bleeding profile or event may be of "Minor Active Bleeding" (4930). Some patients may suffer from minor bleeding in the GI tract caused either by small ulcers or other in-vivo pathologies that are typically not harmful. Such minor or insignificant pathologies may appear as a distinct peak in blood concentration; however, since this is not a major bleeding, the peak may be a low peak.

In some embodiments, in order to determine what is considered a high peak in blood concentration (thus indicating major bleeding), and what is considered a low peak in blood concentration (thus indicating minor bleeding), there should be a threshold value (4940) to which any bleeding profile may be compared. As an example, a blood concentration of $10^{-3}$ [liter of blood/liter of fluids] is considered to indicate a pathology. The calculated blood concentration over time may be compared with a predetermined threshold (4940), e.g., $10^{-3}$ [liter of blood/liter of fluids] in order to determine whether the bleeding profile comprises blood concentration of above, equal to, or below $10^{-3}$ [liter of blood/liter of fluids], i.e., whether the bleeding profile indicates major bleeding, major non-active bleeding or minor bleeding, respectively. Other thresholds may be used.

According to some embodiments, in order to display blood concentration over time, the detected light signals should be analyzed and converted into blood concentration values. This conversion of light intensity to concentration may be done as described with respect to FIGS. 11-12 in WO 2010/086859, mentioned above. In particular, the predetermined threshold (4940) may be calculated, for example, from in-vitro experiments during which light intensity at different wavelengths is detected for bile in water of various concentrations, (and, in some embodiments, light intensity at different wavelengths is detected for chlorophyll in water of various concentrations), and light intensity at different wavelengths is detected for blood in water of various concentrations. As can be seen from FIG. 11 of WO 2010/086859, when the illuminated fluid contains bile and blood (spectra 111), the presence of bile causes the blood in water spectra (110BD) to be of a lower slope, i.e. the substantially high specificity of absorption by blood (110BD) of light at wavelengths between 400-600 nm is not as high when in the presence of bile. Therefore, the predetermined threshold 113, or in this invention threshold (840), is an increasing threshold; the higher the bile concentration, the higher the threshold is. Other methods may be used in order to convert the detected light signals to concentration of blood.

According to some embodiments, the display of bleeding profiles to the physician may be similar to the graph in FIG. 49, e.g., it may include the threshold value (4940) and values of blood concentration as detected by the in-vivo device, e.g., device 4410, over time. In some embodiments, the display may comprise a graph of blood concentration over time, without the threshold value (4940). In other embodiments, the bleeding profile may be presented alongside corresponding in-vivo images. In yet other embodiments, the bleeding profile graph may be interactive such that a click on the time scale (or on any location along the graph of the bleeding profile) may refer the physician to a corresponding in-vivo image. Other methods of display may be used.

According to some embodiments, in order to enable display of data related to bleeding profile over time, the in-vivo diagnostic device, e.g., device 4410 or the external receiver 4828 should comprise a memory unit. The data collected over time by the sensing head (and in some embodiments, the imaging data) may be stored in the memory unit located in external receiver 4828 or in the in-vivo device, e.g., device 4410. The stored data may then be processed and analyzed by, for example, computing platform 4830, which may be operatively associated with the receiver 4828 or the device 4410. The processed data may then be presented/displayed to the physician so the physician can make a quick and precise diagnosis of the patient's condition.

In some embodiments, the external receiver 4828 may comprise a memory unit, a processing unit and a display, such that there is no need to transfer the collected data to an additional computing platform 4830. In these embodiments the entire system may comprise the in-vivo diagnostic device 4410 and the external receiver 4828 alone, which may make it easier on a patient to undergo the majority if not the entirety of the procedure of blood detection in a home setting instead of a hospital setting.

Figure 50A:
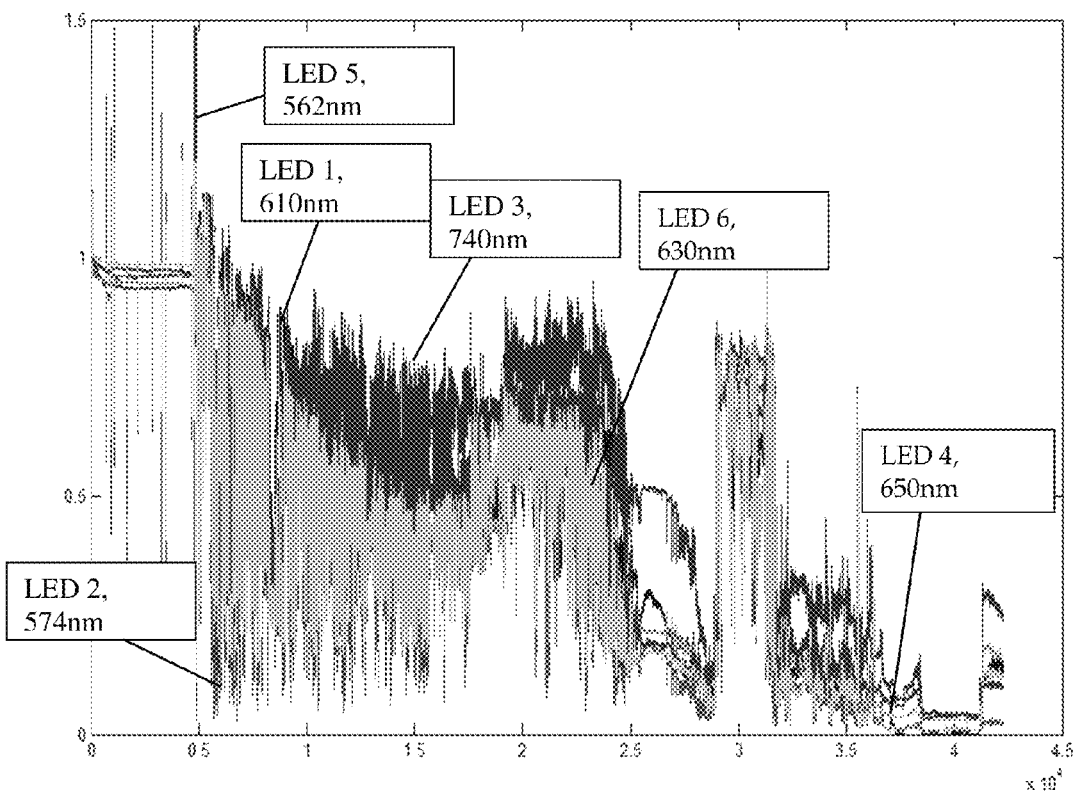
FIGS. 50A-50B are graphs showing detected light signals as a function of time before and after processing, respectively.
Figure 50B:
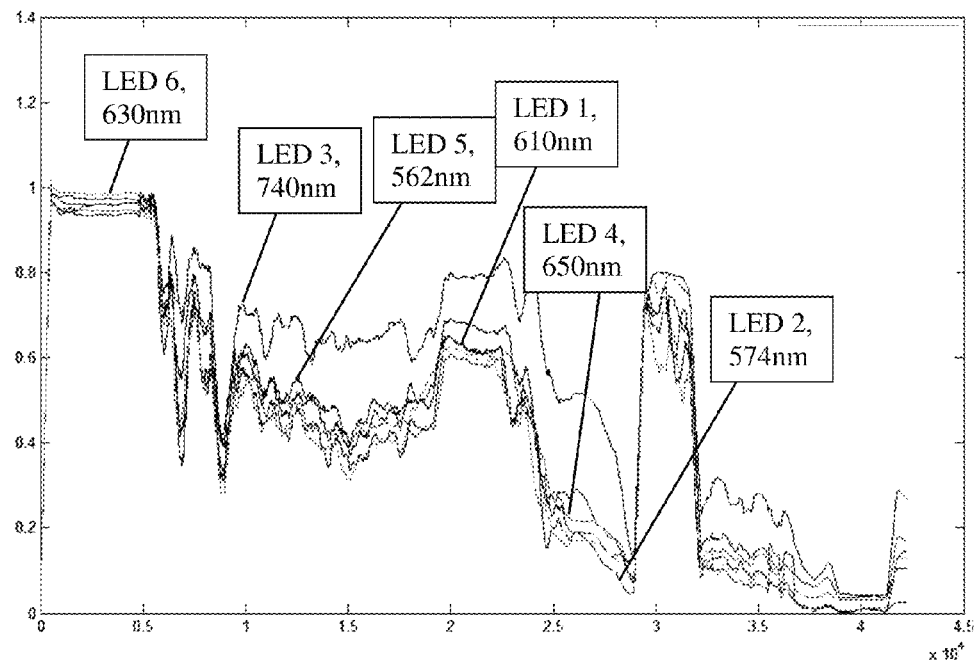

Reference is now made to FIGS. 50A-50B, which are graphs showing detected light signals as a function of time before and after processing, respectively. According to some embodiments, processing of the acquired data over time and display of the processed data over time may be important for a few reasons. The detection of light signals by a sensing head, e.g., sensing head 4416 (FIG. 44A), may be affected by noises, as shown in FIG. 50A. Noises in the detected signals may occur due to debris, floaters or air bubbles present in the in-vivo bodily fluids that pass through gap 4412, or due to tissue getting stuck within gap 4412. For example, since in the small bowel the tissue wall may be tightly pressed against the diagnostic device (e.g., device 4410), specifically during contractions occurring as part of peristaltic movement of the GI tract, the tissue wall may be pushed into gap 4412. Other noises may appear due to high turbulences or increased flow of fluids during contractions, thus causing the fluid to be cloudier, all of which may affect the illumination conditions of LEDs 4413, thereby affecting the readings of photodiode 4414. Therefore, when the system comprises a memory unit (either as part of the diagnostic device or as part of the receiver) and detected data is saved as a function of time, various filters may be applied onto the data in order to clean, smooth and substantially decrease the noises, as shown in FIG. 50B. For example, various averaging filters may be used to clean noises, e.g., a moving average filter as implemented on the signals shown in FIG. 50A resulting with clean signals shown in FIG. 50B. In other embodiments, other filters and processing methods may be used.

Following processing of the acquired light signals over time in order to substantially reduce noise and display of the "clean" data, one may identify passage of the diagnostic device (e.g., device 4410) from one area in the GI tract to another. For example, since the stomach comprises a different composition of fluids than the composition of fluids present in the small bowel, the detected intensity of light may be different in the stomach compared to the detected intensity of light in the small bowel. Equivalently, since the composition of fluids in the small bowel is different than the composition of fluids present in the colon, there should be a clear difference between detected light intensities of the two GI areas, namely the small bowel and the colon. In some embodiments, since without a special cleaning or preparation method the colon is typically filled with fluids that are cloudier than the fluids flowing in the small bowel, the intensity of transmission spectra in the colon is lower than in the small bowel (i.e., absorption of light in the colon is higher than in the small bowel).

By displaying the data over time, it may be easier to determine a change in intensity of transmission (or absorption) which may indicate a change in location of the diagnostic device along the GI tract, e.g., passage of the in-vivo diagnostic device from one area in the GI tract to another. In some embodiments, determining a change in GI tract area (based on change in intensity of transmission spectra) may be done by a physician observing the displayed data. Yet, according to other embodiments, determining a change in location of the in-vivo diagnostic device (e.g., device 4410) along the GI tract may be done automatically by a processor, using various algorithms applied onto the "clean" data over time.

When the detected data is further processed such that intensity of detected light is converted to blood concentration (and not only "cleaned" from noises), display of blood concentration as a function of time may indicate the type of bleeding profile, thereby indicating patient condition, as described above (FIG. 49).

Figure 51:
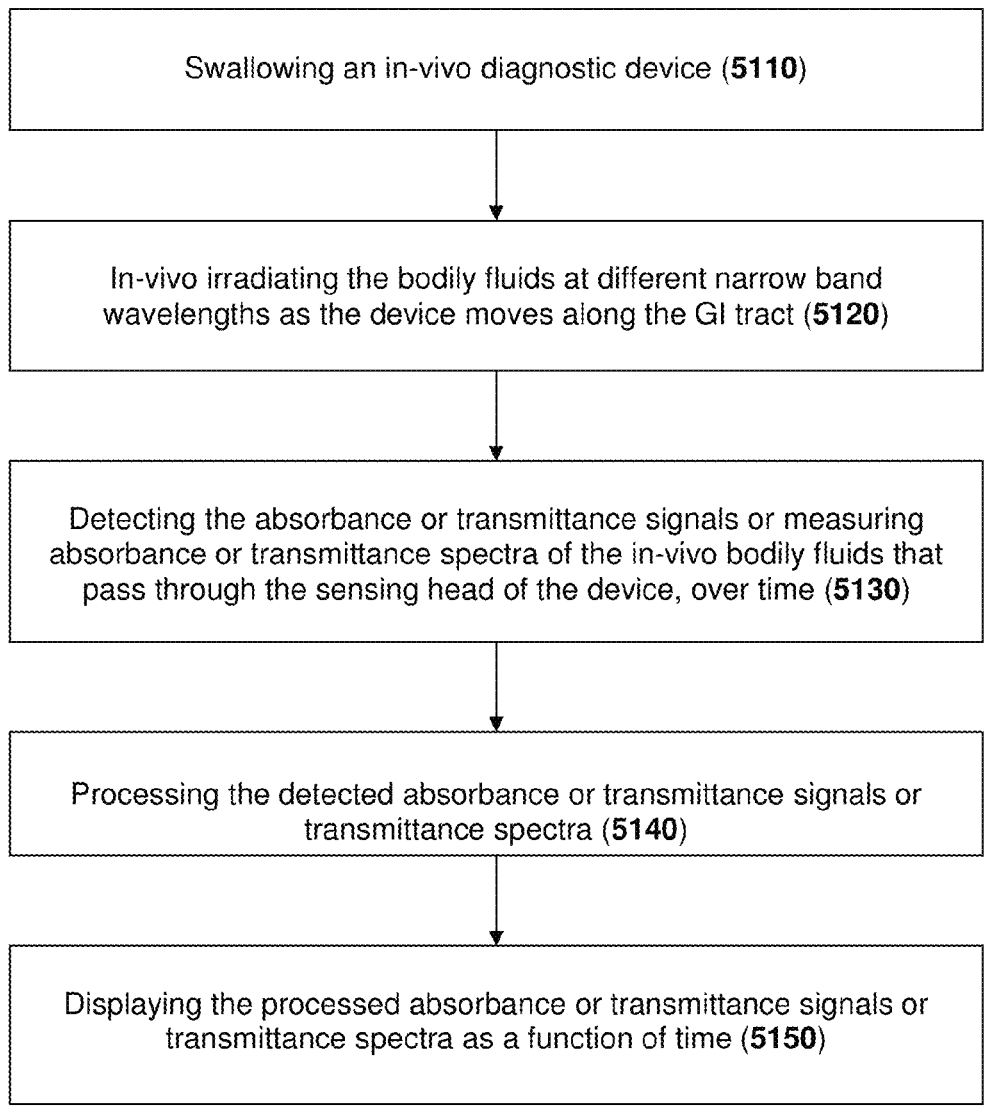
FIG. 51 is a flow chart describing a method of using an in-vivo diagnostic device in accordance with embodiments of the present invention.

Reference is now made to FIG. 51 which shows a flow chart describing a method of using an in-vivo diagnostic device for detection of bleeding in the GI tract, in accordance with embodiments of the present invention. In a particular embodiment of the invention, the in-vivo diagnostic method may include the following steps:

swallowing an in-vivo diagnostic device of the present invention (5110);

in-vivo repeatedly irradiating the bodily fluids at different narrow band wavelengths as the device moves along the GI tract (5120);

detecting the absorbance or transmittance signals or measuring absorbance or transmittance spectra of the in-vivo bodily fluids that pass through the sensing head of the device, over time (5130);

processing the detected absorbance or transmittance signals or transmittance spectra (5140); and displaying the processed absorbance or transmittance signals or transmittance spectra as a function of time (5150).

In some embodiments, the processing step may comprise converting the values representing the light detected over time by the light detector to a series of blood concentration values measured consecutively, comparing the blood concentration values to a predetermined threshold value, and identifying a bleeding profile based on the comparison.

The method may additionally comprise comparing the processed absorbance or transmittance signals or transmittance spectra with a predetermined threshold prior to displaying the processed data. In some embodiments, the method may further comprise comparing the absorbance or transmittance spectra of the in-vivo bodily fluids to a predetermined absorbance or transmittance spectra of bile and chlorophyll and determining the presence and concentration of bile and chlorophyll in the bodily fluids. In some embodiments, the method may further comprise the step of determining concentration of blood in the bodily fluids over time, following the step of processing the detected absorbance or transmittance signals or spectra over time. In yet further embodiments, the method may comprise the step of acquiring additional data other than absorbance or transmittance signals or transmittance spectra, transmitting the acquired additional data, and analyzing the additional data. The additional data that may be acquired by an in-vivo diagnostic device, such as device 4410, may be in-vivo images, pH or any other in-vivo related data.

In some embodiments, the step of displaying the processed absorbance or transmittance signals or transmittance spectra as a function of time (5150) may comprise displaying the concentration of blood as a function of time. In some embodiments, the step of displaying (5150) may comprise displaying concentration of blood, alongside displaying a video of in-vivo images stream. The in-vivo images that may be displayed alongside the blood concentration data are images that are acquired at substantially the same time as the detection of absorbance or transmittance signals or measurement of absorbance or transmittance spectra of the in-vivo bodily fluids.

In other embodiments, the step of processing the detected absorbance or transmittance signals or transmittance spectra (5140) may comprise filtering of the detected signals or spectra in order to "clean" the signals or spectra by reducing noises. In such embodiments, the step of displaying the processed absorbance or transmittance signals or transmittance spectra as a function of time (5150) may comprise displaying the "cleaned" absorbance or transmittance signals or transmittance spectra over time. Following the step of displaying (5150), the method may further comprise the step of determining passage of the in-vivo diagnostic device from one area in the GI tract to another. Determining passage from one area to another along the GI tract may be done either by a physician or by a processor that may be part of receiver 4828, computing platform 4830, or even of the diagnostic device, e.g., device 4410.

In some embodiments, the method may comprise the step of transmitting the detected absorbance or transmittance signals or transmittance spectra of the in-vivo bodily fluids, or a plurality of values representing the light detected over time by the light detector with a transmitter, e.g., transmitter 4420 to an external receiver, e.g., receiver 4828 or to a computing platform, e.g., computing platform 4830, prior to the step of processing the detected signals or spectra (5140). In other embodiments, the method need not comprise the step of transmitting the detected signals as the diagnostic device (e.g., device 4410) may perform the processing step by itself. In such case, the method may comprise the step of transmitting the processed signals to a display system prior to the step of displaying the processed signals or spectra (5150).

Figure 52:
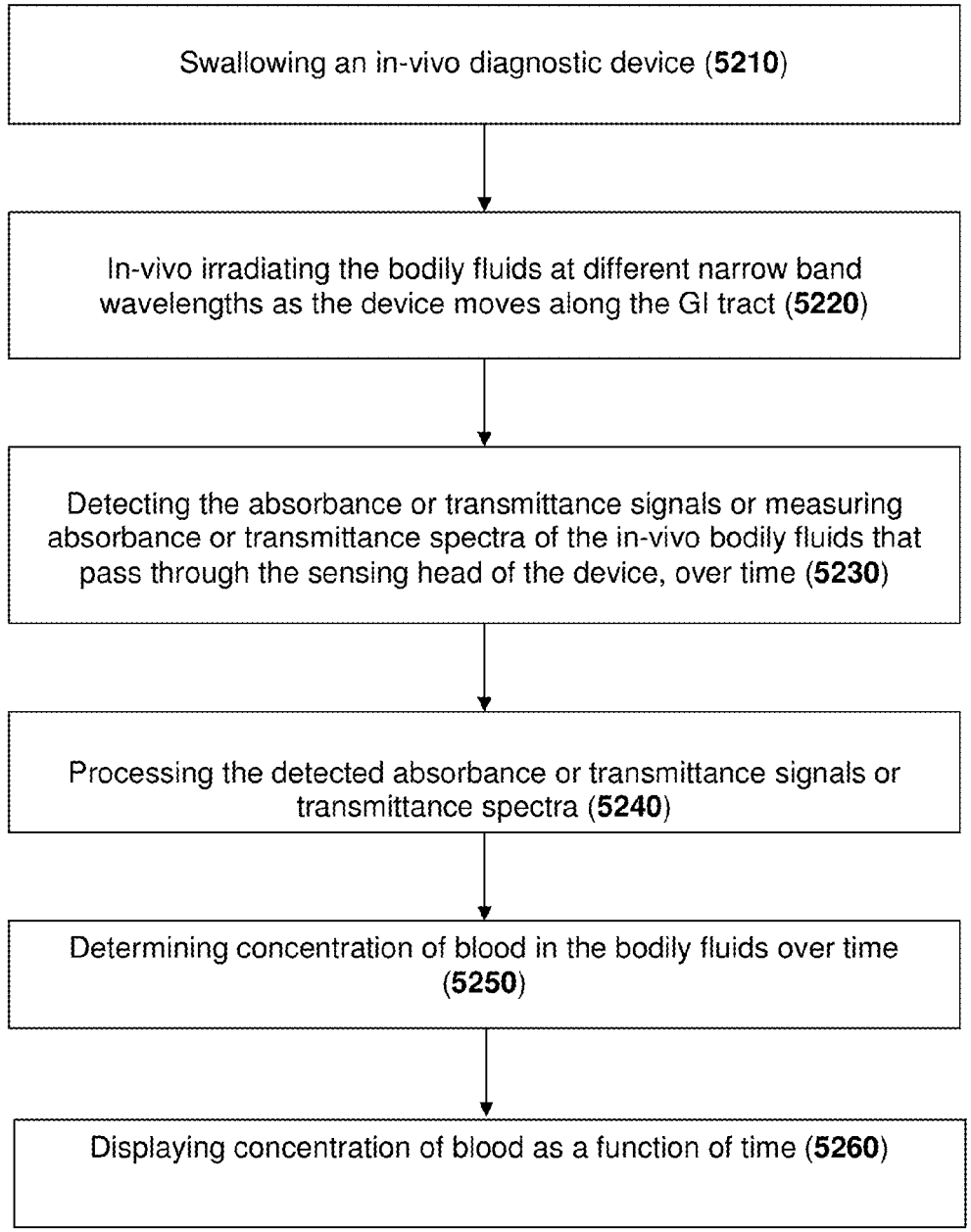
FIG. 52 is a flow chart describing a method of using an in-vivo diagnostic device for detection of bleeding in the GI tract, in accordance with other embodiments of the present invention.

Reference is now made to FIG. 52, which shows a flow chart describing a method of using an in-vivo diagnostic device for detection of bleeding in the GI tract, in accordance with other embodiments of the present invention. In a particular embodiment of the invention, the in-vivo diagnostic method may include the following steps:

- swallowing an in-vivo diagnostic device of the present invention (5210);
- in-vivo irradiating the bodily fluids at different narrow band wavelengths as the device moves along the GI tract (5220);
- detecting the absorbance or transmittance signals or measuring absorbance or transmittance spectra of the in-vivo bodily fluids that pass through the sensing head of the device, over time (5230);
- processing the detected absorbance or transmittance signals or transmittance spectra (5240);
- determining blood concentration in the bodily fluids over time (5250); and
- displaying blood concentration as a function of time (5260).

In some embodiments, the step of determining blood concentration (5250) may comprise comparing the processed absorbance or transmittance signals or transmittance spectra with a predetermined threshold. In some embodiments, the method may further comprise comparing the absorbance or transmittance signals or transmittance spectra of the in-vivo bodily fluids to a predetermined absorbance or transmittance spectra of bile and chlorophyll and determining the presence and concentration of bile and chlorophyll in the bodily fluids, prior to the step of displaying (5260).

In some embodiments, the method may comprise the step of transmitting the detected absorbance or transmittance signals or transmittance spectra of the in-vivo bodily fluids with a transmitter, e.g., transmitter 4420 to an external receiver, e.g., receiver 4828 or to a computing platform, e.g., computing platform 4830, prior to the step of processing the detected signals or spectra (5240). In other embodiments, the method need not comprise the step of transmitting the detected signals as the diagnostic device (e.g., device 4410) may perform the processing step by itself. In such case, the method may comprise the step of transmitting the processed signals to a display system prior to the step of displaying blood concentration over time (5260).

In some embodiments, the step of displaying blood concentration as a function of time (5260) may comprise displaying concentration of blood, alongside displaying a video of in-vivo images stream. The in-vivo images that may be displayed alongside the blood concentration data are images that are acquired at substantially the same time as the detection of absorbance or transmittance signals or measurement of absorbance or transmittance spectra of the in-vivo bodily fluids.

In some embodiments, the method may comprise the step of acquiring additional data other than absorbance or transmittance signals or transmittance spectra, transmitting the acquired additional data, and analyzing the additional data. The additional data that may be acquired by an in-vivo diagnostic device, such as device 4410, may be in-vivo images, pH or any other in-vivo related data.

According to some embodiments, in order to ensure that an in-vivo diagnostic device, e.g., device 4410, provides reliable results, device 4410 may comprise two LEDs 4413 of the same wavelength for each of the three ranges from which LEDs 4413 may be selected. As described above, LEDs 4413 may be selected from three ranges: 400-600 nm, 600-700 nm and 700-900 nm. For example, two LEDs may irradiate at 557 nm (selected from the first range of 400-600 nm), two LEDs may irradiate at 626 nm (selected from the second range of 600-700 nm) and two LEDs may irradiate at 747 nm (selected from the third range of 700-900 nm). When using a pair of similar LEDs 4413, one LED of the pair may be used as a reference to the other LED. According to some embodiments, absorbance or transmittance signals of each of every two similar LEDs may be compared. In some embodiments, only when the signals of each LED of any pair are similar, are these signals processed. If the signals of each of any pair of LEDs are not similar, these signals are not processed, as the results are not reliable enough.

In other embodiments, since six LEDs 4413 may constitute several combinations of three different LEDs, a processor may determine which set of three different LEDs is best to use. Based on the composition of in-vivo bodily fluids present in the GI tract, which mainly comprise blood, bile, and chlorophyll, intensity of absorbance of such fluids of irradiated illumination at wavelengths selected from the range of 400-600 nm should be higher compared to intensity of absorbance of irradiated illumination at wavelengths selected from the range of 600-700 nm. Furthermore, intensity of absorbance of GI fluids of illumination at wavelengths selected from the range of 600-700 nm should be higher compared to intensity of absorbance of illumination at wavelengths selected from the range of 700-900 nm. For example, intensity of absorbance of the GI tract fluids of light from an LED irradiating at 557 nm should be higher than intensity of absorbance of light from an LED irradiating at 626 nm, which should be higher than intensity of absorbance of light from an LED irradiating at 747 nm. Other LEDs irradiating at different wavelengths may be used, as long as comparison between intensity of absorbance of light is done between LEDs from the different ranges mentioned above. A processor may select a set of three different LEDs from the total six LEDs, which comply with the mentioned order of intensity of absorbance levels (as described above regarding the three ranges of wavelengths) at a specific time period, and may process their corresponding detected signals at that specific time period. However, when there is no such order of intensity of absorbance in none of the combinations of three different LEDs at a specific time period, as described above regarding the three ranges of wavelengths, none of the signals detected at that specific time period is processed, since there is an indication that the results are not reliable.

In some embodiments, the in-vivo diagnostic device, e.g., device 4410, may comprise an imaging head located on the device's end opposite gap 4412. Image data acquired by such a device may be used in order to determine which signal may be considered as a bleeding event. An image acquired simultaneously with a detected signal may be used to determine whether the signal indicates presence of blood or not, which may assist in receiving reliable results of bleeding detection by the sensing head of device 4410.

In some embodiments, when an in-vivo device, e.g., device 4410, comprises an imaging head in addition to a sensing head (e.g., the imaging head may be positioned opposite the sensing head), the imaging head (e.g., imaging head 4422) and sensing head (e.g., sensing head 4416) need not operate simultaneously; instead each of the device's heads may operate alone during different time periods and/or at different in-vivo locations. For example, the sensing head may operate since swallowing the device and as long as device 4410 is in the stomach. After a predetermined time period, which is longer than the time it typically takes an autonomous device to pass through the stomach, or after device 4410 recognizes it is no longer in the stomach but rather in the small bowel (using any of known methods, e.g., change in pH), the imaging head may begin its operation, whereas the sensing head may cease its operation. After a further period of time, which is longer than the time it typically takes a device to pass through a normally configured small bowel, or after device 4410 recognizes it is no longer in the small bowel but rather in the colon (using any of known methods, e.g., change in pH), the imaging head may cease its operation, whereas the sensing head may begin its operation again. In other embodiments, the sensing head and imaging head may operate simultaneously at certain in-vivo locations or certain time periods, while operating apart at other in-vivo locations or other time periods. Other combinations of operation of the sensing and imaging heads may be used.

The above methods according to FIGS. 51-52 may further comprise acquiring an in-vivo image or obtaining other data such as pH value for localization of the device. In this case, the device may comprise an imager and white light illumination sources positioned on a different side of the device, e.g., opposite the end of the device containing a gap, as shown in FIGS. 44A-44C, such that an in-vivo image may indicate the location in-vivo, along with the determination regarding the presence of blood provided by the sensing head. In other embodiments, the device may include a pH detector such that, based upon the pH level detected, a location of the device along the GI tract may be determined. In yet other embodiments, the localization of the device may be done using spectral information of bile and/or chlorophyll, while the spectral information of blood may indicate the presence of blood in-vivo, and in-vivo images may show the source of the bleeding on the tissue if any.

In some other embodiments, instead of comparing between absorbance spectra, the method may compare between the discrete signals detected by photodiode 14 and a predetermined threshold, as described with respect to FIGS. 11-12 in WO 2010/086859, mentioned above.

In yet other embodiments, endoluminal bodily fluid may include, for example, tumor markers. Tumor markers may include molecules expressed in bodily fluid or tissue that are associated with cancer. Typically, tumor markers may be cancerous cells or products of cancerous cells, and may represent aberrant production of what may be a typically normal element. Some markers, such as antibodies, may be produced in response to the presence of cancer. Tumor marker targeted molecules may have a high affinity to tumor markers and, under certain conditions, may adhere to tumor markers in a liquid environment. These may include antigens having specificity to tumor marker antibodies. Alternatively, tumor marker targeted molecules may include antibodies specific to tumor marker antigens. A patient may swallow tumor marker targeted molecules in advance, before swallowing the in-vivo diagnostic device, such that while the device passes along the GI tract, it may detect the marked tissue. Bodily fluid samples may be analyzed for other chemicals, compounds or molecules.

Various aspects of the various embodiments disclosed herein are combinable with the other embodiments disclosed herein. Although portions of the discussion herein may relate to six LEDs for irradiating the bodily fluid, the present invention is not limited in this regard, and may include, for example, seven or more LEDs, or less than six LEDs.

A device, system and method in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body.

It will be appreciated that the present invention is not limited to what has been particularly shown and described hereinabove. Rather the scope of the present invention is defined only by the claims which follow.

The invention claimed is:

1. A system for determining the type of a patient's bleeding profile over time, said system comprising:
   an in-vivo sensing device comprising:
   a housing comprising a sensing head in the form of a gap, which remains in contact with bodily fluids and through which the fluids pass when the device is within the GI tract;
   said sensing head comprising a plurality of illumination sources positioned on a first side of the gap, each illumination source for repeatedly irradiating the fluids within the gap at a different narrow band wavelength, and at least one light detector photodiode positioned on the opposite side of the gap and facing the illumination sources, for detecting light irradiated by the illumination sources and which passed through the fluids;
   a transmitter for transmitting a plurality of values representing the light detected over time by the at least one light detector to an external receiver;
   a memory unit for storing the values received by the external receiver;
   a processing unit configured for processing the stored values and for:
   converting the values to a series of blood concentration values measured consecutively over time, and
   identifying a bleeding event based on the blood concentration values as a function of time and based on a comparison of the blood concentration values to a threshold.

2. The system according to claim 1, wherein the processor is configured to identify a bleeding event indicating major-active bleeding over time if the blood concentration values show a peak above the threshold value after which a plurality of blood concentration values measured consecutively are below the peak but are still above the threshold value.

3. The system according to claim 1, wherein the processor is configured to identify a bleeding event indicating major-non-active bleeding over time if the blood concentration values show a steady peak close to the threshold value.

4. The system according to claim 1, wherein the processor is configured to identify a bleeding event indicating minor bleeding over time if the blood concentration values show at least one peak below the threshold value.

5. The system according to claim 1, wherein the processor is configured to identify a bleeding event indicating no bleeding over time if the blood concentration values are below the threshold value with no distinct peak over time.

6. The system according to claim 1, wherein said memory unit and said processing unit are incorporated within said external receiver.

7. The system according to claim 1, wherein said sensing head comprises a cover placed over the gap, said cover comprising at least one hole located on an axis perpendicular to an axis along which the illumination sources and the light detector are located.

8. The system according to claim 7, wherein said at least one hole comprises holes located on opposite sides of the gap.

9. The system according to claim 7, wherein said cover is shaped as a flexible accordion, said cover defining a space within the sensing head, the space defined within the sensing head having an initial un-squeezed volume which is configured to be filled with in-vivo-bodily fluids through said at least one hole, wherein the cover has a spring constant which is:
  soft enough so that the cover can be squeezed whenever peristaltic pressure is applied onto it thus causing the space defined by said cover to decrease and the in-vivo bodily fluids to exit from said sensing head through said at least one hole, and
  strong enough to cause the space defined by the cover to return to its initial un-squeezed volume whenever the peristaltic pressure is no longer applied onto said cover, thus enabling new in-vivo bodily fluids to enter said sensing head through said at least one hole.

10. The system according to claim 9, wherein said hole is located in close proximity to a sensing area, said sensing area being located between said illumination sources and said at least one light detector.

11. The system according to claim 1, wherein said in-vivo sensing device further comprises an imaging head.

12. The system according to claim 11, wherein said imaging head is located at one end of said housing, opposite to the end of the housing comprising the sensing head.

13. The system according to claim 1, wherein said system further comprises a display unit for displaying a graph of the blood concentration values over time.

14. The system according to claim 1, wherein said plurality of illumination sources comprise at least three LEDs, wherein at least one LED is selected from each of the following three ranges: a first range is between 400 nm to 600 nm, a second range is between 600 nm to 700 nm, and a third range is between 700 nm to 900 nm.

15. The system according to claim 14, wherein said plurality of illumination sources comprise six LEDs, wherein two are selected from the first range, three are selected from the second range and one is selected form the third range.

16. A method for determining the type of a patient's bleeding profile over time, said method comprising:
  irradiating in-vivo fluids passing through a gap in a housing of an in-vivo sensing device introduced to the GI tract of a subject with a plurality of illumination sources positioned on a first side of a gap, each illumination source for irradiating at a different narrow band wavelength;
  detecting, with at least one light detector photodiode positioned on the opposite side of the gap and facing the illumination sources, light irradiated by the illumination sources;
  transmitting a plurality of values representing the light detected over time;
  converting said values to blood concentration values over time;
  identifying a bleeding event based on the blood concentration values as a function of time and based on a comparison of the blood concentration values to a predetermined threshold value.

17. The method according to claim 16, wherein if the blood concentration values show a peak above the threshold value after which a plurality of blood concentration values measured consecutively are below the peak but are still above the threshold value, the bleeding event indicates major-active bleeding over time.

18. The method according to claim 16, wherein if the blood concentration values show a steady peak close to the threshold value, the bleeding event indicates a major-non-active bleeding over time.

19. The method according to claim 16, wherein if the blood concentration values show at least one peak below the threshold value, the bleeding event indicates minor bleeding over time.

20. The method according to claim 16, wherein if the blood concentration values are below the threshold value with no distinct peak over time, the bleeding event indicates no bleeding over time.

* * * * *